(12) United States Patent
Bauman et al.

(10) Patent No.: US 7,223,798 B2
(45) Date of Patent: May 29, 2007

(54) LIPOXIN $A_4$ ANALOGS

(75) Inventors: John G Bauman, El Sobrante, CA (US); William J Guilford, Belmont, CA (US); John F Parkinson, Martinez, CA (US); Werner Skuballa, Berlin (DE); Babu Subramanyam, Benicia, CA (US)

(73) Assignee: Schering Aktiengesellschaft, Berlin (DE)

( * ) Notice: Subject to any disclaimer, the term of this patent is extended or adjusted under 35 U.S.C. 154(b) by 100 days.

(21) Appl. No.: 10/782,024

(22) Filed: Feb. 18, 2004

(65) Prior Publication Data

US 2004/0162433 A1 Aug. 19, 2004

Related U.S. Application Data

(63) Continuation of application No. 10/279,084, filed on Oct. 22, 2002, now Pat. No. 6,831,186.

(60) Provisional application No. 60/338,684, filed on Nov. 6, 2001.

(51) Int. Cl.
*A01N 37/00* (2006.01)
(52) U.S. Cl. .................. 514/559; 514/552; 554/224
(58) Field of Classification Search ............... 554/224; 514/552, 559
See application file for complete search history.

(56) References Cited

U.S. PATENT DOCUMENTS

| 5,441,951 A | * | 8/1995 | Serhan ................. 514/513 |
| 6,066,466 A | | 5/2000 | Serhan et al. ............. 435/18 |
| 6,100,296 A | | 8/2000 | Madara et al. ............ 514/552 |

FOREIGN PATENT DOCUMENTS

| WO | WO 94/29262 | 12/1994 |
| WO | WO 95/01179 | 1/1995 |
| WO | WO 98/11049 | 3/1998 |
| WO | WO 00/54761 | 9/2000 |
| WO | WO 00/54767 | 9/2000 |
| WO | WO 00/55109 | 9/2000 |
| WO | WO 01/34144 | 5/2001 |
| WO | WO 01/34548 | 5/2001 |
| WO | WO 01/70664 | 9/2001 |

OTHER PUBLICATIONS

Brezinski and Serhan, "Characterization of Lipoxins by Combined Gas Chromatography and Electron-capture Negative Ion Chemical Ionization Mass Spectrometry: Formation of Lipoxin $A_4$ by Stimulated Human Whole Blood," *Biological Mass Spectrometry* 20: 45-52, 1991.
Buchmann, B. et al., "Synthesis of a Chemically and Metabolically Stable and Biologically Potent $PGD_2$-Analogue," *Tetrahedron Letters* 31(24): 3425-3428, 1990.

Colgan, S. et al., "Lipoxin $A_4$ Modulates Transmigration of Human Neutrophils across Intestinal Epthelial Monolayers," *Journal of Clinical Inverstigation* 92: 75-82, 1993.
Ellis, C.K. et al., "Metabolism of Prostaglandin $D_2$ in the Monkey," *The Journal of Biological Chemistry* 254(10): 4152-4163, May 25, 1979.
Fiore, S. et al., "Induction of Functional Lipoxin $A_4$ Receptors in HL-60 Cells," *Blood* 81(12): 3395-3403, Jun. 15, 1993.
Fiore, S. et al., "Lipoxin Recognition Sites. Specific Binding of Labeled Lipoxin $A_4$ with Human Neutrophils," *The Journal of Biological Chemistry* 267(23): 16168-16176, Aug. 15, 1992.
Krause, W. et al., "Biotransformation of the stable prostacyclin analogue, iloprost, in the rat," Abstract from *Drug Metab. Dispos* 12: 645-651, 1984. Abstract available at http://dmd.aspetjournals.org.
Liston and Roberts, "Metabolic Fate of Radiolabeled Postaglandin $D_2$ in a Normal Human Male Volunteer," *The Journal of Biological Chemistry* 260(24): 13172-13180, 1985.
Maddox, J.F. et al., "Lipoxin $A_4$ Stable Analogs Are Potent Mimetics That Stimulate Human Monocytes and THP-1 Cells via a G-protein-linked Lipoxin $A_4$ Receptor," *The Journal of Biological Chemistry* 272(11): 6972-6978, Mar. 14, 1997.
Maderna, P. et al., "Influence of lipoxin $A_4$ and other lipoxygenase-derived eicosanoids on tissue factor expression," *Am. J. Physiol. Cell Physiol.* 279: C945-C953, 2000.
O'Sullivan, S. et al., "Analysis of prostaglandin $D_2$ metabolites in urine: Comparison between enzyme immunoassay and negative ion chemical ionization gas chromatography-mass spectrometry," *Prostaglandis & other Lipid Mediators* 57: 149-165, 1999.
Serhan, C. et al., "Aspirin-triggered 15-epi-lipoxin $A_4$ and novel lipoxin $B_4$ stable analogs inhibit neutrophil-mediated changes in vascular permeability," *Advances in Experimental Medicine and Biology* 469: 287-293, 1999.
Serhan, C. et al., "Design of Lipoxin $A_4$ Stable Analogs That Block Transmigration and Adhesion of Human Neutrophils," *Biochemistry* 34: 14609-14615, 1995.

(Continued)

*Primary Examiner*—Deborah D. Carr
(74) *Attorney, Agent, or Firm*—Seed IP Law Group PLLC

(57) ABSTRACT

This invention is directed to lipoxin A4 analogs of the following formula (II):

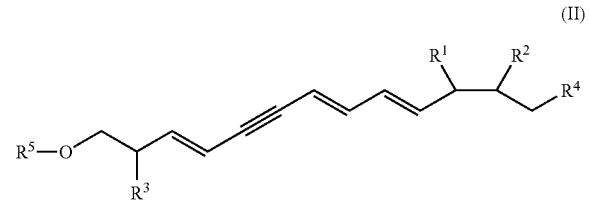

wherein $R^1$, $R^2$, $R^3$, $R^4$ and $R^5$ are described herein. These analogs are useful in treating inflammatory and autoimmune disorders in humans. These analogs are also useful in treating pulmonary or respiratory tract inflammation in humans.

20 Claims, No Drawings

OTHER PUBLICATIONS

Serhan, C. et al., "Lipoxin $A_4$ Metabolism by Differentiated HL-60 Cells and Human Monocytes: Conversion to Novel 15-Oxo and Dihydro Products," *Biochemistry 32*: 6313-6319, 1993.

Skuballa, W. et al., "Synthesis of a New Chemically and Metabolically Stable Prostacyclin Analogue with High and Long-Lasting Oral Activity," *Journal of Medicinal Chemistry 29*(3): 313-315, 1986.

Takano, T. et al., "Neutrophil-mediated Changes in Vascular Permeability Are Inhibited by Topical Application of Aspirin-triggered 15-epi-lipoxi $A_4$ and Novel Lipoxin $B_4$ Stable Analogues," *Journal of Clinical Investigation 101*: 819-826, 1998.

Webber, S. et al., "The total synthesis of the lipoxins and related compounds," *Advances in Experimental Medicine and Biology 229*: 61-77, 1988.

Bannenberg, G. et al., "Lipoxins and novel 15-epi-lipoxin analogs display potent anti-inflammatory actions after oral administration," *British Journal of Pharmacology 143*(1): 43-52, 2004.

Fiorucci, S. et al., "A β-oxidation-resistant lipoxin $A_4$ analog treats hapten-induced colitis by attenuating inflammation and immune dysfunction," *Proc. Natl. Acad. Sci. USA 101*(44): 15736-15741, Nov. 2, 2004.

Guilford, W.J. et al., "Novel 3-Oxa Lipoxin $A_4$ Analogues with Enhanced Chemical and Metabolic Stability Have Anti-inflammatory Activity in Vivo," *Journal of Medicinal Chemistry 47*(8): 2157-2165, 2004.

Guilford, W.J. et al., "Second-generation beta-oxidation resistant 3-oxa-lipoxin $A_4$ analogs," *Prostaglandins, Leukotrienes and Essential Fatty Acids 73*: 245-250, 2005.

\* cited by examiner

LIPOXIN A₄ ANALOGS

CROSS REFERENCE TO RELATED APPLICATIONS

This application is a continuation of U.S. patent application Ser. No. 10/279,084, filed Oct. 22, 2002, now U.S. Pat. No. 6,831,186, which claims the benefit of U.S. Provisional Patent Application No. 60/338,684, filed Nov. 6, 2001, whereby the disclosure of both applications are incorporated herein by reference in their entireties.

BACKGROUND OF THE INVENTION

1. Field of the Invention

The invention relates to lipoxin $A_4$ analogs, their use in treating inflammatory and autoimmune disorders and pulmonary and respiratory tract inflammation, and pharmaceutical compositions containing the analogs and processes for their preparation.

2. Background of the Invention

Lipoxins, together with leukotrienes, prostaglandins, and thromboxanes, constitute a group of biologically active oxygenated fatty acids collectively referred to as the eicosanoids. Eicosanoids are all synthesised de novo from membrane phospholipid via the arachidonic acid cascade of enzymes. Since their initial discovery in 1984, it has become apparent that lipoxins, which are a structurally unique class of eicosanoids, possess potent anti-inflammatory properties that suggest they may have therapeutic potential (Serhan, C. N., *Prostaglandins* (1997), Vol. 53, pp. 107–137; O'Meara, Y. M. et al., *Kidney Int. (Suppl.)* (1997), Vol. 58, pp. S56–S61; Brady, H. R. et al., *Curr. Opin. Nephrol. Hypertens.* (1996), Vol. 5, pp. 20–27; and Serhan, C. N., *Biochem. Biophys. Acta.* (1994), Vol. 1212, pp. 1–25). Of particular interest is the ability of lipoxins to antagonise the pro-inflammatory functions of leukotrienes in addition to other inflammatory agents such as platelet activating factor, FMLP, immune complexes and TNFα. Lipoxins are thus potent anti-neutrophil (PMN) agents which inhibit PMN chemotaxis, homotypic aggregation, adhesion, migration across endothelial and epithelial cells, margination/diapedesis and tissue infiltration (Lee, T. H., et al., *Clin. Sci.* (1989), Vol. 77, pp. 195–203; Fiore, S., et al., *Biochemistry* (1995), Vol. 34, pp. 16678–16686; Papyianni, A., et al., *J. Immunol.* (1996), Vol. 56, pp. 2264–2272; Hedqvist, P., et al., *Acta. Physiol. Scand.* (1989), Vol. 137, pp. 157–572; Papyianni, A., et al., *Kidney Intl.* (1995), Vol.47, pp. 1295–1302). In addition, lipoxins are able to down-regulate endothelial P-selectin expression and adhesiveness for PMNs (Papyianni, A., et al., *J. Immunol.* (1996), Vol. 56, pp. 2264–2272), bronchial and vascular smooth muscle contraction, mesangial cell contraction and adhesiveness (Dahlen, S. E., et al., *Adv. Exp. Med. Biol.* (1988), Vo. 229, pp. 107–130; Christie, P. E., et al., *Am. Rev. Respir. Dis.* (1992), Vol. 145, pp. 1281–1284; Badr, K. F., et al., *Proc. Natl. Acad. Sci.* (1989), Vol. 86, pp. 3438–3442; and Brady, H. R., et al., *Am. J. Physiol.* (1990), Vol. 259, pp. F809–F815) and eosinophil chemotaxis and degranulation (Soyombo, O., et al., *Allergy* (1994), Vol. 49, pp. 230–234).

This unique anti-inflammatory profile of lipoxins, particularly lipoxin $A_4$, has prompted interest in exploiting their potential as therapeutics for the treatment of inflammatory or autoimmune disorders and pulmonary and respiratory tract inflammation. Such disorders and inflammation which exhibit a pronounced inflammatory infiltrate are of particular interest and include dermatologic diseases, such as psoriasis, and rheumatoid arthritis, and respiratory disorders, such as asthma.

As with other endogenous eicosanoids, naturally occurring lipoxins are unstable products which are rapidly metabolized and inactivated (Serhan, C. N., *Prostaglandins* (1997), Vol. 53, pp. 107–137). This has limited the development of the lipoxin field of research, particularly with respect to in vivo pharmacological assessment of the anti-inflammatory profile of lipoxins. Several U.S. patents have issued directed to compounds having the active site of lipoxin $A_4$, but with a longer tissue half-life. See, e.g., U.S. Pat. Nos. 5,441,951 and 5,648,512, the disclosures of which are incorporated in full by reference herein. These compounds retain lipoxin $A_4$ receptor binding activity and the potent in vitro and in vivo anti-inflammatory properties of natural lipoxins (Takano, T., et al., J. Clin. Invest. (1998), Vol. 101, pp. 819–826; Scalia, R., et al., Proc. Natl. Acad. Sci. (1997), Vol. 94, pp. 9967–9972; Takano, T., et al., *J. Exp. Med.* (1997), Vol. 185, pp. 1693–1704; Maddox, J. F., et al., J. Biol. Chem. (1997), Vol. 272, pp. 6972–6978; Serhan, C. N., et al., *Biochemistry* (1995), Vol. 34, pp. 14609–14615).

All of the references cited herein, including published patent applications and journal articles, are incorporated in full by reference herein.

SUMMARY OF THE INVENTION

This invention is directed to potent, selective and metabolically/chemically stable lipoxin $A_4$ analogs and their use in treating inflammatory or autoimmune disorders and pulmonary or respiratory tract inflammation in mammals, particularly humans.

In one aspect, the invention is directed to compound of formula (I) or formula (II):

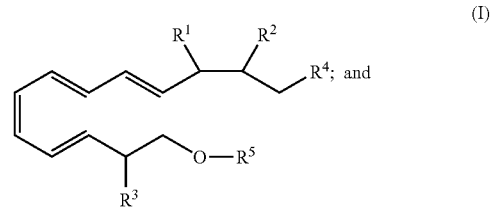

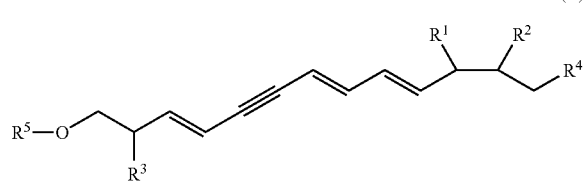

wherein:

each $R^1$, $R^2$ and $R^3$ are independently halo, $-OR^6$, $-SR^6$, $-S(O)_tR^7$ (where t is 1 or 2) or $-N(R^7)R^8$;

or $R^1$ and $R^2$ together with the carbons to which they are attached form a monocyclic heterocyclic structure selected from the following:

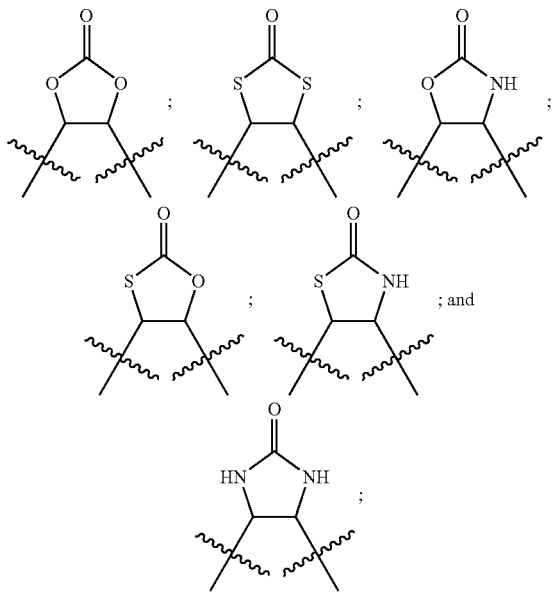

or $R^1$ and $R^2$ together with the carbons to which they are attached form the following bicyclic heterocyclic structure:

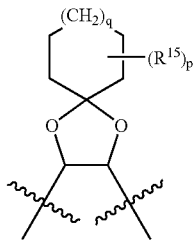

(where q is 0 to 3, p is 1 to 4 and each $R^{15}$ is hydrogen, alkyl, aralkyl or aryl);

each $R^4$ is $-R^9-R^{12}$, $-R^9-R^{13}-R^{11}$, $-R^9-O-R^{10}-R^{11}$, $-R^9-O-R^{12}$, $-R^9-C(O)-R^{10}-R^{11}$, $-R^9-N(R^7)-R^{10}-R^{11}$, $-R^9-S(O)_t-R^{10}-R^{11}$ (where t is 0 to 2), or $-R^9-C(F)_2-R^9-R^{11}$;

each $R^5$ is aryl (optionally substituted by one or more substituents selected from the group consisting of alkyl, alkoxy, halo, haloalkyl and haloalkoxy) or aralkyl (optionally substituted by one or more substituents selected from the group consisting of alkyl, alkoxy, halo, haloalkyl and haloalkoxy);

each $R^6$ is independently hydrogen, alkyl, aryl, aralkyl, $-C(O)R^7$, $-C(S)R^7$, $-C(O)OR^{14}$, $-C(S)OR^{14}$, $-C(O)N(R^7)R^8$, or $-C(S)N(R^7)R^8$;

each $R^7$ is independently hydrogen, alkyl, cycloalkyl, aryl, or aralkyl;

$R^8$ is independently hydrogen, alkyl, aryl, aralkyl, $-C(O)R^7$, $-C(O)OR^{14}$, or cycloalkyl (optionally substituted with one more substituents selected from the group consisting of alkyl, $-N(R^7)_2$, and $-C(O)OR^7$);

each $R^9$ is independently a direct bond or a straight or branched alkylene chain;

each $R^{10}$ is independently a straight or branched alkylene chain, a straight or branched alkenylene chain, a straight or branched alkynylene chain or a cycloalkylene;

each $R^{11}$ is independently $-C(O)OR^7$, $-C(O)N(R^7)_2$, $-P(O)(OR^7)_2$, $-S(O)_2OR^7$, $-S(O)_2N(H)R^7$ or tetrazole;

$R^{12}$ is aryl (substituted by $-C(O)OR^7$ or $-C(O)N(R^7)_2$ and optionally by one or more substituents selected from the group consisting of alkyl, alkoxy, halo, haloalkyl and haloalkoxy) or aralkyl (substituted by $-C(O)OR^7$ or $-C(O)N(R^7)_2$ and optionally by one or more substituents selected from the group consisting of alkyl, alkoxy, halo, haloalkyl and haloalkoxy);

$R^{13}$ is a branched alkylene chain, a straight or branched alkenylene chain or a cycloalkylene; and $R^{14}$ is alkyl, aryl or aralkyl;

as a single stereoisomer, a mixture of stereoisomers, a racemic mixture of stereoisomers; or as a cyclodextrin clathrate thereof, or as a pharmaceutically acceptable salt thereof.

In another aspect, this invention is directed to pharmaceutical compositions useful in treating an inflammatory or autoimmune disorder in a mammal, particularly a human, wherein the composition comprises one or more pharmaceutically acceptable excipient(s) and a therapeutically effective amount of a compound of formula (I) or formula (II) as described above.

In another aspect, this invention is directed to pharmaceutical compositions useful in treating pulmonary or respiratory tract inflammation in a mammal, particularly a human, wherein the composition comprises one or more pharmaceutically acceptable excipient(s) and a therapeutically effective amount of a compound of formula (I) or formula (II) as described above.

In another aspect, this invention is directed to methods of treating an inflammatory or autoimmune disorder in a mammal, particularly a human, wherein the method comprises administering to the mammal in need thereof a therapeutically effective amount of a compound of formula (I) or (II) as described above.

In another aspect, this invention is directed to methods of treating pulmonary or respiratory tract inflammation in a mammal, wherein the method comprises adminstering to a mammal, particularly a human, in need thereof, a therapeutically effective amount of a compound of formula (I) or formula (II):

DETAILED DESCRIPTION OF THE INVENTION

A. Definitions

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art. Furthermore, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, the alkyl radical may be optionally substituted by one or more substituents selected from the group consisting of cyano, nitro, —$R^9$—$OR^6$, —$R^9$—N=N—O—$R^{16}$, —$R^9$—$N(R^6)_2$, —$R^9$—$C(O)R^6$, —$R^9$—$C(O)OR^6$, —$R^9$—$C(O)N(R^6)_2$, —$R^9$—$N(R^6)C(O)OR^{16}$, —$R^9$—$N(R^6)C(O)R^6$, —$R^9$—$S(O)_tOR^6$ (where t is 0 to 2), —$R^9$—$S(O)_tR^6$ (where t is 0 to 2), —$R^9$—$S(O)_tN(R^6)_2$ (where t is 0 to 2) where each $R^6$ and $R^9$ is as defined above in the Summary of the Invention and each $R^{16}$ is hydrogen, alkyl or aralkyl. Unless stated otherwise specifically in the specification, it is understood that such substitution can occur on any carbon of the alkyl group.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like.

"Alkenyl" refers to a straight or branched monovalent hydrocarbon chain radical consisting solely of carbon and hydrogen atoms, containing at least one double bond, having from two to eight carbon atoms, and which is attached to the rest of the molecule by a single bond, e.g., ethenyl, prop-1-enyl, but-1-enyl, pent-1-enyl, penta-1,4-dienyl, and the like. Unless stated otherwise specifically in the specification, the alkenyl radical may be optionally substituted by one or more substituents selected from the group consisting of cyano, nitro, —$R^9$—$OR^6$, —$R^9$—N=N—O—$R^{16}$, —$R^9$—$N(R^6)_2$, —$R^9$—$C(O)R^6$, —$R^9$—$C(O)OR^6$, —$R^9$—$C(O)N(R^6)_2$, —$R^9$—$N(R^6)C(O)OR^{16}$, —$R^9$—$N(R^6)C(O)R^6$, —$R^9$—$S(O)_tOR^6$ (where t is 0 to 2), —$R^9$—$S(O)_tR^6$ (where t is 0 to 2), —$R^9$—$S(O)_tN(R^6)_2$ (where t is 0 to 2) where each $R^6$ and $R^9$ is as defined above in the Summary of the Invention and each $R^{16}$ is hydrogen, alkyl or aralkyl. Unless stated otherwise specifically in the specification, it is understood that such substitution can occur on any carbon of the alkenyl group.

"Alkenylene chain" refers to a straight or branched divalent hydrocarbon chain consisting solely of carbon and hydrogen, containing at least one double bond and having from two to eight carbon atoms, e.g., ethenylene, prop-1-enylene, but-1-enylene, pent-1-enylene, hexa-1,4-dienylene, and the like.

"Alkynyl" refers to a straight or branched monovalent hydrocarbon chain radical consisting solely of carbon and hydrogen atoms, containing at least one triple bond, having from two to eight carbon atoms, and which is attached to the rest of the molecule by a single bond, e.g., ethynyl, prop-1-ynyl, but-1-ynyl, pent-1-ynyl, pent-3-ynyl, and the like. Unless stated otherwise specifically in the specification, the alkynyl radical may be optionally substituted by one or more substituents selected from the group consisting of cyano, nitro, —$R^9$—$OR^6$, —$R^9$—N=N—O—$R^{16}$, —$R^9$—$N(R^6)_2$, —$R^9$—$C(O)R^6$, —$R^9$—$C(O)OR^6$, —$R^9$—$C(O)N(R^6)_2$, —$R^9$—$N(R^6)C(O)OR^{16}$, —$R^9$—$N(R^6)C(O)R^6$, —$R^9$—$S(O)_tOR^6$ (where t is 0 to 2), —$R^9$—$S(O)_tR^6$ (where t is 0 to 2), —$R^9$—$S(O)_tN(R^6)_2$ (where t is 0 to 2) where each $R^6$ and $R^9$ is as defined above in the Summary of the Invention and each $R^{16}$ is hydrogen, alkyl or aralkyl. Unless stated otherwise specifically in the specification, it is understood that for radicals, as defined below, that contain a substituted alkynyl group that the substitution can occur on any carbon of the alkynyl group.

"Alkynylene chain" refers to a straight or branched divalent hydrocarbon chain consisting solely of carbon and hydrogen, containing at least one triple bond and having from two to eight carbon atoms, e.g., ethynylene, prop-1-ynylene, but-1-ynylene, pent-3-ynylene, hexa-1,4-diynylene, and the like.

"Alkoxy" refers to a radical of the formula —$OR_a$ where $R_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like.

"Amino" refers to the —$NH_2$ radical.

"Aryl" refers to a phenyl or naphthyl radical. Unless stated otherwise specifically in the specification, the term "aryl" or the prefix "ar-" (such as in "aralkyl") is meant to include aryl radicals which may be optionally substituted by one or more substituents selected from the group consisting of alkyl, alkenyl, halo, haloalkyl, cyano, nitro, aryl, aralkyl, cycloalkyl, —$R^9$—$OR^6$, —$R^9$—N=N—O—$R^{16}$, —$R^9$—$N(R^6)_2$, —$R^9$—$C(O)R^6$, —$R^9$—$C(O)OR^6$, —$R^9$—$C(O)N(R^6)_2$, —$R^9$—$N(R^6)C(O)OR^{16}$, —$R^9$—$N(R^6)C(O)R^6$, —$R^9$—$S(O)_tOR^6$ (where t is 0 to 2), —$R^9$—$S(O)_tR^6$ (where t is 0 to 2), —$R^9$—$S(O)_tN(R^6)_2$ (where t is 0 to 2) where each $R^6$ and $R^9$ is as defined above in the Summary of the Invention and each $R^{16}$ is hydrogen, alkyl or aralkyl. Unless stated otherwise specifically in the specification, it is understood that such substitution can occur on any carbon of the aryl group.

"Aralkyl" refers to a radical of the formula —$R_aR_b$ where $R_a$ is an alkyl radical as defined above and $R_b$ is an aryl radical as defined above, e.g., benzyl, and the like. The aryl radical may be optionally substituted as described above.

"Carboxy" refers to the —C(O)OH radical.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury CN), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogus reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

"Clathrates" as used herein refers to substances which fix gases, liquids or compounds as inclusion complexes so that the complex may be handled in solid form and the included constituent (or "guest" molecule) subsequently releases by the action of a solvent or by melting. The term "clathrate" is used interchangeably herein with the phrase "inclusion molecule" or with the phrase "inclusion complex". Clathrates used in the instant invention are prepared from cyclodextrins. Cyclodextrins are widely known as having the ability to form clathrates (i.e., inclusion compounds) with a variety of molecules. See, for example, *Inclusion Compounds*, edited by J. L. Atwood, J. E. D. Davies, and D. D. MacNicol, London, Orlando, Academic Press, 1984; Goldberg, I., "The Significance of Molecular Type, Shape and Complementarity in Clathrate Inclusion", *Topics in Current Chemistry* (1988), Vol. 149, pp. 2–44; Weber, E. et al., "Functional Group Assisted Clathrate Formation—Scissor-Like and Roof-Shaped Host Molecules", *Topics in Current Chemistry* (1988), Vol. 149, pp. 45–135; and MacNicol, D. D. et al., "Clathrates and Molecular Inclusion Phenomena", *Chemical Society Reviews* (1978), Vol. 7, No. 1, pp. 65–87. Conversion into cyclodextrin clathrates is known to increase the stability and solubility of certain compounds, thereby facilitating their use as pharmaceutical agents. See, for example, Saenger, W., "Cyclodextrin Inclusion Compounds in Research and Industry", *Angew. Chem. Int. Ed. Engl.* (1980), Vol. 19, pp. 344–362; U.S. Pat. No. 4,886,788 (Schering AG); U.S. Pat. No. 6,355,627 (Takasago); U.S. Pat. No. 6,288,119 (Ono Pharmaceuticals); U.S. Pat. No. 6,110,969 (Ono Pharmaceuticals); U.S. Pat. No. 6,235,780 (Ono Pharmaceuticals); U.S. Pat. No. 6,262,293 (Ono Pharmaceuticals); U.S. Pat. No. 6,225,347 (Ono Pharmaceuticals); and U.S. Pat. No. 4,935,446 (Ono Pharmaceuticals).

"Cyclodextrin" refers to cyclic oligosaccharides consisting of at least six glucopyranose units which are joined together by $\alpha(1-4)$ linkages. The oligosaccharide ring forms a torus with the primary hydroxyl groups of the glucose residues lying on the narrow end of the torus. The secondary glucopyranose hydroxyl groups are located on the wider end. Cyclodextrins have been shown to form inclusion complexes with hydrophobic molecules in aqueous solutions by binding the molecules into their cavities. The formation of such complexes protects the "guest" molecule from loss of evaporation, from attack by oxygen, visible and ultraviolet light and from intra- and intermolecular reactions. Such complexes also serve to "fix" a volatile material until the complex encounters a warm moist environment, at which point the complex will dissolve and dissociate into the guest molecule and the cyclodextrin. For purposes of this inveniton, the six-glucose unit containing cyclodextrin is specified as $\alpha$-cyclodextrin, while the cyclodextrins with seven and eight glucose residues are designated as $\beta$-cyclodextrin and $\gamma$-cyclodextrin, respectively. The most common alternative to the cyclodextrin nomenclature is the naming of these compounds as cycloamyloses.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, aryl, aralkyl, cycloalkyl, heterocyclyl, heterocyclylalkyl, $-R^9-OR^6$, $-R^9-N=N-O-R^{16}$, $-R^9-N(R^6)_2$, $-R^9-C(O)R^6$, $-R^9-C(O)OR^6$, $-R^9-C(O)N(R^6)_2$, $-R^9-N(R^6)C(O)OR^{16}$, $-R^9-N(R^6)C(O)R^6$, $-R^9-S(O)_tOR^6$ (where t is 0 to 2), $-R^9-S(O)_tR^6$ (where t is 0 to 2), $-R^9-S(O)_tN(R^6)_2$ (where t is 0 to 2) where each $R^6$ and $R^9$ is as defined above in the Summary of the Invention and each $R^{16}$ is hydrogen, alkyl or aralkyl. Unless stated otherwise specifically in the specification, it is understood that such substitution can occur on any carbon of the cycloalkyl group.

"Cycloalkylene" refers to a stable divalent monocyclic or bicyclic hydrocarbon consisting solely of carbon and hydrogen atoms, having from three to ten carbon atoms, and which is saturated and attached to the rest of the molecule by two single bonds, e.g., cyclopropylene, cyclobutylene, cyclopentylene, cyclohexylene, decalinylene and the like. Unless otherwise stated specifically in the specification, the term "cycloalkylene" is meant to include cycloalkylene moieties which are optionally substituted by one or more substituents independently selected from the group consisting of alkyl, alkoxy, halo, haloalkyl, haloalkoxy, hydroxy, amino, and carboxy.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula $-OR_c$ where $R_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Mammal" includes humans and domesticated animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7–9, 21–24 (Elsevier, Amsterdam).

A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" refers to that amount of a compound of the invention which, when administered to a mammal, particularly a human, in need thereof, is sufficient to effect treatment, as defined below, for inflammatory or autoimmune disorders or pulmonary or respiratory tract inflammation. The amount of a compound of the invention which constitutes a "therapeutically effective amount" will vary depending on the compound, the inflammatory or autoimmune disorder, or pulmonary or respiratory tract inflammation, and its severity, and the age of the mammal to be treated, but can be determined routinely by one of ordinary skill in the art having regard to his own knowledge and to this disclosure.

"Treating" or "treatment" as used herein covers the treatment of a inflammatory or autoimmune disorder in a mammal, preferably a human, or the treatment of a pulmonary or respiratory tract inflammation in a mammal, preferably a human, and includes:

(i) preventing the disorder or inflammation from occurring in a mammal, in particular, when such mammal is predisposed to the disorder but has not yet been diagnosed as having it;

(ii) inhibiting the disorder or inflammation, i.e., arresting its development; or (iii) relieving the disorder or inflammation, i.e., causing regression of the disorder or inflammation.

The compounds of the invention, as a single stereoisomer, a mixture of stereoisomers, or as a racemic mixture of stereoisomers; or as a cyclodextrin clathrate thereof, or as a pharmaceutically acceptable salt thereof, may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein is a modified form of the I.U.P.A.C. nomenclature system wherein the compounds of the invention are named herein as derivatives of the hexadecanoic moiety. For example, the following compound of formula (I) where $R^1$, $R^1$ and $R^3$ are each —$OR^6$ (where $R^6$ is hydrogen); $R^4$ is —$R^9$—O—$R^{10}$—$R^{11}$ (where $R^9$ is a direct bond, $R^{10}$ is methylene and $R^{11}$ is —C(O)OH); and $R^5$ is phenyl substituted at the 4-position by fluoro, i.e.,

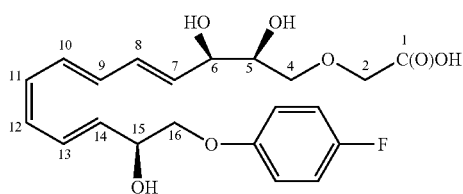

is named herein as (5S,6R,7E,9E,11Z,13E,15S)-16-(4-fluorophenoxy)-5,6,15-trihydroxy-3-oxa-7,9,11,13-hexadecatetraenoic acid. Unless otherwise indicated by the nomenclature, compound names are intended to include any single stereoisomer, enantiomer, racemate or mixtures thereof.

For purposes of this disclosure, in those compounds of the invention wherein $R^1$ and $R^2$ together with the carbons to which they are attached form the the following heterocyclic structures:

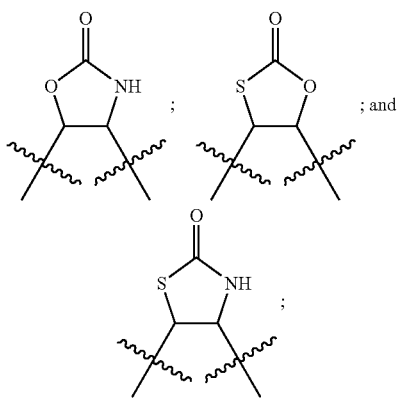

it is understood that the structures include the following reverse structures:

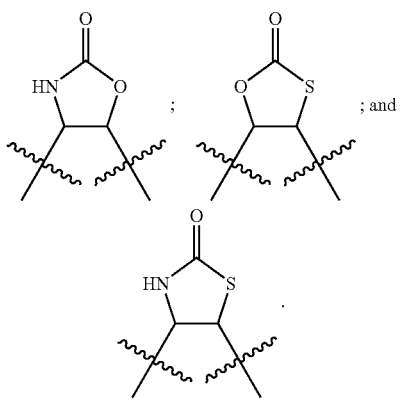

B. Utility of the Compounds of the Invention

The compounds of the invention are lipoxin $A_4$ analogs that have similar biological activity of natural lipoxin $A_4$, but with an enhanced resistance to metabolic degradation. Accordingly, the compounds of the invention are useful in treating inflammatory or autoimmune disorders in mammals, particularly in humans. In particular, the compounds of the invention are useful in inhibiting acute or chronic inflammation or an inflammatory or autoimmune response that is mediated by neutrophils, eosinophils, T lymphocytes, NK cells or other immune cells which contribute to the pathogenesis of inflammatory, immune or autoimmune diseases. The compounds are also useful in the treatment of proliferative disorders including, but not limited to, those associated with derangements in the inflammatory or immune response, such as cancer. The compounds are also useful as inhibitors of angiogenic responses in the pathogenesis of cancer.

Accordingly, the compounds can be used to treat the following inflammatory or autoimmune disorders in mammals, particularly humans: anaphylactic reactions, allergic reactions, allergic contact dermatitis, allergic rhinitis, chemical and non-specific irritant contact dermatitis, urticaria, atopic dermatitis, psoriasis, septic or endotoxic shock, hemorrhagic shock, shock-like syndromes, capillary leak syndromes induced by immunotherapy of cancer, acute respiratory distress syndrome, traumatic shock, immune- and pathogen-induced pneumonias, immune complex-mediated pulmonary injury and chronic obstructive pulmonary disease, inflammatory bowel diseases including ulcerative colitis, Crohn's disease and post-surgical trauma, gastrointestinal ulcers, diseases associated with ischemia-reperfusion injury including acute myocardial ischemia and infarction, acute renal failure, ischemic bowel disease and acute hemorrhagic or ischemic stroke, immune-complex-mediated glomerulonephritis, autoimmune diseases including insulin-dependent diabetes mellitus, multiple sclerosis, rheumatoid arthritis, osteoarthritis and systemic lupus erythematosus, acute and chronic organ transplant rejection, transplant arteriosclerosis and fibrosis, cardiovascular disorders including hypertension, atherosclerosis, aneurysm, critical leg ischemia, peripheral arterial occlusive disease and Reynaud's syndrome, complications of diabetes including diabetic nephropathy, neuropathy and retinopathy, ocular disorders including macular degeneration and glaucoma, neurodegenerative disorders including delayed neurodegeneration in stroke, Alzheimer's disease, Parkinson's disease, encephalitis and HIV dementia, inflammatory and neuropathic pain, including arthritic pain, periodontal disease including gingivitis, ear infections, migraine, benign prostatic hyperplasia, cancers including, but not limited to, leukemias and lymphomas, prostate cancer, breast cancer, lung cancer, malignant melanoma, renal carcinoma, head and neck tumors and colorectal cancer.

The compounds are also useful in treating folliculitis induced by inhibitors of epidermal growth factor (EGF) or epidermal growth factor receptor (EGFR) kinase used in the treatment of solid tumors. Clinical trials have revealed folliculitis (inflammation of the hair follicle manifested by severe acne-like skin rash on the face, chest and upper back) as a major dose-limiting side effect of such treatments. Such folliculitis is associated with an infiltraiton of neutrophils suggesting products secreted by activated neutrophils to be the cause of the inflammation. The lipoxin $A_4$ analogs of the instant invention inhibit neutrophil or eosinophil-mediated inflammation, and are therefore useful in treating such folliculitis, thereby improving the quality of life of the treated cancer patients but also allowing for the increase of the dosage of the EGF inhibitor or EGFR kinase inhibitor or the extension of the duration of the treatment, resulting in improved efficacy of the desired inhibitor.

The compounds are also useful in the treatment of pulmonary and respiratory inflammation, including, but not limited to, asthma, chronic bronchitis, bronchiolitis, bronchiolitis obliterans (including such with organizing pneumonia), allergic inflammation of the respiratory tract (including rhinitis and sinusitis), eosinophilic granuloma, pneumonias, pulmonary fibroses, pulmonary manifestations of connective tissue diseases, acute or chronic lung injury, chronic obstructive pulmonary diseases, adult respiratory distress syndrome, and other non-infectious inflammatory disorders of the lung characterized by eosinophil infiltration.

For example, the compounds of the invention are useful in the inhibition of: eosinophil-mediated inflammation of the lung or tissues; neutrophil-mediated inflammation of the lung; lymphocyte-mediated inflammation of the lung; cytokine and chemokine production, including interleukin-5, interleukin-13 and eotaxin; lipid mediator generation, including prostaglandin $E_2$ and cysteinyl leukotrienes; airway hyper-responsiveness; and airway and vascular inflammation.

C. Testing of the Compounds of the Invention

A hallmark of inflammation is the adhesion and transmigration across endothelium of neutrophils, eosinophils and other inflammatory cells. A similar process is observed for the migration of cells across polarized epithelial cells that occur in the lung, gastrointestinal tract and other organs. Cell culture models of these processes are available and have been used to show that lipoxin $A_4$ and stable lipoxin $A_4$ analogs inhibit the transmigration of human neutrophils across human endothelial cells and epithelial cells, including the human intestinal epithelial cell line $T_{84}$. Accordingly, one of ordinary skill in the art can test the compounds of the invention for their ability to inhibit the transmigration of human neutrophils and eosinophils across human endothelial cells and epithelial cells by performing assays similar to those described in Colgan, S. P., et al., *J. Clin. Invest.* (1993), Vol. 92, No. 1, pp. 75–82 and Serhan, C. N., et al., *Biochemistry* (1995), Vol. 34, No. 44, pp. 14609–14615.

The air pouch model and/or the mouse zymosan-induced peritonitis model may be used to evaluate the in vivo efficacy of the compounds of the invention in treating an inflammatory response. These are acute experimental models of inflammation characterized by infiltration of inflammatory cells into a localized area. See, e.g., the in vivo assays described in Ajuebor, M. N., et al., *Immunology* (1998), Vol. 95, pp. 625–630; Gronert, K., et al., *Am. J. Pathol.* (2001), Vol. 158, pp. 3–9; Pouliot, M., et al., *Biochemistry* (2000), Vol. 39. pp. 4761–4768; Clish, C. B., et al., *Proc. Natl. Acad. Sci. U.S.A.* (1999), Vol. 96, pp. 8247–8252; and Hachicha, M., et al., *J. Exp. Med.* (1999), Vol. 189, pp. 1923–30.

Animal models (i.e., in vivo assays) may also be utilized to determine the efficacy of the compounds of the invention in treating asthma and related disorders of the pulmonary and respiratory tract, including, but not limited to, asthma. See, e.g., the assays described in De Sanctis, G. T. et al., *Journal of Clinical Investigation* (1999), Vol. 103, pp. 507–515 and Campbell, E. M., et al., *J. Immunol.* (1998), Vol. 161, No. 12, pp. 7047–7053.

D. Administration of the Compounds of the Invention

Administration of a compound of the invention, as a single stereoisomers, a mixture of stereoisomers, or as a racemic mixture of stereoisomers; or as a cyclodextrin clathrate thereof, or as a pharmaceutically acceptable salt thereof, in pure form or in an appropriate pharmaceutical composition, can be carried out via any of the accepted modes of administration or agents for serving similar utilities. Thus, administration can be, for example, orally, nasally, parenterally, pulmonary, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, aerosols, patches, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 0.1% to about 99.9% by weight of a compound(s) of the invention, as a single stereoisomer, a mixture of stereoisomers, or as a racemic mixture of stereoisomers; or as a cyclodextrin clathrate thereof, or as a pharmaceutically acceptable salt thereof, and 99.9% to 1.0% by weight of a suitable pharmaceutical excipient. Preferably, the composition will be about 5% to 75% by weight of a compound(s) of the invention, or as a single stereoisomer, a mixture of stereoisomers, or as a racemic mixture of stereoisomers; or as a cyclodextrin clathrate thereof, or as a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, as a single stereoisomer, a mixture of stereoisomers, or as a racemic mixture of stereoisomers; or as a cyclodextrin clathrate thereof, or as a pharmaceutically acceptable salt thereof, is formed by the incorporation of one or more of the normally employed pharmaceutically acceptable excipient(s), such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof, a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), as a single stereoisomer, a mixture of stereoisomers, or as a racemic mixture of stereoisomers; or as a cyclodextrin clathrate thereof, or as a pharmaceutically acceptable salt thereof, and optional pharmaceutical acceptable adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, as a single stereoisomer, a mixture of stereoisomers, or as a racemic mixture of stereoisomers; or as a cyclodextrin clathrate thereof, or as a pharmaceutically acceptable salt thereof, for treatment of a disease-state characterized by inflammation in accordance with the teachings of this invention.

The compounds of the invention, or their pharmaceutically acceptable salts, are administered in a therapeutically effective amount which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.14 mg to about 14.3 mg/kg of body weight per day of a compound of the invention, as a single stereoisomer, a mixture of stereoisomers, or as a racemic mixture of stereoisomers; or as a cyclodextrin clathrate thereof, or as a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, as a single stereoisomer, a mixture of stereoisomers, or as a racemic mixture of stereoisomers; or as a cyclodextrin clathrate thereof, or as a pharmaceutically acceptable salt thereof, preferably from about 50 mg to about 700 mg per day, and most preferably from about 100 mg to about 500 mg per day.

E. Preferred Embodiments

Of the compounds of the invention as set forth above in the Summary of the Invention, several groups of compounds are particularly preferred.

Accordingly, a preferred group of compounds of the invention are those compounds of formula (I):

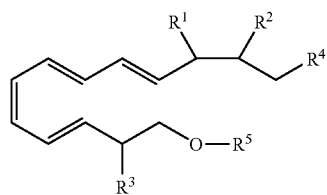

(I)

wherein:
$R^1$, $R^2$ and $R^3$ are each independently halo, —$OR^6$, —$SR^6$ or —$N(R^7)R^8$;
each $R^4$ is —$R^9$—$R^{12}$, —$R^9$—$R^{13}$—$R^{11}$, —$R^9$—O—$R^{10}$—$R^{11}$, —$R^9$—O—$R^{12}$, —$R^9$—C(O)—$R^{10}$—$R^{11}$, —$R^9$—N(R^7)—$R^{10}$—$R^{11}$, —$R^9$—S(O)$_t$—$R^{10}$—$R^{11}$ (where t is 0 to 2), or —$R^9$—C(F)$_2$—$R^9$—$R^{11}$;

$R^5$ is aryl (optionally substituted by one or more substituents selected from the group consisting of alkyl, alkoxy, halo, and haloalkoxy) or aralkyl (optionally substituted by one or more substituents selected from the group consisting of alkyl, alkoxy, halo, and haloalkoxy);
each $R^6$ is independently hydrogen, alkyl, aralkyl, —C(O)$R^7$ or —C(O)O$R^7$;
each $R^7$ is independently hydrogen, alkyl, aryl, or aralkyl;
$R^8$ is independently hydrogen, alkyl, aryl, aralkyl, or cycloalkyl (optionally substituted with one more substituents selected from the group consisting of alkyl, —N($R^7$)$_2$, and —C(O)O$R^7$);
each $R^9$ is independently a direct bond or a straight or branched alkylene chain;
each $R^{10}$ is independently a straight or branched alkylene chain, a straight or branched alkenylene chain, a straight or branched alkynylene chain or a cycloalkylene;
each $R^{11}$ is independently —C(O)O$R^7$ or —C(O)N($R^7$)$_2$;
$R^{12}$ is aryl (substituted by —C(O)O$R^7$ or —C(O)N($R^7$)$_2$ and optionally by one or more substituents selected from the group consisting of alkyl, alkoxy, halo and haloalkoxy) or aralkyl (substituted by —C(O)O$R^7$ or —C(O)N($R^7$)$_2$ and optionally by one or more substituents selected from the group consisting of alkyl, alkoxy, halo and haloalkoxy);
$R^{13}$ is a branched alkylene chain, a straight or branched alkenylene chain or a cycloalkylene.

Of this group of compounds, a preferred subgroup of compounds is that subgroup of compounds wherein:
$R^1$, $R^2$ and $R^3$ are each independently halo, —$OR^6$, or —$SR^6$;
$R^4$ is —$R^9$—O—$R^{10}$—$R^{11}$;
$R^5$ is aryl (optionally substituted by one or more substituents selected from the group consisting of alkyl, alkoxy, halo, and haloalkoxy) or aralkyl (optionally substituted by one or more substituents selected from the group consisting of alkyl, alkoxy, halo, and haloalkoxy);
each $R^6$ is independently hydrogen, alkyl aryl, or aralkyl;
each $R^7$ is independently hydrogen, alkyl, aryl, or aralkyl;
$R^9$ is a direct bond or a straight or branched alkylene chain;
$R^{10}$ is an straight or branched alkylene chain, a straight or branched alkenylene chain, a straight or branched alkynylene chain or a cycloalkylene; and
$R^{11}$ is —C(O)O$R^7$ or —C(O)N($R^7$)$_2$.

Of this subgroup of compounds, a preferred class of compounds is that class of compounds wherein:
$R^1$, $R^2$ and $R^3$ are each —$OR^6$;
$R^4$ is —$R^9$—O—$R^{10}$—$R^{11}$;
$R^5$ is aryl (optionally substituted by one or more substituents selected from the group consisting of alkyl, alkoxy, halo, and haloalkoxy);
$R^6$ is hydrogen, alkyl, aryl, or aralkyl;
each $R^7$ is independently hydrogen, alkyl, aryl, or aralkyl;
$R^9$ is a direct bond;
$R^{10}$ is a straight or branched alkylene chain, a straight or branched alkenylene chain, or a straight or branched alkynylene chain; and
$R^{11}$ is —C(O)O$R^7$ or —C(O)N($R^7$)$_2$.

Of this class of compounds, preferred compounds are selected from the group consisting of the following compounds:
(5S,6R,7E,9E,11Z,13E,15S)-16-(4-fluorophenoxy)-5,6,15-trihydroxy-3-oxa-7,9,11,13-hexadecatetraenoic acid, methyl ester; and
(5S,6R,7E,9E,11Z,13E,15S)-16-(4-fluorophenoxy)-5,6,15-trihydroxy-3-oxa-7,9,11,13-hexadecatetraenoic acid.

Another preferred group of compounds of the invention is that group of compounds of formula (II):

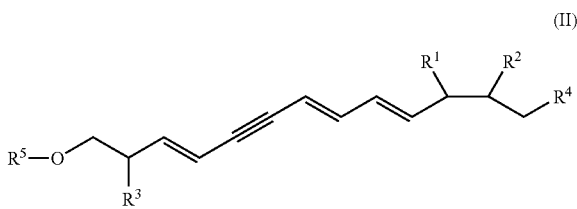

(II)

wherein:

$R^1$, $R^2$ and $R^3$ are each independently halo, —$OR^6$, —$SR^6$ or —$N(R^7)R^8$;

each $R^4$ is —$R^9$—$R^{12}$, —$R^9$—$R^{13}$—$R^{11}$, —$R^9$—O—$R^{10}$—$R^{11}$, —$R^9$—O—$R^{12}$, —$R^9$—C(O)—$R^{10}$—$R^{11}$, —$R^9$—$N(R7)$—$R^{10}$—$R^{11}$, —$R^9$—$S(O)_t$—$R^{10}$—$R^{11}$ (where t is 0 to 2), or —$R^9$—$C(F)_2$—$R^9$—$R^{11}$;

$R^5$ is aryl (optionally substituted by one or more substituents selected from the group consisting of alkyl, alkoxy, halo, and haloalkoxy) or aralkyl (optionally substituted by one or more substituents selected from the group consisting of alkyl, alkoxy, halo, and haloalkoxy);

each $R^6$ is independently hydrogen, alkyl, aralkyl, —C(O)$R^7$ or —C(O)O$R^7$;

each $R^7$ is independently hydrogen, alkyl, aryl, or aralkyl;

$R^8$ is independently hydrogen, alkyl, aryl, aralkyl, or cycloalkyl (optionally substituted with one more substituents selected from the group consisting of alkyl, —$N(R^7)_2$, and —C(O)O$R^7$);

each $R^9$ is independently a direct bond or a straight or branched alkylene chain;

each $R^{10}$ is independently a straight or branched alkylene chain, a straight or branched alkenylene chain, a straight or branched alkynylene chain or a cycloalkylene;

each $R^{11}$ is independently —C(O)O$R^7$ or —C(O)$N(R^7)_2$;

$R^{12}$ is aryl (substituted by —C(O)O$R^7$ or —C(O)$N(R^7)_2$ and optionally by one or more substituents selected from the group consisting of alkyl, alkoxy, halo and haloalkoxy) or aralkyl (substituted by —C(O)O$R^7$ or —C(O)$N(R^7)_2$ and optionally by one or more substituents selected from the group consisting of alkyl, alkoxy, halo and haloalkoxy);

$R^{13}$ is a branched alkylene chain, a straight or branched alkenylene chain or a cycloalkylene.

Of this group of compounds, a preferred subgroup of compounds is that subgroup of compounds wherein:

$R^1$, $R^2$ and $R^3$ are each independently halo, —$OR^6$, or —$SR^6$;

$R^4$ is —$R^9$—O—$R^{10}$—$R^{11}$;

$R^5$ is aryl (optionally substituted by one or more substituents selected from the group consisting of alkyl, alkoxy, halo, and haloalkoxy) or aralkyl (optionally substituted by one or more substituents selected from the group consisting of alkyl, alkoxy, halo, and haloalkoxy);

each $R^6$ is independently hydrogen, alkyl, aryl, or aralkyl;

each $R^7$ is independently hydrogen, alkyl, aryl, or aralkyl;

$R^9$ is a direct bond or a straight or branched alkylene chain;

$R^{10}$ is an straight or branched alkylene chain, a straight or branched alkenylene chain, a straight or branched alkynylene chain or a cycloalkylene; and $R^{11}$ is —C(O)O$R^7$ or —C(O)$N(R^7)_2$.

Of this subgroup of compounds, a preferred class of compounds is that class of compounds wherein:

$R^1$, $R^2$ and $R^3$ are each —$OR^6$;

$R^4$ is —$R^9$—O—$R^{10}$—$R^{11}$;

$R^5$ is aryl (optionally substituted by one or more substituents selected from the group consisting of alkyl, alkoxy, halo, and haloalkoxy);

$R^6$ is hydrogen, alkyl, aryl, or aralkyl;

each $R^7$ is independently hydrogen, alkyl, aryl, or aralkyl;

$R^9$ is a direct bond;

$R^{10}$ is a straight or branched alkylene chain, a straight or branched alkenylene chain, or a straight or branched alkynylene chain; and $R^{11}$ is —C(O)O$R^7$ or —C(O)$N(R^7)_2$.

Of this class of compounds, preferred compounds are selected from the group consisting of the following compounds:

(5S,6R,7E,9E,13E,15S)-16-(4-fluorophenoxy)-5,6,15-trihydroxy-3-oxahexadeca-7,9,13-trien-11-ynoic acid, methyl ester;

(5S,6R,7E,9E,13E,15S)-16-(4-fluorophenoxy)-5,6,15-trihydroxy-3-oxahexadeca-7,9,13-trien-11-ynoic acid;

(5S,6S,7E,9E,13E,15S)-16-(4-fluorophenoxy)-5,6,15-trihydroxy-3-oxahexadeca-7,9,13-trien-11-ynoic acid, methyl ester; and (5S,6S,7E,9E,13E,15S)-16-(4-fluorophenoxy)-5,6,15-trihydroxy-3-oxahexadeca-7,9,13-trien-11-ynoic acid.

Of the methods of using the compounds of the invention as set forth above in the Summary of the Invention, a preferred use of the compounds is the treatment of psoriasis, atopic dermatitis, multiple sclerosis or acute hemorrhagic or ischemic stroke in humans. Another preferred use of the compounds is the treatment of asthma in humans.

F. Preparation of the Compounds of the Invention

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (e.g., t-butyldimethylsilyl, t-butyldiphenylsilyl or trimethylsilyl), tetrahydropyranyl, benzyl, and the like. Suitable protecting groups for 1,2-dihydroxys include ketal- and acetal-forming groups. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, Protective Groups in Organic Synthesis (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of formula (I) and formula (II), as described above in the Summary of the Invention, may not possess pharmacological activity as such, they may be administered to a mammal having an inflammatory or autoimmune disorder, or a pulmonary and respiratory tract inflammation, and thereafter metabolized in the body to form compounds of the invention which are pharmacologically active. Such derivatives may therefore be described as "prodrugs". All prodrugs of compounds of formula (I) and (II) are included within the scope of the invention.

For convenience purposes, only compounds of the invention wherein $R^9$ is a bond and $R^1$, $R^2$, and $R^3$ are hydroxy are depicted in the following Reaction Schemes. It is also understood, however, that one of ordinary skill in the art would be able to make the other compounds of the invention in light of the following disclosure, including the Preparations and Examples, and information known to those of ordinary skill in the chemical synthesis field.

1. Preparation of Compounds of Formula (D)

Compounds of formula (D) are intermediates in the preparation of the invention. They are prepared as described below in Reaction Scheme 1:

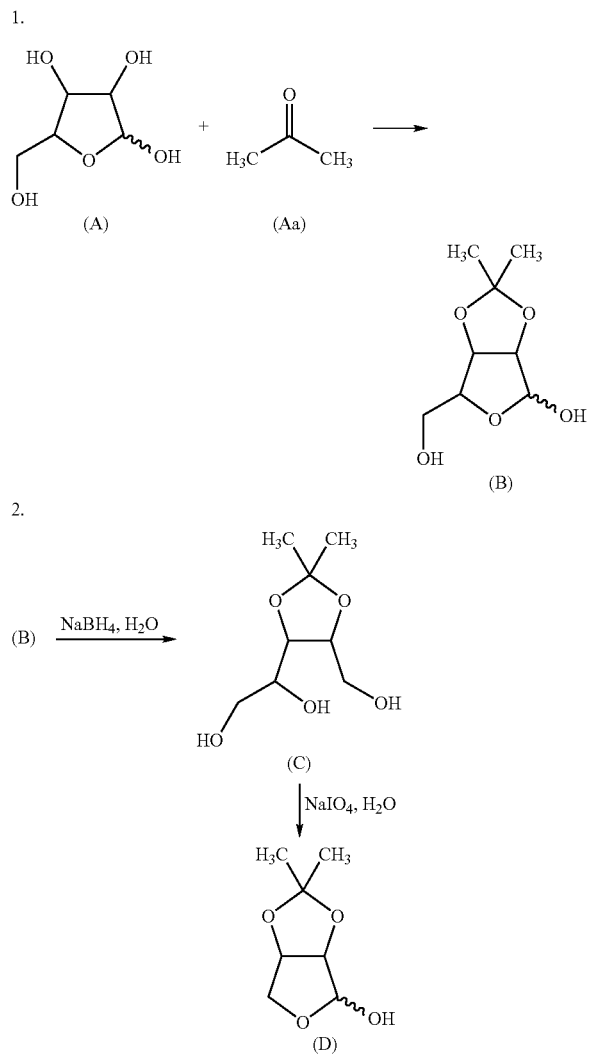

Compounds of formula (A) and formula (Aa) are commercially available or may be prepared according to methods known to those of ordinary skill in the art.

In general, compounds of formula (D) are prepared by first treating a compound of formula (A) with a ketone of formula (Aa) in the presence of an acid, preferably sulfuric acid, at ambient temperature for about 30 minutes to about 2 hours, preferably for about 1.5 hours. The pH of the resulting reaction mixture is then adjusted to about pH 7.0 with an appropriate base. The compound of formula (B) is then isolated from the reaction mixture by standard isolation techniques, such as filtration and concentration.

The compound of formula (B) in a protic solvent, preferably water, is then treated with an appropriate reducing agent, preferably sodium borohydride, at temperatures between about 0° C. and 5° C. The reaction mixture is stirred for about 1 hour to about 2 hours, preferably for about 2 hours, before a mild acid is added to consume the excess reducing agent present and to adjust the pH to about pH 6.0. The resulting reaction mixture is cooled to between about 0° C. and 5° C. A glycol cleaving agent, such as sodium periodate, is then added to the mixture. The resulting reaction mixture is stirred at ambient temperature for about 1 hour to about 2 hours, preferably for about 2 hours. The compound of formula (D) is then isolated from the reaction mixture by standard isolation techniques, such as organic extraction and concentration.

Alternatively, other alkyl, aryl and aralkyl ketones may be used instead of the ketone of formula (Aa) to form the ketal of formula (B). In addition, an appropriate aldehyde may be used intead of the ketone of formula (Aa) to form the corresponding acetal, which may be further treated as described herein to form the compound of formula (D). For a description of various protecting groups for 1,2-diols, see Green, T. W. and P. G. M. Wutz, Protective Groups in Organic Synthesis (1991), 2nd Ed., Wiley-Interscience.

2. Preparation of Compounds of Formula (M)

Compounds of formula (M) are intermediates in the preparation of compounds of the invention. They are prepared as described below in Reaction Scheme 2 wherein $R^{7a}$ is alkyl, aryl or aralkyl, $R^{10}$ is as described above in the Summary of the Invention, each $R^{14}$ is independently hydrogen or alkyl, $R^{14a}$ is hydrogen or alkyl, and $X_1$ and $X_2$ are each independently halo:

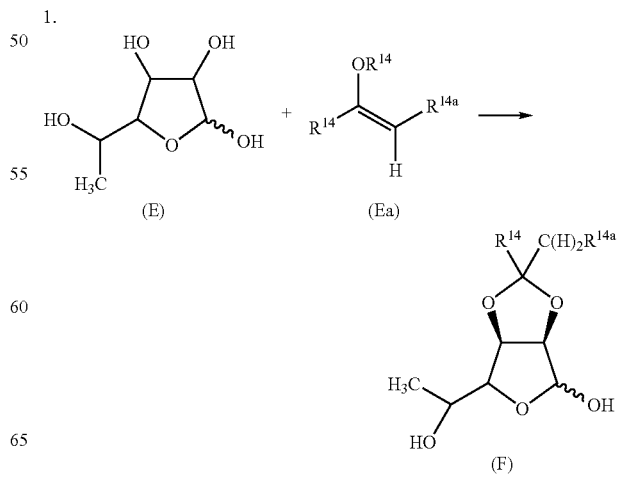

2.

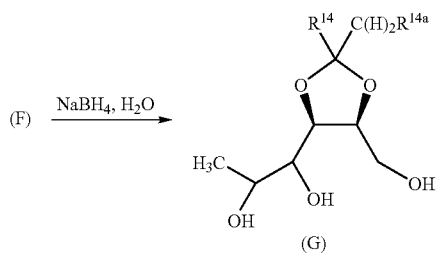

3.

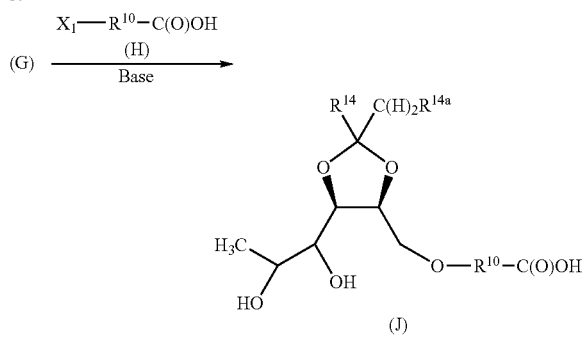

4.

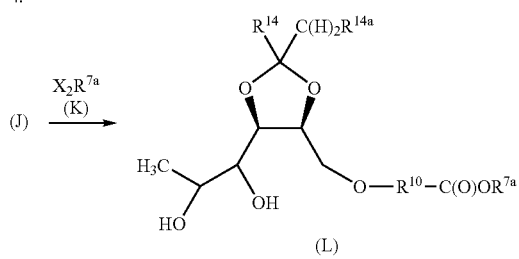

5.

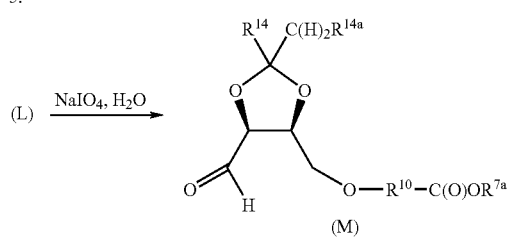

Compounds of formula (E), formula (Ee), formula (H) and formula (K) are commercially available, or may be prepared according to methods known to those skilled in the art.

In general, compounds of formula (M) are prepared by first removing water, if needed, from the compound of formula (E) by standard techniques. The compound of formula (E), in an aprotic anhydrous solvent, such as acetone when each $R^{14}$ is methyl and $R^{14a}$ is hydrogen, is then treated with a compound of formula (Ea) in the presence of an acid catalyst, such as dl-10-camphorsulfonic acid, at ambient temperature. The reaction mixture is stirred for about 2 hours to about 4 hours, preferably for about 3 hours, and then made basic by the addition of a base, such as ammonia gas. The compound of formula (F) is then isolated from the reaction mixture by standard isolation techniques, such as filtration, concentration, organic extraction and concentration.

An aqueous solution of the compound of formula (F) is then treated with a reducing agent, preferably cold sodium borohydride in water. The resulting reaction mixture is stirred for about 3 hours to about 6 hours, preferaby for about 5 hours, and then treated with an acid, preferably acetic acid, to remove excess borohydride and to adjust the pH to about 6.0. The compound of formula (G) is isolated from the reaction mixture by standard techniques, such as extraction of the aqueous layer and concentration thereof.

The compound of formula (G) is then treated with a compound of formula (H) in the presence of a base, preferably sodium hydroxide. The reaction mixture is stirred for about 6 hours to about 24 hours, preferably for about 12 hours. The compound of formula (J) is isolated from the reaction mixture by standard isolation techniques and dissolved in an aprotic solvent, preferably dimethylformamide (DMF). A compound of formula (K) is then added to the solution, and the resulting mixture is stirred for about 6 hours to about 24 hours, preferably for about 12 hours. The compound of formula (L) is then isolated from the reaction mixture by standard isolation techniques, such as salt wash, extraction and concentration.

The compound of formula (L) in water and a polar aprotic co-solvent, such as acetone, is treated with a glycol cleaving agent, such as sodium periodate. The compound of formula (M) was isolated from the reaction mixture by standard isolation techniques, such as extraction, salt wash and concentration.

3. Preparation of Compounds of Formula (Q)

Compounds of formula (Q) are intermediates in the preparation of the compounds of the invention. They are prepared as described below in Reaction Scheme 3 wherein Ph is phenyl and $PG_1$ is a protecting group for the triple bond, e.g., phenyldimethylsilyl, diphenylmethylsilyl, or trimethylsilyl:

REACTION SCHEME 3

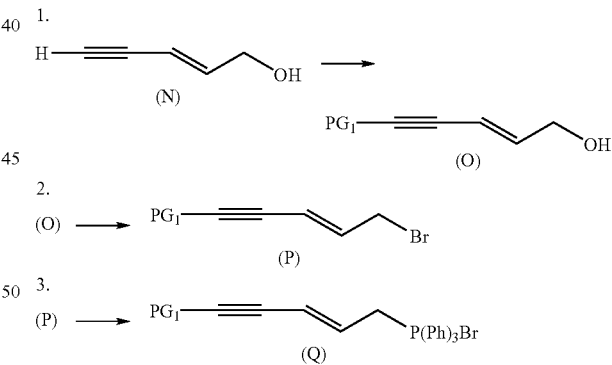

The compound of formula (N) is commercially available are may be prepared according to methods known to those skilled in the art.

In general, the Wittig reagent of formula (Q) is prepared by first dehydrogenating the compound of formula (N) by treatment with an organometallic compound, preferably n-butyllithium, at temperatures of between –30° C. and –15° C., preferably at about –20° C. A protecting group, preferably trimethylsilyl, is then added to the compound under standard protecting group generation conditions. The protected compound of formula (O) is isolated from the reaction mixture by standard isolation techniques, such as extraction of the organic layers and concentration.

The compound of formula (O) in an aprotic solvent, preferably dicloromethane, is then treated with a brominating agent, such as N-bromosuccinimide, in the presence of triphenylphosphine at temperatures of between about −10° C. and about 0° C. The reaction mixture is allowed to warm to ambient temperature and stirred for about 1 hour to about 3 hours, preferably for about 2 hours. The compound of formula (P) is isolated from the rection mixture by standard isolation techniques, such as concentration and trituration with an inert organic solvent, such as hexane.

The compound of formula (P) is then treated with a slight excess of molar amount of a triarylphosphine or trialkylphosphine, preferably triphenylphosphine, under standard Wittig reagent forming conditions to form the phosphorus ylide of formula (Q) (the Wittig reaction reagent).

4. Preparation of Compounds of Formula (W)

Compounds of formula (W) are intermediates in the preparation of the compounds of the invention. They are prepared as described below in Reaction Scheme 4 wherein $PG_1$ is a protecting group, $X_1$ is a halo, $R^{10}$ is as described above in the Summary of the Invention, and $R^{7a}$ and $R^{7b}$ are each independently alkyl, aryl or aralkyl:

REACTION SCHEME 4

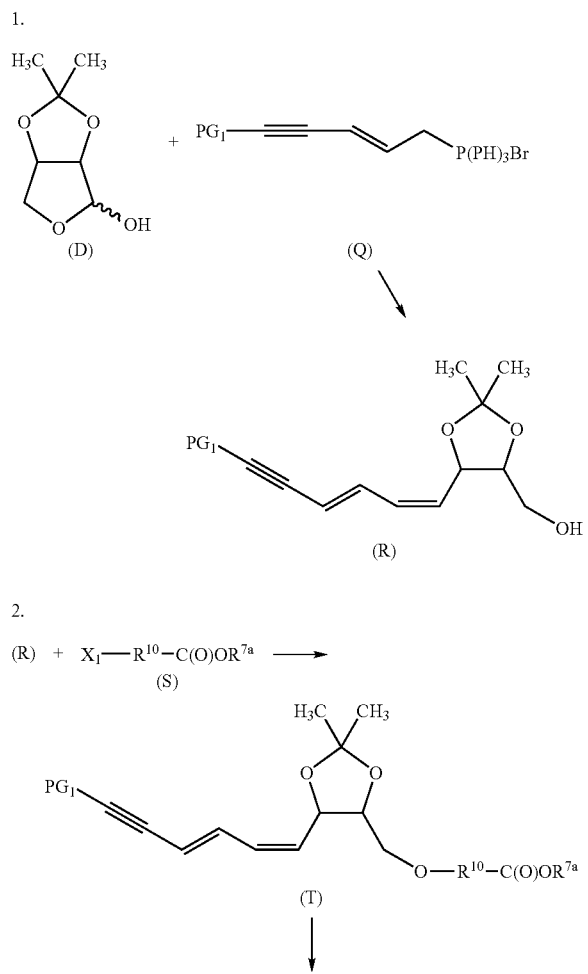

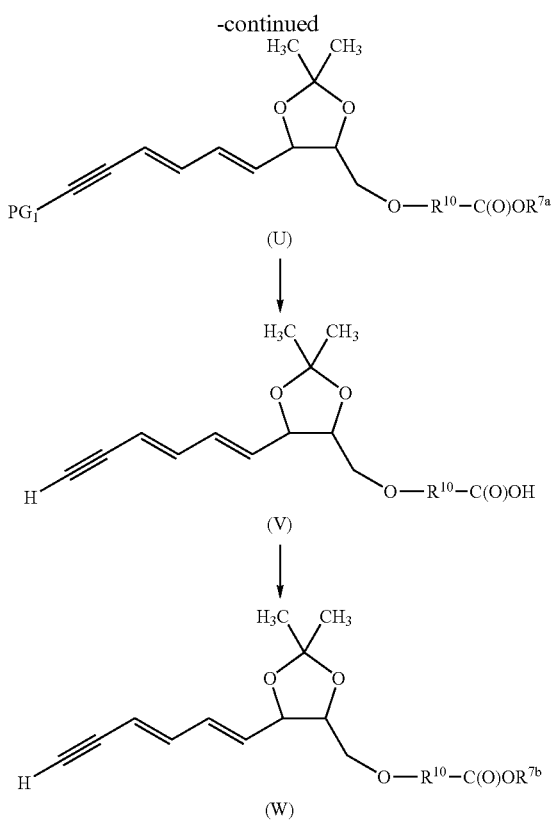

Compounds of formula (D) and formula (Q) are prepared by methods disclosed herein. Compounds of formula (S) are commercially available, or may be prepared according to methods known to those skilled in the art.

In general, compounds of formula (W) are prepared by first treating a compound of formula (D) with a slightly excess molar amount of a compound of formula (Q) under standard Wittig reaction conditions to form a compound of formula (R), which is isolated from the reaction mixture by standard isolation techniques.

The compound of formula (R) is then treated with a compound of formula (S) in an aprotic solvent, such as tetrahydrofuran (THF) in the presence of a strong base, such as sodium hydroxide, and at a temperature of about 50° C. to about 70° C., preferably at about 63° C. The reaction mixture is allowed to cool to ambient temperature. The compound of formula (T) was isolated from the reaction mixture by standard isolation techniques such as organic extraction and concentration.

The compound of formula (T) in an aprotic solvent, such as methylene chloride, is treated with elemental iodine at ambient temperature under standard conditions. The geometric isomer of formula (U) is isolated from the reaction mixture by standard isolation techniques.

The compound of formula (U) in an aprotic solvent, such as THF, is then deprotected and hydrolyzed to the compound of formula (V) under standard de-protection and hydrolysis conditions. The compound of formula (V) is isolated from the reaction mixture by standard isolation techniques, such as extraction and concentration.

The compound of formula (V) in an aprotic solvent is then treated with an esterifying agent, such as trimethylsilyldiazomethane, under standard esterification conditions to form the compound of formula (W), which is isolated from the reaction mixture by standard isolation techniques, such as extraction, concentration and purification by chromatography.

5. Preparation of Compounds of Formula (Ta) and Formula (Ua)

Compounds of formula (Ta) and formula (Ua) are intermediates in the preparation of the compounds of the invention and may be prepared as described below in Reaction Scheme 5 wherein $R^{7a}$ is alkyl, aryl or aralkyl, $R^{10}$ is as described above in the Summary of the Invention, $R^{14}$ is alkyl and $R^{14a}$ is hydrogen or alkyl:

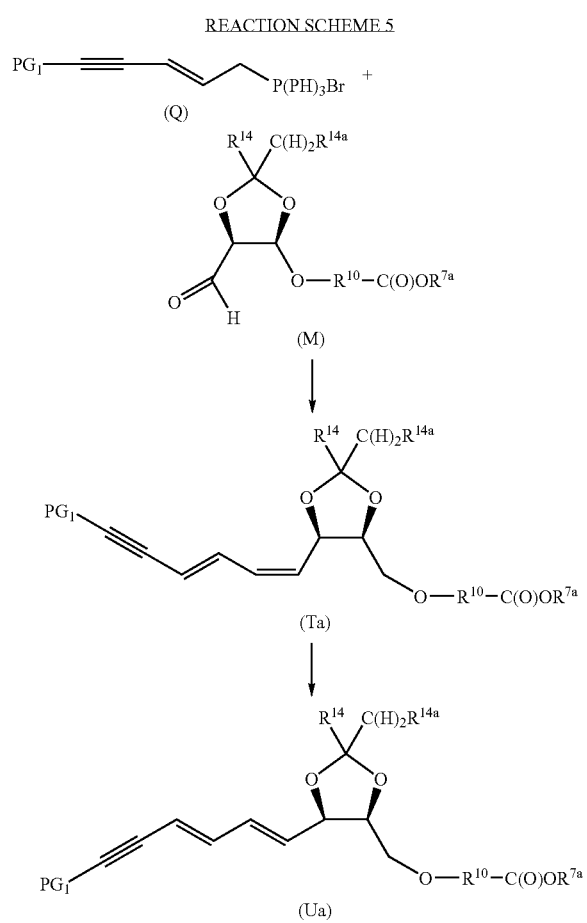

Compounds of formula (Q) and formula (M) are prepared according to methods disclosed herein.

In general, compounds of formula (Ua) are prepared by first treating a compound of formula (M) with a slightly excess molar amount of a compound of formula (Q) under standard Wittig reaction conditions to form a compound of formula (Ta), which is then treated with elemental iodine under similar conditions as described above to form compounds of formula (Ua). The compound of formula (Ua) is then treated in a similar manner as described above for the compounds of formula (U) to form the corresponding compound of formula (W) as described above.

6. Preparation of Compounds of Formula (DD)

Compounds of formula (DD) are intermediates in the preparation of the compounds of the invention. They are prepared as described below in Reaction Scheme 6 wherein $R^5$ is as described above in the Summary of the Invention, and $X_2$ is halo:

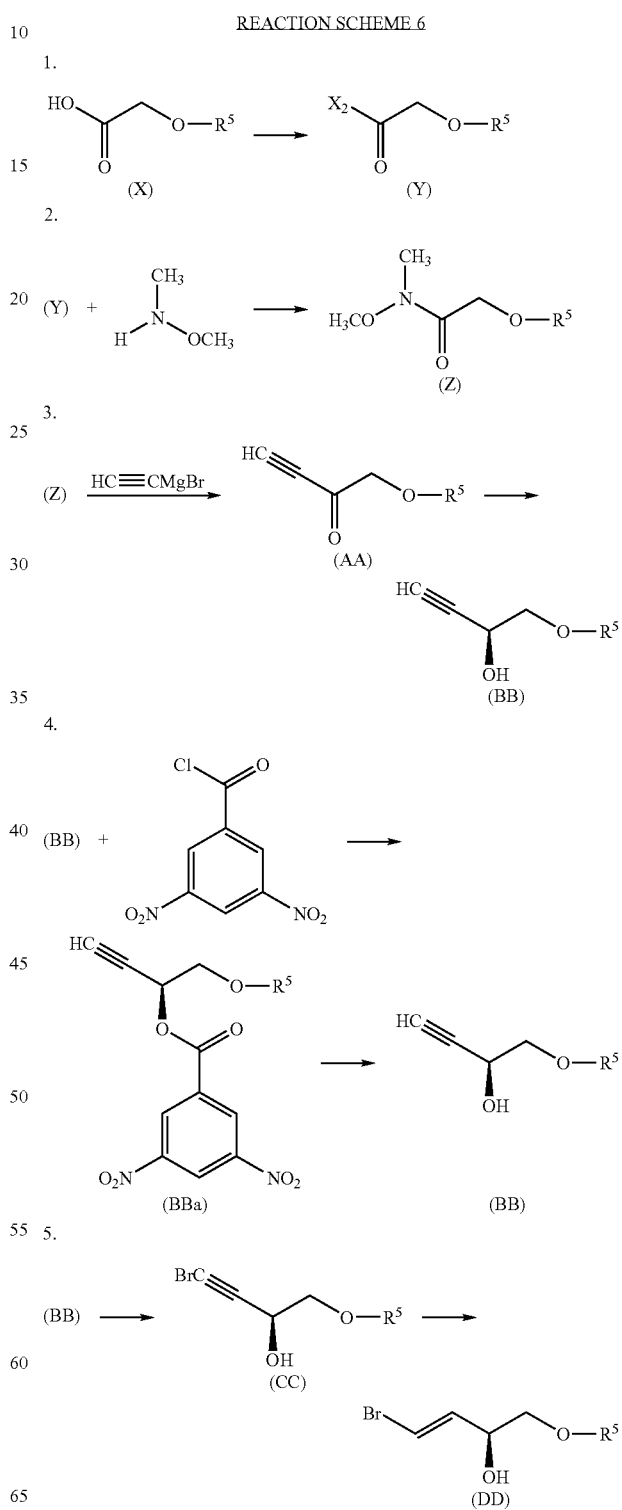

Compounds of formula (X), N,O-dimethylhydroxylamine, ethynylmagnesium bromide and 3,5-dinitrobenzoyl chloride are commercially available, or may be prepared according to methods known to those skilled in the art.

In general, compounds of formula (DD) are prepared by first treating a compound of formula (X) in an aprotic solvent, preferably methylene chloride, with an excess molar amount of an acyl halide reagent, preferably oxalyl chloride, at ambient temperature. The reaction mixture is allowed to stir for about 6 hours to about 24 hours, preferably for about 12 hours. The compound of formula (Y) is isolated from the reaction mixture by standard isolation techniques, such as concentration in vacuo.

The compound of formula (Y) is then treated with an hydroxylamine, preferably, N,O-dimethylhydroxylamine or a 1,2-oxazolidine, in the presence of an alkaline base, potassium carbonate, under standard amine acylation conditions. The compound of formula (Z) is isolated from the reaction mixture by standard isolation techniques, such as organic extraction and concentraiton.

The compound of formula (Z) in an aprotic solvent, preferably THF, is then treated with the appropriate Grignard reagent, such as HC≡CMgBr under standard conditions to form a compound of formula (AA), which is isolated from the reaction mixture by standard isolation techniques, such as organic solvent extraction, filtration and concentration. The compound of formula (AA) is then treated with a chiral reducing agent under standard reducing conditions to form a compound of formula (BB), which is isolated from the reaction mixture by standard isolation techniques, such as filtration, concentration and purification by flash chromatography, as a mixture of enantiomers. The enantiomeric excess can be determined by chiral analytical HPLC.

The enantiomeric excess is improved by recrystallization of an aryl ester formed by treating the compound of formula (BB) in an aprotic solvent, preferably methylene chloride, with an excess molar amount of an aroyl halide, preferably 3,5-dinitrobenzoyl chloride, at a temperature of between about −5° C. and 0° C., in the presence of a base, preferably triethylamine, and an activating amount of dimethylaminopyridine (DMAP). The reaction mixture is stirred at ambient temperature for about 30 minutes to 1 hour, preferably for 40 minutes. The compound of formula (BBa) is isolated from the reaction mixture by standard isolation techniques, such as extraction, filtration and recrystallization and is determined to have greater than 98% enantiomeric excess by analytical HPLC.

The compound of formula (BBa) in a protic solvent, preferably methanol, is treated with an alkaline base, preferably potassium carbonate. The reaction mixture is stirred for about 3 hours to about 5 hours, preferably for about 3.5 hours and the reaction is then quenched by the addition of acid, preferably acetic acid. The compound of formula (BB) having a 98% enantiomeric excess is isolated from the reaction mixture by standard isolation techniques, such as filtration and concentration of the filtrate.

The compound of formula (BB) is then treated with a halogenating agent, preferably N-bromosuccinimide, in the presence of a catalyst, such as silver nitrate, at ambient temperature. The compound of formula (CC) is then isolated from the reaction mixture by standard isolation techniques, such as concentration in vacuo, filtration and elution with organic solvents.

The compound of formula (CC) is then hydrogenated under standard hydrogenation conditions for triple bonds, such as treatment with a reducing agent, preferably a mixture of lithium aluminum hydride and aluminum chloride, to form a compound of formula (DD), which is isolated from the reaction mixture by standard isolation techniques.

7. Preparation of Compounds of Formula (Ia), Formula (Ib) and Formula (IIa)

Compounds of formula (Ia), formula (Ib) and formula (IIa) are compounds of the invention. They are prepared as described below in Reaction Scheme 7 wherein $R^5$ and $R^{10}$ are as described above in the Summary of the Invention and $R^{7b}$ is alkyl, aryl or aralkyl:

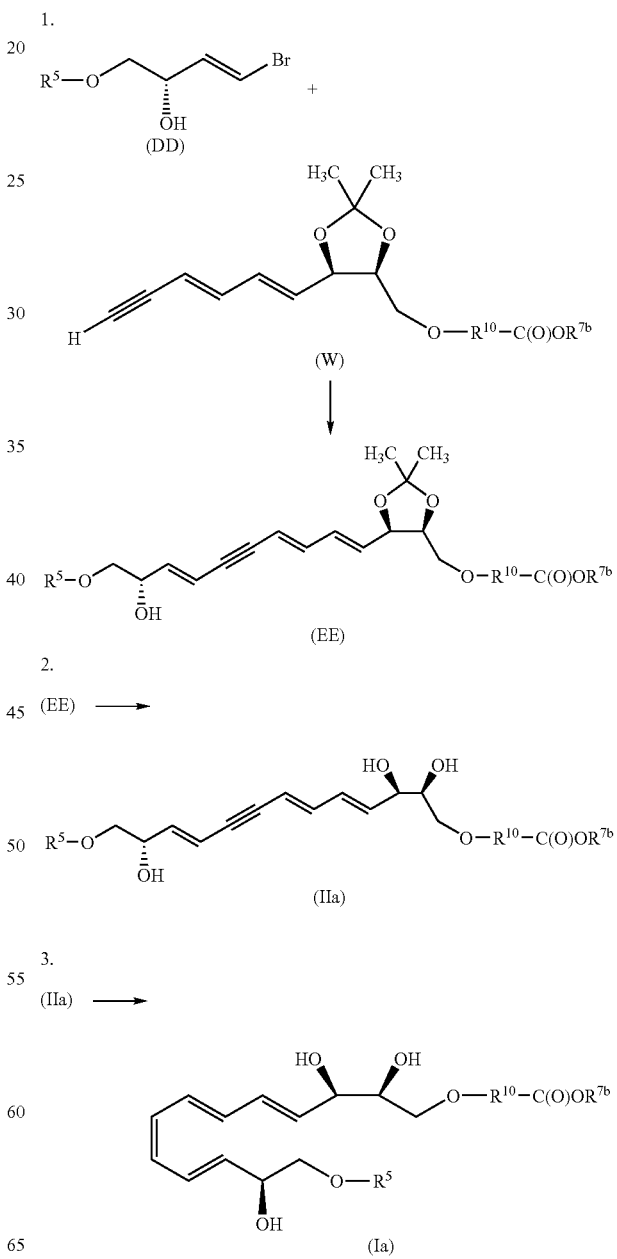

-continued

4.

(Ia) →

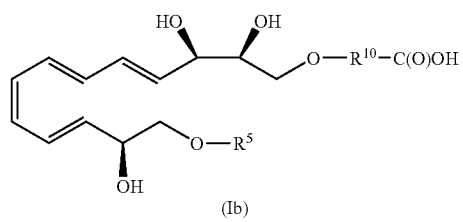
(Ib)

Compounds of formula (DD) and formula (W) are prepared by methods disclosed herein. Alternatively, compounds corresponding to compounds of formula (W) which are made from compounds of formula (Ua) may be used in the above reaction scheme to produce corresponding compounds of the invention.

In general, compounds of formula (Ia), formula (Ib) and formula (IIa) are prepared by first treating a compound of formula (DD) in an aprotic solvent, preferably THF, with a compound of formula (W) in an aprotic solvent, preferably THF, under standard Sonogashira coupling conditions, such as in the presence of copper iodide, an amine base and a palladium catalyst. The reaction mixture is stirred at ambient temperature for about 30 minutes to about 1 hour, preferably for about 45 minutes. The compound of formula (EE) is isolated from the reaction mixture by standard isolation techniques, such as filtration, elution with organic solvent and purification by chromatography.

The compound of formula (EE) in a protic solvent, preferably methanol, is then treated with an acid, preferably hydrochloric acid. The reaction mixture is stirred at ambient temperature for about 12 hours to about 48 hours, preferably for about 48 hours. The compound of formula (IIa) is isolated from the reaction mixture by standard isolation techniques, such as adjusting the pH of the reaction mixture to pH 7.0 and purification by reverse phase chromatography.

Compounds of formula (IIa) in a protic solvent, preferably methanol, is then reduced to a compound of formula (Ia) by the method described in *Helv. Chim. Acta.* (1987). The compound of formula (Ia) is then hydrolyzed to a compound of formula (Ib) under standard basic hydrolysis conditions.

In addition, compounds of formula (IIa) in a protic solvent, preferably methanol, may then be hydrolyzed under standard basic hydrolysis conditions to form compounds of formula (IIa) herein $R^{7b}$ is hydrogen.

8. Preparation of Compounds of Formula (IIb)

Compounds of formula (IIb) are compounds of the invention. They are prepared as described below in Reaction Scheme 8 wherein q, p, $R^5$, $R^{10}$, and $R^{15}$ are as described above in the Summary of the Invention and $R^{7b}$ is alkyl, aryl or aralkyl:

REACTION SCHEME 8

1.

(E) + (FF) →

(GG)

2.

(GG) $\xrightarrow{\text{NaBH}_4, \text{H}_2\text{O}}$ (HH)

3.

(HH) + $X_1-R^{10}-C(O)OR^{7b}$ →
(Sa)

(JJ)

4.

(JJ) $\xrightarrow{\text{NaIO}_4, \text{H}_2\text{O}}$ (KK)

-continued

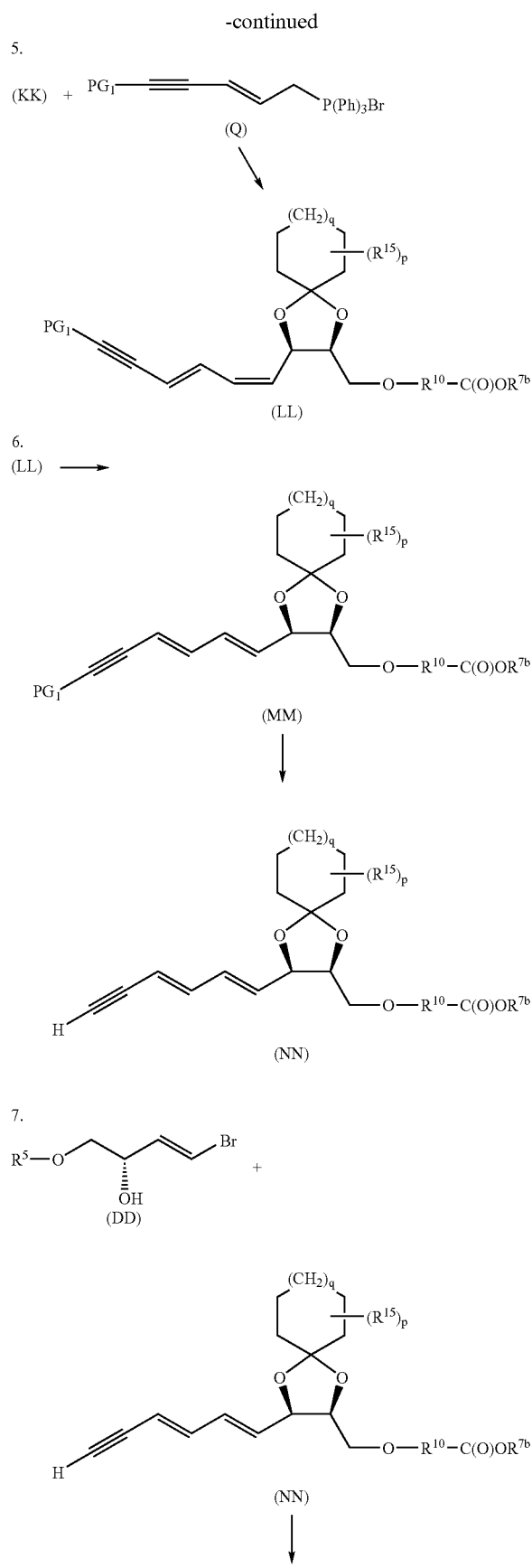

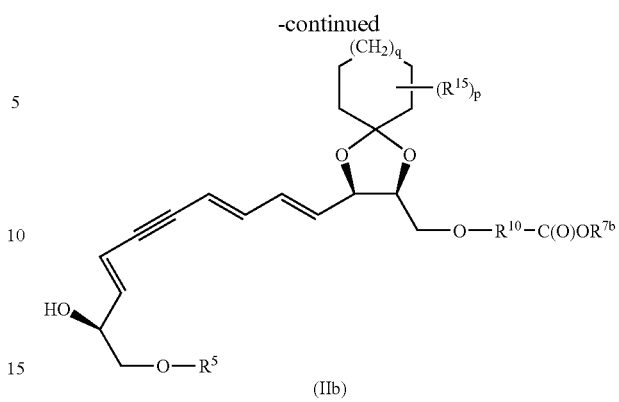

Compounds of formulae (E), (FF), (O), and (Sa) are commercially available or may be prepared according to methods disclosed herein or by methods known to one of ordinary skill in the art.

In general, the compounds of formula (IIb) are prepared by first stirring a mixture of a compound of formula (E) and copper sulfate in a compound of formula (FF) under nitrogen while a strong acid, such as sulfuric acid, is added to the reaction mixture. The resulting reaction mixture is warmed to ambient temperature, preferably to about 29° C., and allowed to stir for a period of between about 8 hours and 16 hours, preferably for about 12 hours. The reaction mixture is filtered and the resulting filtrate is washed with an organic solvent, preferably ethyl acetate. The filtrate is then treated with a base, preferably ammonium hydroxide, and the resulting solid is removed by filtration. The compound of formula (GG) is isolated from the filtrate by standard isolation techniques, such as extraction by organic solvents and further filtration.

An excess molar amount of a reducing agent, such as sodium borohydride, in a protic solvent, such as methanol, is then cooled to about 0° C. and then treated with a compound of formula (GG) in a protic solvent, such as methanol. The resulting reaction mixture is allowed to stir for between about 4 hours to about 8 hours, preferably for about 4 hours. Upon completion of the desired reaction, an acid, preferably acetic acid, is then added to the reaction mixture to consume the excess reducing agent and to adjust the pH of the reaction mixture to about pH 6. The compound of formula (HH) is then isolated from the reaction mixture by standard isolation techniques, such as filtration, concentration of the solids, extraction by organic solvent, and precipitation.

A mixture of a compound of formula (HH) and a compound of formula (Sa) in an aprotic solvent, such as toluene is then stirred as a alkaline base, such as sodium hydroxide in water, is added. A phase transfer catalyst, such as tetrabutylammonium sulfate, is added to the reaction mixture and the reaction mixture is stirred for a period of about between 8 hours and 16 hours, preferably for about 12 hours. The compound of formula (JJ) is isolated from the reaction mixture by standard isolation techniques, such as extraction by basic organic solvents, concentration, and chromatography.

The compound of formula (JJ) in a polar organic solvent, such as acetone, is then treated with an excess molar amount of periodate in water. The resulting reaction mixture is then stirred vigorously under nitrogen for a period of from about 4 hours to about 8 hours, preferably for about 4 hours. The solvent is removed in vacuo at ambient temperature. The compound of formula (KK) is isolated from the reaction mixture by standard isolation techniques, such as extraction by organic solvent and concentration of organic layers.

A compound of formula (Q) in an aprotic solvent, preferably THF is cooled to about −30° C. under anhydrous conditions and then treated gradually with a strong base, preferably n-butyllithium. The reaction mixture is allowed to warm to about 0° C. and stirred for a period of between about 15 minutes and 1 hour, preferably for about 15 minutes. The reaction mixture is then cooled to about −30° C. and then treated with an equimolar amount of a compound of formula (KK) in an aprotic solvent, preferably THF. The resulting reaction mixture is stirred for a period of between about 30 minutes to 2 hours, preferably for about 1 hour at a temperature of about −30° C. The reaction was quenched by the addition of an appropriate acid, such as potassium phosphate. The compound of formula (LL) is isolated from the reaction mixture by standard isolation techniques, such as salt wash, concentration, and precipitation.

The compound of formula (LL) is treated in a manner similar to the treatment of the compound of formula (T) in Reaction Scheme 4 above to afford a compound of formula (MM), which is then treated in a manner similar to the treatment of the compound of formula (U) in Reaction Scheme 4 above to afford a compound of formula (NN).

Compounds of formula (NN) are then treated with a compound of formula (DD) in a manner similar to that described for the treatment of compounds of formula (W) in Reaction Scheme 7 above to afford a compound of formula (IIb).

9. Preparation of Compounds of Formulae (IIc) and (IId)

Compounds of formulae (IIc) and (IId) are the same as compounds of formula (IIa) described above, except that the starting material from which they are prepared, i.e., compound of formula (IIb), is prepared by a different synthesis than the starting material for compounds of formula (IIa). Accordingly, the compounds of formulae (IIc) and (IId) are prepared as described below in Reaction Scheme 9 wherein q, p, $R^5$, $R^{10}$, and $R^{15}$ are as described above in the Summary of the Invention and $R^{7b}$ is alkyl, aryl or aralkyl:

REACTION SCHEME 9

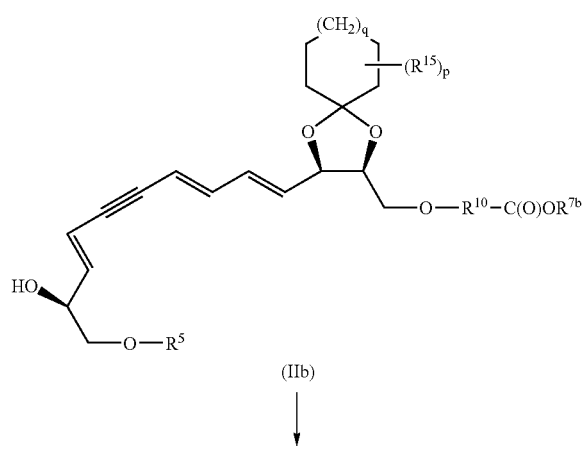

(IIb)

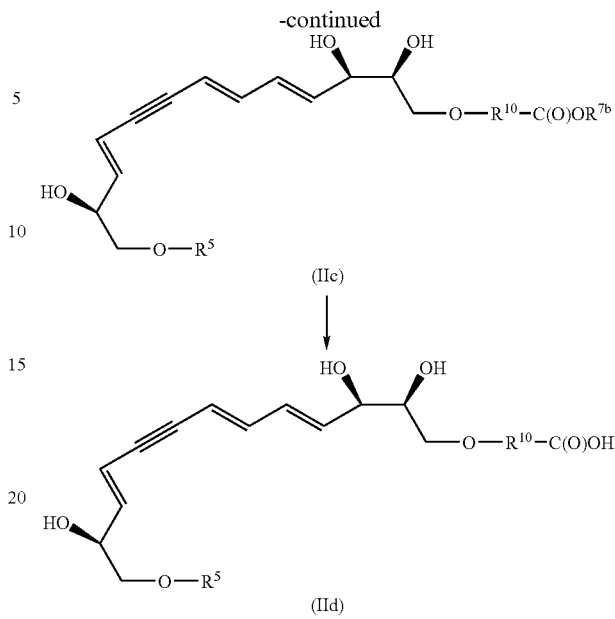

Compounds of formula (IIb) are prepared as described above in Reaction Scheme 8.

In general, compounds of formula (IIc) and (IId) are prepared by first treating a compound of formula (IIb) with an acid, such as acetic acid, preferably acetic acid, preferably diluted with an organic solvent, such as ethyl acetate, at temperatures of between about 50° C. and about 60° C., preferably at about 50° C., for a period of between about 10 hours and about 20 hours, preferably for a period of 20 hours. The organic reagents and solvents are removed by distillation in vacuo. The compound of formula (IIc) is isolated from the reaction mixture by standard isolation techniques, such as extraction by organic solvents and concentration. The compound of formula (IIc) is then treated to hydrolysis conditions and the compound of formula (IId) is then isolated from the reaction mixture by standard isolation techniques, such as chromatography.

In addition to the above described Reaction Schemes and the following Preparations and Examples, other compounds of the invention may be prepared according to method known to those of ordinary skill in the art.

For example, compounds of the invention wherein $R^1$ is —$SR^6$, —$S(O)_tR^7$, or —$N(R^7)R^8$ (where $R^6$, $R^7$ and $R^8$ are hydrogen) may be prepared by treating the compound of formula (EE) or a compound of formula (U) (as described above) with a suitable hydroxy-protecting agent to protect the free hydroxy group, and then treating the protected compound of formula (EE) or compound of formula (U) with a suitable acid in order to cleave the ketal. The resulting di-hydroxy compound may then be treated under standard acid hydrolysis conditions to form the corresponding lactone. The free hydroxy may then be derivatized to form a suitable leaving group, and subsequent substitution with the appropriately substituted thiol or amine, followed by acid hydrolysis will form compound of the invention wherein $R^1$ is —$SR^6$, —$S(O)_tR^7$, or —$N(R^7)R^8$.

Compounds of the invention wherein $R^3$ is —$SR^6$, —$S(O)_tR^7$, or —$N(R^7)R^8$ may be prepared by derivatizing the free hydoxy of a compound of formula (EE) to form a suitable leaving group, and then reacting the derivatized compound with the appropriately substituted nucleophile.

Compounds of the invention where $R^2$ is —$SR^6$, —$S(O)_rR^7$, or —$N(R^7)R^8$ may be prepared by preparing the lactone as described above, and then protecting the free hydroxy as described above. The resulting compound may then be treated to standard acid hydrolysis conditions to form the corresponding acid. The free hydroxy group may then be derivatized to form a suitable leaving group, and subsequent substitution with the appropriately substituted nucleophile, followed by de-protection will form compounds of the invention wherein $R^2$ is —$SR^6$, —$S(O)_rR^7$, or —$N(R^7)R^8$.

Compounds of the invention where $R^4$ is —$R^9$—$N(R^7)$—$R^{10}$—$R^{11}$ may be prepared by treating a compound of formula (F) as described above with an appropriately substituted amine under standard reductive amination conditions and then treating the resulting compound in the manner described above to form the corresponding compound of the invention. Compounds of the invention where $R^4$ is —$R^9$—$S(O)_t$—$R^{10}$—$R^{11}$ may be prepared by derivatizing the primary hydroxy of the compound of formula (G) as described above to form a suitable leaving group, and then reacting the resulting compound with the appropriate thiol alkoxide to form the desired product, which can be further oxidized under standard oxidation conditions to form the desired sulfinyl and sulfonyl compound.

Compounds of the invention wherein $R^1$ and $R^2$ together with the carbons to which they are attached form a monocyclic heterocyclic structure selected from the following:

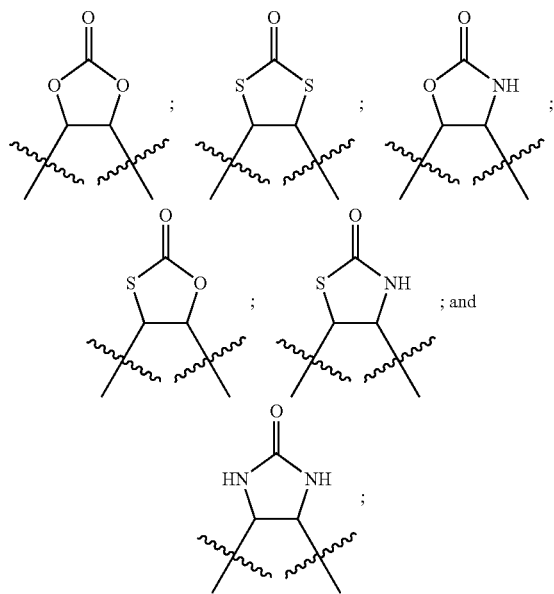

may be prepared by treating a compound of formula (Ia) or (IIa) as described above wherein $R^1$ and $R^2$ are independently selected from hydroxy, thiol or amine with an appropriate acylating agent, such as phosgene, under acid conditions.

Compounds of the invention wherein $R^4$ is —$R^9$—$R^{13}$—$R^{11}$ may be prepared according to the methods similar to those disclosed in Rodriguez, A. R., et al., *Tetrahedron Letters* (2001), Vol. 42, pp. 6057–6060.

Compounds of the invention wherein $R^4$ is —$R^9$—$R^{12}$ may be prepared by derivatizing a compound of formula (G) as described above to form a suitable leaving group on the primary hydroxy, and then treating the resulting compound with an appropriate hydroxy protecting agent in order to protect the remaining hydroxys. The leaving group can then be displaced with the appropriate aryl cuprate or Grignard reagent.

Compounds of the invention wherein $R^4$ is —$R^9$—O—$R^{10}$—$R^{11}$ may be prepared according to methods described herein using the appropriately substituted haloalkanoic acid salt, haloalkenoic acid salt, haloalkynoic acid salt or halocycloalkanoic acid salt. Alternatively, compound wherein $R^{10}$ is cycloalkylene may be prepared by alkylating the corresponding alkenylene-containing compound with the appropriate alkyl dihalide.

Compounds of the invention wherein $R^4$ is —$R^9$—O—$R^{12}$ may be prepared by treating the compound of formula (G) with the appropriate haloaralkyl (where the halo is on the alkyl chain) under substitution conditions.

Compounds of the invention wherein $R^4$ is —$R^9$—C(O)—$R^{10}$—$R^{11}$ may be prepared by hydrating the corresponding compound of the invention wherein $R^4$ is —$R^9$—$R^{13}$—$R^{11}$ wherein $R^{13}$ is an alkenylene chain under standard hydration conditions to form the corresponding alcohol, and then oxidizing the alcohol to the corresponding ketone.

Compounds of the invention wherein $R^4$ is —$R^9$—N(R$^7$)—$R^{10}$—$R^{11}$ or —$R^9$—S(O)—$R^{10}$—$R^{11}$ may be prepared in a similar manner as described above for compounds of the invention wherein $R^1$ and $R^2$ are —$SR^6$, —$S(O)_t$—$R^7$ and —$N(R^7)R^8$.

Compounds of the invention wherein $R^4$ is —$R^9$—$C(F)_2$—$R^9$—$R^{11}$ may be prepared from the corresponding ketone using the appropriate fluorinating agent, such as (diethylamino)sulfur trifluoride (DAST).

Compounds of the invention wherein $R^6$ is alkyl, aryl, aralkyl, —C(O)$R^7$, —C(S)$R^7$, —C(O)O$R^{14}$, or —C(S)O$R^{14}$ may be prepared by reacting a compound of formula (Ia) or (Ia) with the appropriate halide under standing substitution conditions. Compounds of the invention wherein $R^6$ is —C(O)N(R$^7$)R$^8$ or —C(S)N(R$^7$)R$^8$ may be prepared by reacting a compound of formula (Ia) or (IIa) with the appropriately substituted isocyanate or isothiocyanate.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques. It is understood that all polymorphs, amorphous forms, anhydrates, hydrates, solvates and salts of the compounds of the invention are intended to be within the scope of the invention.

To prepare the cyclodextrin clathrates of this invention, the lipoxin $A_4$ analogs of formula (I) and formula (II), or the lipoxin $A_4$ analogs described and claimed in U.S. Pat. No. 5,441,951; U.S. Pat. No. 5,079,261; U.S. Pat. No. 5,648,512; and U.S. Pat. No. 6,048,897, as defined above in the Summary of the Invention, can be dissolved in a pharmacologically acceptable solvent, e.g., in an alcohol, preferably ethanol, in a ketone, e.g., acetone or in an ether, e.g., diethyl ether, and mixed with aqueous solutions of α-cyclodextrin, β-cyclodextrin or γ-cyclodextrin, preferably β-cyclodextrin, at 20° C. to 80° C.; or the acids of the lipoxin $A_4$ analogs as defined above in the Summary of the Invention in the form of the aqueous solutions of their salts (e.g., Na⁻ or K⁻ salts) can be admixed with a cyclodextrin and after solution with the equivalent amount of an acid (e.g., HCl or $H_2SO_4$) to afford the corresponding cyclodextrin clathrate.

At this point or after cooling, the corresponding cyclodextrin clathrates separate in the form of crystals. However, it is also possible to convert oily and also crystalline compounds of formula (I) and/or formula (II), as defined above in the Summary of the Invention, by rather long stirring (e.g., for 1 hour to 14 days) at ambient temperature, by treatment with an aqueous solution of cyclodextrins, into the corresponding cyclodextrin clathrate form. The clathrates can then be isolated as solid, free-flowing crystals by suctioning off the solvents and drying.

Cyclodextrins used in this invention are commercially available, for example, from Aldrich Chemical Co., or can be prepared by methods known to those skilled in the art. See, for example, Croft, A. P. et al., "Synthesis of Chemically Modified Cyclodextrins", Tetrahedron (1983), Vol. 39, No. 9, pp. 1417–1474. Suitable cyclodextrins will include a wide variety of those which produce clathrates of the compounds of formula (I) and formula (II) as set forth above. See, for example, J. E. F. Reynolds (ed.) Martindale, The Extra Pharmacopoeia 28th ed. The Pharmaceutical Press, London 1982, p. 333 and 389–390 and O.-A. Neumueller (ed.), Roempps Chemie-Lexikon, 8. Aufl. Franckh'sche Verlagshandlung, Stuttgart 1981, p. 763–764, 841, 1053–1054.

By selection of the suitable amounts of cyclodextrins and water it is possible to obtain the new clathrates in a stoichiometric composition with a reproducible content of effective substance. The clathrates can be used in a dry hygroscopic form or in a water-containing, but less hygroscopic form. Typical molar ratios of cyclodextrin to a compound of formula (I) or a compound of formula (II) is 2:1 (cyclodextrin:compound).

The following specific preparations and examples are provided as a guide to assist in the practice of the invention, and are not intended as a limitation on the scope of the invention.

Preparation 1

Compounds of Formula (B) and (D)

A. A slurry of D-ribose (50 g, 0.33 mol) in acetone (500 mL) was stirred at ambient temperature as concentrated sulfuric acid (1.25 mL) was added. The reaction mixture was stirred for 30 minutes to give a clear solution and then stirred for an additional hour. The pH of the reaction mixture was adjusted to about pH 7 with calcium hydroxide (~7.0 g). The resulting slurry was filtered through a pad of celite. The filtrate was concentrated to give 64.8 g of D-ribofuranose-3,4-acetonide, the compound of formula (B) as a slightly colored oil, NMR: ($CDCl_3$) δ 1.30 (s, 3H), 1.47 (s, 3H) 2.05 (s, 1), 3.7 (m, 3H), 4.38 (m, 1H), 4.56 (d, 1H), 4.80 (d, 1H), 4.96 (d, 1H), 5.38 (d, 1H) ppm.

B. In a similar manner, compounds corresponding to the compound of formula (B) may be prepared.

C. A slurry of sodium borohydride (10.7 g, 0.34 mol) in water (0.75 L) was cooled in an ice bath and treated with the D-ribofuranose-3,4-acetonide (64.6 g, 0.34 mol) in water (1.25 L). The reaction mixture was stirred for about 2 hours before the addition of acetic acid (~23 mL) to consume excess borohydride and to adjust the pH to about pH 6. The reaction mixture was cooled in an ice bath before the addition of sodium periodate (72.7 g, 0.34 mol) in portions. The reaction mixture was stirred for about 2 hours at ambient temperature, concentrated under reduced pressure and extracted with ethyl acetate (3×). The combined ethyl acetate solutions were washed with brine, dried over sodium sulfate, and concentrated to give 47.4 g of (3,4-isopropylidene)erythrose, a compound of formula (D), as a colorless viscous oil: NMR (DMSO) δ 1.22 (s, 3H), 1.32 (s, 3H), 3.28 (d, 1H), 3.78 (m, 2H), 4.38 (d, 1H), 4.76 (m, 1H), 5.12 (m, 1H) ppm.

D. In a similar manner, other compounds of formula (D) may be prepared.

Preparation 2

Compounds of Formula (F), Formula (G), Formula (L) and Formula (M)

A. Solid L-rhamnose hydrate (100 g, 0.55 mol) was suspended in a 1:1 mixture of acetone and toluene (1 L) and concentrated. The process was repeated three times using increasing higher concentration of toluene. The flask was placed under high vacuum to remove traces of toluene. The anhydrous residue was dissolved in acetone (600 mL) and treated with methoxypropene (68 mL, 0.71 mol), pyridinium tosylate (3 g) and dl-10-camphorsulfonic acid (3 g). The reaction was stirred at ambient temperature for about 3 hours. The reaction mixture was basified by bubbling in ammonia gas and resulting solids were removed by filtration. The filtrate was concentrated and the syrupy liquid was dissolved in water and extracted with ethyl acetate (3×). The combined organic layers were washed with water (2×) and brine, dried, and concentrated to give 102 g of (3,4-isopropylidene)rhamnose, a compound of formula (F), as a viscous oil; $^1H$ NMR ($CDCl_3$) δ 1.32 (m, 6H), 1.45 (s, 3H), 3.92 (m, 1H), 4.05 (m, 1H), 4.59 (d, 1H), 4.87 (m, 1H), 5.2 (s, 1H) ppm.

B. A slurry of sodium borohydride (52 g, 1.4 mmol) in water (600 mL) was cooled in an ice bath and treated with the (3,4-isopropylidene)rhamnose (78 g, 0.38 mmol) in water (900 mL). The reaction mixture was stirred for about 5 hours before the addition of acetic acid to consume excess borohydride and to adjust the pH to about pH 6 (about 130 mL). The aqueous layer was concentrated under reduced pressure. The residue (in a minimum amount of water) was extracted with ethyl acetate (3×). The combined organic layers were dried, and concentrated to give 70 g of 5-(hydroxymethyl)-4-(1,2-dihydroxypropyl)-2,2-dimethyl-1,3-dioxolane, a compound of formula (G), as a colorless viscous oil; $^1H$ NMR ($CD_3OD$) δ 1.23 (d, 3H), 1.34 (s, 3H), 1.47 (s, 3H), 3.37 (m, 1H), 3.7 (m, 3H), 4.21 (m, 1H), 4.42 (m, 1H) ppm.

C. A solution of 4-(hydroxymethyl)-5-(1,2-dihydroxypropyl)-2,2-dimethyl-1,3-dioxolane (63 g, 0.33 mol) and sodium iodoacetate (75 g, 0.36 mol) in water was treated with solid sodium hydroxide (16 g, 0.35 mol). The reaction mixture was stirred overnight and then washed with ethyl acetate and ether. The aqueous layer was concentrated. The resulting residue was dissolved in DMF (20 mL) and treated with iodomethane (37 mL, 0.6 mol). The resulting reaction mixture was stirred overnight. The reaction mixture was diluted with two volumes of salt water and extracted with ethyl acetate (6×). The combined organic layers were dried, and concentrated to give 20 g of 2-[[(4S,5R)-5-(1,2-dihydroxypropyl)-2,2-dimethyl-1,3-dioxolan-4-yl]methoxy]ethanoic acid, methyl ester, a compound of formula (L), as a colorless viscous oil; $^1H$ NMR ($CDCl_3$) δ 1.27 (d, 3H), 1.38 (s, 3H), 1.48 (s, 3H), 3.57 (m, 1H), 3.77 (s, 3H), 3.8 (m, 2H), 4.13 (m, 2H), 4.4 (m, 2H) ppm.

D. A solution of 2-[[(4S,5R)-5-(1,2-dihydroxypropyl)-2,2-dimethyl-1,3-dioxolan-4-yl]methoxy]ethanoic acid, methyl ester (20 g, 72 mmol) in acetone (20 mL) was diluted with water (400 mL) and treated with solid sodium periodate (26.13 g, 122 mmol). The reaction was analyzed by TLC and was complete after stirring for 1 hour. The reaction mixture was extracted with ethyl acetate (3×). The combined organic layers were washed with brine, dried, and concentrated to give 12.6 g of 2-[[(4S,5S)-5-formyl-2,2-dimethyl-1,3-dioxolan-4-yl]methoxy]ethanoic acid, methyl ester, a compound of formula (M), as a slightly yellow viscous oil; $^1$H NMR (CDCl$_3$) δ 1.38 (s, 3H), 1.57 (s, 3H), 3.75 (m, 2H), 3.7 (s, 3H), 4.08 (m, 2H), 4.42 (m, 1H), 4.54 (m, 1H), 9.64 (d, 1H) ppm.

E. In a similar manner, the following compounds of formula (M) are prepared:

2-[[(4S,5S)-5-formyl-2,2-dimethyl-1,3-dioxolan-4-yl]methoxy]ethanoic acid, ethyl ester;

2-[2-[(4S,5S)-5-formyl-2,2-dimethyl-1,3-dioxolan-4-yl]ethoxy]ethanoic acid, ethyl ester;

2-[2-[(4S,5S)-5-formyl-2,2-dimethyl-1,3-dioxolan-4-yl]ethoxy]ethanoic acid, methyl ester;

2-[[(4S,5S)-5-formyl-2,2-diethyl-1,3-dioxolan-4-yl]methoxy]ethanoic acid, ethyl ester;

2-[2-[(4S,5S)-5-formyl-2,2-diethyl-1,3-dioxolan-4-yl]ethoxy]ethanoic acid, ethyl ester;

2-[2-[(4S,5S)-5-formyl-2,2-diethyl-1,3-dioxolan-4-yl]ethoxy]ethanoic acid, methyl ester;

2-[[(4S,5S)-5-formyl-2-methyl-2-ethyl-1,3-dioxolan-4-yl]methoxy]ethanoic acid, ethyl ester;

2-[2-[(4S,5S)-5-formyl-2-methyl-2-ethyl-1,3-dioxolan-4-yl]ethoxy]ethanoic acid, ethyl ester;

2-[2-[(4S,5S)-5-formyl-2-methyl-2-ethyl-1,3-dioxolan-4-yl]ethoxy]ethanoic acid, methyl ester;

2-[[(4S,5S)-5-formyl-2-methyl-2-ethyl-1,3-dioxolan-4-yl]methoxy]ethanoic acid, t-butyl ester; and 2-[2-[(4S,5S)-5-formyl-2-methyl-2-ethyl-1,3-dioxolan-4-yl]ethoxy]ethanoic acid, t-butyl ester.

Preparation 3

Compounds of Formula (O), Formula (P) and Formula (Q)

A. A solution of 2E-pent-2-en-4-yn-1-ol (58 g, 0.7 mol) in anhydrous tetrahydrofuran (THF) (1.0 L) under a nitrogen atmosphere in a 3.0 L 4-neck round-bottom flask was mechanically stirred and cooled in a dry ice/2-propanol bath as a solution of n-butyllithium in hexane (0.35 L, 2M, 0.77 mol) was added at a rate to maintain a temperature below −20° C. After 20 minutes, neat chlorotrimethylsilane (93 g, 0.77 mol) was added. After 20 minutes, a solution of n-butyllithium in hexane (0.35 L, 2M, 0.77 mol) was added at a rate to maintain a temperature below −20° C. After 10 minutes, neat chlorotrimethylsilane (93 g, 0.77 mol) was added. The reaction was allowed to warm to ambient temperature over about 1 hour. The reaction was treated with saturated ammonium chloride and diluted with hexane. The aqueous layer was washed with hexane. The combined organic extracts were washed with water and brine, dried and concentrated. The residue was dissolved in THF (~690 mL), treated with 1N hydrochloric acid (75 mL), and stirred overnight. The aqueous layer was separated and washed with ether. Combined organic layers were washed with water (3×) and brine, dried and concentrated to give 106 g of an oil. The residue was distilled under vacuum through a 15 cm jacketed column to obtain 72.6 g of 2E-5-trimethylsilylpent-2-en-4-yn-1-ol, a compound of formula (O), as a nearly colorless oil: b.p. 71–77° C./0.4 mm Hg; $^1$H-NMR (300 mHz, CDCl$_3$) δ 0.18 (s, 9H), 1.7 (bs, 1H), 4.18 (d, 2H), 5.75 (d, 1H), 6.29 (dm, 1H) ppm.

B. N-Bromosuccinimide (85.3 g, 0.48 mol) was added in portions to a nearly homogeneous solution of triphenylphosphine (128.2 g, 0.49 mol) and 2E-5-trimethylsilylpent-2-en-4-yn-1-ol (72.5 g, 0.47 mol) in dichloromethane (600 mL) under nitrogen and cooled in a dry ice/2-propanol bath to an initial temperature of below −20° C. The internal temperature of the reaction mixture was maintained at −10° C. to 0° C. throughout the addition by adjusting the rate of addition. The bath was allowed to warm to ambient temperature. After 2 hours, the reaction was complete. The reaction mixture was concentrated under vacuum to a thick paste and the residue was triturated with hexane (250 mL). The suspension was filtered and the solids and silica gel were rinsed with hexane (10×150 mL). The filtrate was concentrated under vacuum (30° C./60 mtorr) to obtain 44 g (89% yield) of 1-bromo-5-trimethylsilylpent-2-en-4-yne, a compound of formula (P), as a pale yellow oil: $^1$H-NMR (300 mHz, CDCl$_3$) δ 0.19 (s, 9H), 3.95 (d, 2H), 5.75 (d, 1H), 6.31 (dt, 1H) ppm.

C. Triphenylphosphine (64.1 g, 0.244 mol) was added to a solution of 1-bromo-5-trimethylsilylpent-2-en-4-yne (44.26 g, 0.204 mol) in toluene (204 mL). The mixture was stirred at ambient temperature under a nitrogen atmosphere. After 3 days the suspension was diluted with methyl tert-butyl ether (408 mL), stirred for 1 hour at ambient temperature, and the precipitate was collected by filtration. The filter cake was washed with methyl tert-butyl ether and dried under vacuum at 30° C. to get 79 g of 2E-5-trimethylsilylpent-2-en-4-ynyltriphenyl-phosphonium bromide, a compound of formula (Q), as an off-white powder: $^1$H-NMR (300 mHz, CDCl$_3$) δ 0.14 (s, 9H), 5.08 (dd, 2H), 5.91 (dt, 1H), 6.22 (dd, 1H), 7.6–8.0 (m, 15 H); Anal. Calculated for $C_{26}H_{28}BrPSi$ requires C, 65.13; H, 5.89; Br, 16.66; P, 6.46. found C, 64.95; H, 5.78; Br, 16.96; P, 6.31.

D. In a similar manner, other compounds of formula (O) may be prepared.

Preparation 4

Compounds of Formula (R), Formula (T), Formula (U), Formula (V), Formula (L), Formula (MM), and Formula (NN)

A. A slurry of 2E-5-trimethylsilylpent-2-en-4-ynyltriphenylphosphonium bromide (115 g, 0.24 mol) in THF (1 L) was stirred under nitrogen, cooled in a dry ice/2-propanol bath, and treated with a solution of n-butyllithium in hexane (2M, 120 mL, 0.24 mol) via dropwise addition. After about 5 minutes, the cooling bath was removed and the temperature of the reaction mixture was allowed to rise to <0° C. (internal). The reaction mixture was placed again in a dry ice/2-propanol bath. The reaction mixture was stirred as a solution of (2,3-isopropylidene)erythrose (36.6 g, 0.23 mol) in 200 mL of THF was added dropwise. The reaction mixture was allowed to warm to ambient temperature overnight. The reaction mixture was then cooled with dry ice/2-propanol and treated with saturated NH$_4$Cl. The resulting aqueous layer was washed with ethyl acetate. The organic layers were combined and washed with water and brine solution, dried, treated with silica gel and concentrated. Hexane/ethyl acetate (3:1) was added to the mixture to precipitate impurities, and the solution was filtered and concentrated. The resulting residue was treated with ether and hexane (1:1), silica gel, filtered and concentrated to give 50 g of product. Purification by chromatography on silica gel using a gradient of ether in hexane gave 13.9 g of a mixture of (4S,5R)-5-[(1E,3E)-6-(trimethylsilyl)-1,3-hexadien-5- ynyl]-2,2-dimethyl-4-(hydroxymethyl)-1,3-dioxolane and (4S,5R)-5-[(1Z,3E)-6-(trimethylsilyl)-1,3-hexadien-5-ynyl]-2,2-dimethyl-4-(hydroxymethyl)-1,3-dioxolane, a compound of formula (R); NMR for (1Z,3E) isomer only: $^1$H NMR (CDCl$_3$) δ 0.1 (s, 9H), 1.22 (s, 3H), 1.38 (s, 3H), 1.6 (m, 1H), 3.36 (m, 2H), 4.12 (m, 1H), 4.93 (m, 1H), 5.4 (t, 1H), 5.51 (d, 1H), 6.03 (t, 1H), 6.67 (dd, 1H) ppm.

B. A solution of a mixture of (4S,5R)-5-[(1E,3E)-6-(trimethylsilyl)-1,3-hexadien-5-ynyl]-2,2-dimethyl-4-(hydroxymethyl)-1,3-dioxolane and (4S,5R)-5-[(1Z,3E)-6-(trimethylsilyl)-1,3-hexadien-5-ynyl]-2,2-dimethyl-4-(hydroxymethyl)-1,3-dioxolane (14 g, 50 mmol) and t-butyl bromoacetate (9.6 mL, 65 mmol) in 150 mL of THF was cooled in an ice bath and treated with solid sodium hydride (60%, 2.5 g, 65 mmol). The slurry was allowed to warm to ambient temperature overnight. The reaction was analyzed by TLC and was about 40% complete. The reaction was then heated in a 63° C. oil bath for about 7 hours. The reaction mixture was allowed to cool and was poured into a mixture of ice, ethyl acetate, and saturated ammonium chloride. The aqueous layer was washed with ethyl acetate (2×). The combined organic layers were washed with water and brine solution, dried, treated with silica gel and concentrated. Purification by chromatography on silica gel using a gradient of ether in hexane gave 5.2 g of a mixture of 2-[[(4S,5R)-5-[(1E,3E)-6-(trimethylsilyl)-1,3-hexadien-5-ynyl]-2,2-dimethyl-1,3-dioxolan-4-yl]methoxy]ethanoic acid, 1,1-dimethylethyl ester and 2-[[(4S,5R)-5-[(1Z,3E)-6-(trimethylsilyl)-1,3-hexadien-5-ynyl]-2,2-dimethyl-1,3-dioxolan-4-yl]methoxy]ethanoic acid, 1,1-dimethylethyl ester, a compound of formula (T); NMR for (1Z, 3E) isomer only: $^1$H NMR (CDCl$_3$) δ 0.01 (s, 9H), 1.22 (s, 3H), 1.28 (s, 9H), 1.38 (s, 3H), 3.33 (m, 2H), 3.80 (m, 2H), 4.25 (m, 1H), 4.9 (m, 1H), 5.35 (m, 1H), 5.48 (dd, 1H), 6.0 (t, 1H), 6.72 (dd, 1H) ppm.

C. A solution of a mixture of 2-[[(4S,5R)-5-[(1E,3E)-6-(trimethylsilyl)-1,3-hexadien-5-ynyl]-2,2-dimethyl-1,3-dioxolan-4-yl]methoxy]ethanoic acid, 1,1-dimethylethyl ester and 2-[[(4S,5R)-5-[(1Z,3E)-6-(trimethylsilyl)-1,3-hexadien-5-ynyl]-2,2-dimethyl-1,3-dioxolan-4-yl]methoxy]ethanoic acid, 1,1-dimethylethyl ester in methylene chloride was treated with iodine until a red color persisted. The mixture was allowed to stand overnight. NMR analysis showed complete conversion. Reaction was treated with an aqueous solution of Na$_2$S$_2$O$_4$ and washed with water and brine, dried, treated with silica gel and concentrated to give 4.3 g of 2-[[(4S,5R)-5-[(1 E,3E)-6-(trimethylsilyl)-1,3-hexadien-5-ynyl]-2,2-dimethyl-1,3-dioxolan-4-yl]methoxy]ethanoic acid, 1,1-dimethylethyl ester, a compound of formula (U), as a viscous oil; $^1$H NMR (CDCl$_3$) δ 0.01 (s, 9H), 1.22 (s, 3H), 1.28 (s, 9H), 1.38 (s, 3H), 3.33 (m, 2H), 3.80 (m, 2H), 4.25 (m, 1H), 4.5 (m, 1H), 5.43 (m, 1H), 5.58 (dd, 1H), 6.23 (dd, 1H), 6.44 (dd, 1H) ppm.

D. In a similar manner and using the compound of formula (LL), the following compound of formula (MM) was made:
1,1,-dimethylethyl{{(2S,3R)-3-[(1E,3E)-6-(trimethylsilyl)-1,3-hexadien-5-ynyl]-1,4-dioxaspiro[4,5]dec-2-yl]methoxy]ethanoate, [α]$_D$=−14.351 (10.566 mg/cc in MeOH); $^1$H NMR (CDCl$_3$) δ 0.15 (s, 9H), 1.3 (m, 2H), 1.4 (s, 9H), 1.6 (m, 8H), 3.45 (m, 2H), 3.92 (m, 2H), 4.34 (m, 1H), 4.62 (m, 1H), 5.54 (d, 1H), 5.72 (dd, 1H), 6.26 (dd, 1H), 6.56 (dd, 1H) ppm.

E. A solution of 2-[[(4S,5R)-5-[(1E,3E)-6-(trimethylsilyl)-1,3-hexadien-5-ynyl]-2,2-dimethyl-1,3-dioxolan-4-yl]methoxy]ethanoic acid, 1,1-dimethylethyl ester in THF was treated with a solution of tetrabutylammonium fluoride in THF in portions. The reaction mixture was then stirred overnight. The reaction mixture was diluted with water and 1 N NaOH solution (1:1) and stirred overnight. The reaction mixture was poured into a mixture of ethyl acetate and saturated ammonium chloride. The aqueous layer was washed with ethyl acetate (2×). The combined organic layers were washed with water and brine solution, dried, treated with silica gel and concentrated to give 2.8 g of 2-[[(4S,5R)-5-[(1E,3E)-1,3-hexadien-5-ynyl]-2,2-dimethyl-1,3-dioxolan-4-yl]methoxy]ethanoic acid, a compound of formula (V), as an oil: $^1$H NMR (CDCl$_3$) δ 1.37 (s, 3H), 1.46 (s, 3H), 3.06 (s, 1H), 3.49 (m, 2H), 4.06 (m, 2H), 4.37 (m, 1H), 4.65 (t, 1H), 5.54 (d, 1H), 5.66 (dd, 1H), 6.28 (dd, 1H), 6.58 (dd, 1H) ppm.

F. In a similar manner and using a compound of formula (MM), the following compound of formula (NN) was prepared:
1,1,-dimethylethyl{{(2S,3R)-3-[(1E,3E)-1,3-hexadien-5-ynyl]-1,4-dioxaspiro[4,5]dec-2-yl]methoxy]ethanoate, $^1$H NMR (CDCl$_3$) δ 1.3 (m, 2H), 1.4 (s, 9H), 1.6 (m, 8H), 3.02 (m, 2H), 3.05 (m, 2H), 3.96 (m, 2H), 4.38 (q, 1H), 4.66 (t, 1H), 5.54 (dd, 1H), 5.78 (dd, 1H), 6.33 (dd, 1H), 6.65 (dd, 1H) ppm.

G. A solution of 2-[[(4S,5R)-5-[(1E,3E)-1,3-hexadien-5-ynyl]-2,2-dimethyl-1,3-dioxolan-4-yl]methoxy]ethanoic acid in THF was cooled in an ice bath and treated with a solution of trimethylsilyldiazomethane in THF in portions. Excess diazomethane was decomposed with acetic acid and the mixture was diluted with ether and washed with water, saturated sodium bicarbonate, water (2×), and brine, dried, treated with silica gel and concentrated. Purification by chromatography on silica gel using a gradient of ether in hexane gave 0.9 g of 2-[[(4S,5R)-5-[(1E,3E)-1,3-hexadien-5-ynyl]-2,2-dimethyl-1,3-dioxolan-4-yl]methoxy]ethanoic acid, methyl ester, a compound of formula (W), as an oil: $^1$H NMR (CDCl$_3$) δ 1.37 (s, 3H), 1.51 (s, 3H), 3.06 (s, 1H), 3.49 (m, 2H), 3.74 (s, 3H), 4.16 (m, 2H), 4.42 (m, 1H), 4.65 (t, 1H), 5.60 (dd, 1H), 5.79 (dd, 1H), 6.33 (dd, 1H), 6.65 (dd, 1H) ppm.

H. In a similar manner as described above, the following compounds corresponding to the compounds of formula (W) are prepared.

2-[[(4S,5R)-5-[(1E,3E)-1,3-hexadien-5-ynyl]-2,2-dimethyl-1,3-dioxolan-4-yl]methoxy]ethanoic acid, ethyl ester;
2-[[(4S,5R)-5-[(1E,3E)-1,3-hexadien-5-ynyl]-2,2-dimethyl-1,3-dioxolan-4-yl]methoxy]ethanoic acid, t-butyl ester;
2-[2-[(4S,5R)-5-[(1E,3E)-1,3-hexadien-5-ynyl]-2,2-dimethyl-1,3-dioxolan-4-yl]ethoxy]ethanoic acid, ethyl ester;
2-[2-[(4S,5R)-5-[(1E,3E)-1,3-hexadien-5-ynyl]-2,2-dimethyl-1,3-dioxolan-4-yl]ethoxy]ethanoic acid, t-butyl ester;
2-[2-[(4S,5R)-5-[(1E,3E)-1,3-hexadien-5-ynyl]-2,2-dimethyl-1,3-dioxolan-4-yl]ethoxy]ethanoic acid, methyl ester;
2-[3-[(4S,5R)-5-[(1E,3E)-1,3-hexadien-5-ynyl]-2,2-dimethyl-1,3-dioxolan-4-yl]propoxy]ethanoic acid, ethyl ester;
2-[3-[(4S,5R)-5-[(1E,3E)-1,3-hexadien-5-ynyl]-2,2-dimethyl-1,3-dioxolan-4-yl]propoxy]ethanoic acid, t-butyl ester;
2-[3-[(4S,5R)-5-[(1E,3E)-1,3-hexadien-5-ynyl]-2,2-dimethyl-1,3-dioxolan-4-yl]propoxy]ethanoic acid, methyl ester;
4-[[(4S,5R)-5-[(1E,3E)-1,3-hexadien-5-ynyl]-2,2-dimethyl-1,3-dioxolan-4-yl]methoxy]butanoic acid, ethyl ester;
4-[[(4S,5R)-5-[(1E,3E)-1,3-hexadien-5-ynyl]-2,2-dimethyl-1,3-dioxolan-4-yl]methoxy]butanoic acid, t-butyl ester;

4-[[(4S,5R)-5-[(1E,3E)-1,3-hexadien-5-ynyl]-2,2-dimethyl-1,3-dioxolan-4-yl]methoxy]butanoic acid, ethyl ester; and 4-[[(4S,5R)-5-[(1E,3E)-1,3-hexadien-5-ynyl]-2,2-dimethyl-1,3-dioxolan-4-yl]methoxy]butanoic acid, t-butyl ester.

Preparation 5

Compounds of Formula (Ta) and Formula (Ua)

A. A slurry of 5-trimethylsilylpent-2-en-4-ynyltriphenylphosphonium bromide, a compound of formula (Q), (8.5 g, 17.7 mmol) in THF (120 mL) was stirred under nitrogen, cooled in a dry ice/acetonitrile bath, and treated with a solution of n-butyllithium in hexane (2M, 8 mL, 16 mmol) via dropwise addition. The dry ice bath was replaced with an ice bath and the reaction mixture was stirred for about 15 minutes until a homogeneous mixture was obtained. The dry ice bath was replaced and the reaction mixture was treated with a solution of 2-[[(4S,5S)-5-formyl-2,2-dimethyl-1,3-dioxolan-4-yl]methoxy]ethanoic acid, methyl ester, a compound of formula (M), (3.7 g, 16 mmol) in 60 mL of THF. The reaction mixture was stirred in a dry ice bath for 1 hour, which was then replaced with the ice bath. After 1 hour, the reaction mixture was diluted with ether and monobasic potassium phosphate. The aqueous layer was washed with ether. The combined organic layers were washed with water and brine, dried, filtered through a pad of silica gel, and concentrated. A hexane/ethyl acetate (~3:1 mixture) was added to the residue to precipitate impurities. The residue was filtered and concentrated. The resulting residue was treated with ether and hexane (1:1), followed by silica gel, filtration and concentration to give 9.2 g of a 1:3 mixture of triphenylphosphine oxide and 2-[[(4S,5R)-5-[(1Z,3E)-6-(trimethylsilyl)-1,3-hexadien-5-ynyl]-2,2-dimethyl-1,3-dioxolan-4-yl]methoxy]ethanoic acid, methyl ester, a compound of formula (Ta); $^1$H NMR (CDCl$_3$) δ 0.01 (s, 9H), 1.2 (s, 3H), 1.33 (s, 3H), 3.33 (m, 2H), 3.56 (s, 3H), 3.90 (m, 2H), 4.25 (m, 1H), 4.88 (m, 1H), 5.32 (t, 1H), 5.48 (d, 1H), 5.98 (t, 1H), 6.68 (dd, 1H) ppm (NMR for ester only).

B. A solution of the above residue in methylene chloride was treated with sufficient quantity of iodine to maintain a red color and allowed to stand for 3 hours in the light. The reaction mixture was then treated with saturated aqueous sodium hyposulfite, dried with sodium sulfate, filtered through a pad of silica gel, and concentrated to give 4.53 g of product. Chromatography on silica gel using a gradient of 5 to 100% ether in hexane gave 2.74 g of 2-[[(4S,5R)-5-[(1E,3E)-6-(trimethylsilyl)-1,3-hexadien-5-ynyl]-2,2-dimethyl-1,3-dioxolan-4-yl]methoxy]ethanoic acid, methyl ester, a compound of formula (Ua); $^1$H NMR (CDCl$_3$) δ 0.01 (s, 9H), 1.18 (s, 3H), 1.33 (s, 3H), 3.3 (m, 2H), 3.56 (s, 3H), 3.90 (m, 2H), 4.25 (m, 1H), 4.48 (m, 1H), 5.46 (m, 1H), 5.58 (dd, 1H), 6.14 (t, 1H), 6.44 (dd, 1H) ppm.

C. In a similar manner, other compounds of formula (Ua) may be prepared.

Preparation 6

Compounds of Formula (Y), Formula (Z), Formula (AA), Formula (BB), Formula (CC) and Formula (DD)

A. Oxalyl chloride (60 mL, 686 mmol) and dimethylformamide (DMF) (8 drops, cat.) were added to a stirred suspension of 2-(4-fluorophenoxy)ethanoic acid (97.3 g, 572 mmol) in dichloromethane (500 mL). After 22 hours, the mixture was concentrated under vacuum to obtain 108 g of 2-(4-fluorophenoxy)ethanoic acid chloride, a compound of formula (Y), as a yellow oil in quantitative yield; $^1$H NMR (CDCl$_3$) δ 4.90 (s, 2H), 6.84 (m, 2H), 6.99 (m, 2H) ppm.

B. 2-(4-Fluorophenoxy)ethanoic acid chloride was added slowly to a stirred suspension of N,O-dimethylhydroxylamine hydrochloride (55.80 g, 572 mmol) in saturated K$_2$CO$_3$ and ethyl acetate (375 mL). A moderately exothermic reaction occurred (larger scale reactions are cooled with an ice bath), and after 20 minutes, the reaction mixture was partitioned between water and ether. The ether layer was washed with 1 M HCl and saturated NaCl, and dried over MgSO$_4$. The dried solution was filtered and concentrated under vacuum to give N-methoxy-N-methyl-2-(4-fluorophenoxy)ethanamide, a compound of formula (Z), as a yellow oil which solidified to an off-white crystalline solid, 113.05 g (73% yield from starting acid); $^1$H NMR (CDCl$_3$, 400 mHz) δ 3.21 (s, 3H), 3.73 (s, 3H), 4.75 (s, 2H), 6.87 (m, 2H), 6.95 (m, 2H) ppm.

C. A solution of ethynylmagnesium bromide (0.5 M in THF, 508 mL, 254 mmol), was added slowly, as a stream down the side of the flask, to an ice water cooled solution of N-methoxy-N-methyl-2-(4-fluorophenoxy)ethanamide (20.00 g, 74 mmol) in THF (100 mL). After an additional 30 minutes at 0° C., the reaction mixture was poured into a vigorously stirred mixture of 1M NaH$_2$SO$_4$ (1700 mL) and ether (1 L). The layers were separated and the aqueous layer then extracted with ether (700 mL). The combined organic phases were washed with brine and dried over MgSO$_4$, filtered, and concentrated under vacuum. The residue was purified by eluting through a plug of silica gel (10 cm×3 cm) with 1:4 ether:pet. ether to afford 27.65 g (91% yield) of 4-(4-fluorophenoxy)-1-butyn-3-one, a compound of formula (AA), as a low melting solid; $^1$H NMR (CDCl$_3$) δ 3.40 (s, 1H), 4.70 (s, 2H), 6.85 (m, 2H), 7.0 (t, 2H) ppm.

D. A solution of R-Alpine-Borane® (0.5 M in THF, 930 mL, 465 mmol) was evaporated to dryness under vacuum to get about 150 g of a thick syrup. 4-(4-Fluorophenoxy)-1-butyn-3-one (27.6 g, 155 mmol) was added and when an exothermic reaction was observed, the reaction mixture was cooled with an ice/water bath, then allowed to warm to ambient temperature. After two days, the reaction mixture was cooled to 0° C. and acetaldehyde (26 mL, 465 mmol) was added to quench the excess reagent. After stirring at ambient temperature for 2 hours the reaction mixture was placed under vacuum and stirred first at 0° C. for one hours, then at 65° C. for 2 hours. The reaction mixture was cooled to ambient temperature and ether (300 mL) was added under nitrogen. Ethanolamine (30 mL, 465 mmol) was added drop-wise at 0° C. and the resulting reaction mixture was stored in the freezer overnight. The resulting precipitate was removed by filtration and washed with cold ether. The combined filtrates were concentrated under vacuum. The crude product was purified by flash chromatography on a 2.5 L column of silica gel with 10–25% ethyl acetate in hexane as eluant to obtain 27 g of (3S)-4-(4-fluorophenoxy)-3-hydroxy-1-butyne, a compound of formula (BB), in quantitative yield; $^1$H NMR (CDCl$_3$) δ 2.56 (s, 1H), 4.10 (m, 2H), 4.78 (m, 1H), 6.85 (m, 2H), 7.0 (m, 2H). This material was determined to be about 64% ee based on chiral HPLC of its 3,5-dinitrobenzoyl ester (see below).

E. To a solution of (3S)-4-(4-fluorophenoxy)-3-hydroxy-1-butyne (est. 490 mmol) in methylene chloride (1 L) was added 3,5-dinitrobenzoyl chloride (125 g, 539 mmol) at between −5° C. and 0° C., followed by slow addition of triethylamine (10.8 mL, 77 mmol) and a catalytic amount of dimethylaminopyridine (DMAP) (20 mg). After the mixture was stirred at ambient temperature for 40 minutes, the reaction mixture was cautiously partitioned between methylene chloride and aqueous NaHCO$_3$. The aqueous layer was extracted with dichloromethane, and the combined organic layers were washed with water and brine, and dried over Na$_2$SO$_4$. The solution was filtered through a pad of silica gel with methylene chloride which gave crude product as a tan solid. Rapid recrystallization from 99:1 mixture of methanol:acetic acid (5 L) gave 101 g of the enantiomerically enriched product, (3S)-4-(4-fluorophenoxy)-3-(3',5'-dinitrobenzoyl)oxy-1-butyne, a compound of formula (BBa) as fluffy white needles. This material was determined to have greater than 98% ee by analytical HPLC using a Diacel Chiralpak AD® (4.6×250 mm, 60% 2-propanol/hexane, 1 mL/min), which separates the (R) (11.5 min) and the (S) (19.3 min) enantiomers; $^1$H NMR (CDCl$_3$) δ 2.65 (s, 1H), 4.40 (m, 2H), 6.05 (m, 1H), 6.90 (m, 2H), 7.0 (t, 2H), 9.15 (s, 2H), 9.25 (s, 1H) ppm.

F. To a solution of (3S)-4-(4-fluorophenoxy)-3-(3',5'-dinitrobenzoyl)oxy-1-butyne (10.35 g, 98% ee, 27.6 mmol) in THF (115 mL), was added methanol (115 mL) and K$_2$CO$_3$ (0.58 g). After stirring for 3.5 hours, the reaction mixture was quenched with acetic acid (2 mL). The solvents were evaporated and the resulting slurry was filtered and the solid was washed with ether. The filtrate was concentrated and the filtration/ether wash sequence was repeated. Concentration gave 4.02 g of (3S)-4-(4-fluorophenoxy)-3-hydroxy-1-butyne (98% ee), a compound of formula (BB); $^1$H NMR (CDCl$_3$) δ 2.56 (s, 1H), 4.10 (m, 2H), 4.78 (m, 1H), 6.85 (m, 2H), 7.0 (m, 2H).

G. A mixture of (3S)-4-(4-fluorophenoxy)-3-hydroxy-1-butyne (2.5 g, 14 mmol), N-bromosuccinimide (NBS) (2.74 g, 15.4 mmol) and AgNO$_3$ (0.12 g, 0.7 mmol) in acetone (70 mL) was stirred at ambient temperature. The pale solution became cloudy over 30 minutes. The mixture was concentrated under vacuum and the resulting residue was filtered through a plug of silica gel (1×5 cm) eluted with 1:4 ethyl acetate:hexane to obtain (3S)-1-bromo-4-(4-fluorophenoxy)-3-hydroxy-1-butyne, a compound of formula (CC), as a pale yellow oil containing some ethyl acetate, 4.75 g (quant.); $^1$H NMR (CDCl$_3$) δ 3.95–4.15 (m, 2H), 4.75 (m, 1H), 6.86 (m, 2H), 6.97 (m, 2H) ppm.

H. AlCl$_3$ (2.79 g, 21 mmol) was added in portions to a mixture of lithium aluminum hydride (LAH) (1.06 g, 28 mmol) and ether (70 mL). A solution of (3S)-1-bromo-4-(4-fluorophenoxy)-3-hydroxy-1-butyne (14 mmol) in ether (10 mL) was added cautiously. A vigorous reaction with evolution of gas was observed. The mixture was warmed to reflux on a water bath for 30 minutes. The reaction mixture was then cooled to 0° C. and treated with 2.8 mL water (slowly, vigorous reaction), 2.8 mL 15% NaOH, and finally 8.4 mL water. The resulting suspension was then stirred 10 minutes, filtered and the solids were washed with THF and ether. The solution was concentrated under vacuum to afford 2.94 g (81% yield for two steps) of (1E, 3S)-1-bromo-4-(4-fluorophenoxy)-3-hydroxy-1-butene, a compound of formula (DD); $^1$H NMR (CDCl$_3$) δ 2.41 (t, 1H), 3.85 (dd, 1H), 3.99 (dd, 1H), 4.50 (m, 1H), 6.31 (dd, 1H), 6.52 (dd, 1H), 6.83 (m, 2H), 6.97 (t, 2H) ppm.

I. In a similar manner, other compounds of formula (DD) may be prepared:

Preparation 7

Compounds of Formula (EE)

A. In a flame dried flask, a solution of (1E,3S)-1-bromo-4-(4-fluorophenoxy)-3-hydroxy-1-butene (0.84 g, 3 mmol), tetrakis(triphenylphosphine)palladium(0) (0.13 g, 0.2 mmol) and copper(I) iodide (60 mg, 0.3 mmol) in THF (50 mL) and diethylamine (5 mL, 48 mmol) was carefully deoxygenated by bubbling in argon gas for 45 minutes. The reaction was stirred as a solution of 2-[[(4S,5R)-5-[(1E,3E)-1,3-hexadien-5-ynyl]-2,2-dimethyl-1,3-dioxolan-4-yl]methoxy]ethanoic acid, methyl ester, (0.9 g, 3.2 mmol) in THF (50 mL), which had been deoxygenated by bubbling in argon for 45 minutes, was added. After about 4 hours, the reaction was complete. The reaction mixture was diluted with hexane and filtered through a pad of silica gel and the silica gel was eluted with ether. The combined filtrates were concentrated to give an oil. Purification by chromatography using a 20–75% gradient of ether in hexane gave 1.1 g of 2-[[(4S,5R)-5-[(1E,3E,7E,9S)-9-hydroxy-10-(4-fluorophenoxy)-1,3,7-decatrien-5-ynyl]-2,2-dimethyl-1,3-dioxolan-4-yl]methoxy]ethanoic acid, methyl ester, a compound of formula (EE), as an oil; $^1$H NMR (CDCl$_3$) δ 1.37 (s, 3H), 1.5 (s, 3H), 3.52 (m, 2H), 3.75 (s, 3H), 3.83 (m, 2H), 4.13 (m, 2H), 4.44 (m, 1H), 5.74 (m, 1H), 5.76 (m, 2H), 6.05 (m, 1H), 6.17 (m, 1H), 6.29 (m, 1H), 6.58 (dd, 1H), 6.88 (m, 4 H) ppm.

B. In a similar manner, other compounds of formula (EE) may be prepared:

Preparation 8

Compounds of Formula (GG)

A. A slurry of copper sulfate (175 g, 1.09 mol, 2 eq) and rhamnose hydrate (100 g, 0.55 mol) in freshly distilled cyclohexanone (330 g) was stirred under nitrogen as concentrated sulfuric acid (1.5 mL) was added at once. The reaction mixture was warmed to about 29° C. internal. The reaction mixture was allowed to stir overnight. The reaction was analyzed by TLC (ethyl acetate) and was complete. The reaction mixture was filtered through a pad of celite and the solid was washed with ethyl acetate. The filtrate was treated with about 1.5 mL of concentrated ammonium hydroxide to pH 7, and the resulting solid was removed by filtration. The filtrate was concentrated under reduced pressure to give a colorless oil. The residue was dissolved in ether and treated with hexane and allowed to stand overnight. Resulting solid was isolated by filtration and dried to give 92.3 g (0.31 mol, 57%) of (2R,3R)-3-(1,2-dihydroxypropyl)-1,4-dioxaspiro[4,5]decane-2-carboxaldehyde, as an off-white solid: [α]D=+0.457 (10.485 mg/cc MeOH); $^1$H NMR (CDCl$_3$) δ 1.34 (d, 3H), 1.40 (m, 2H), 1.6 (m, 8H), 2.78 (d, 1H), 3.0 (s, 1 H), 3.9 (m, 1H), 4.07 (m, 1H), 4.6 (d, 1H), 4.9 (m, 1H), 5.4 (s, 1H) ppm.

B. In a similar manner, other compounds of formula (GG) are prepared.

Preparation 9

Compounds of Formula (HH)

A. A slurry of sodium borohydride (34.2 g, 0.9 mol) in methanol (400 mL) was cooled in an ice bath and treated with (2R,3R)-3-(1,2-dihydroxypropyl)-1,4-dioxaspiro[4,5]decane-2-carboxaldehyde (92 g, 0.27 mol) dissolved in 200 mL of methanol. The reaction mixture was stirred for about 4 hours. The reaction was complete and acetic acid was added to consume excess borohydride and to adjust the pH to about 6 (about 120 mL). The reaction mixture was concentrated and dissolved in ethyl acetate. The resulting solid was removed by filtration. The combined filtrates were dried, and concentrated to give a slightly yellow viscous oil. The residue was dissolved in ether and treated with hexane to precipitate the product. Solids were isolated by filtration and dried to give 81.2 g of (2R,3S) α$^2$-(1-hydroxyethyl)-1,4-dioxaspiro[4,5]decane-2,3-dimethanol as an off-white solid: [α]D=+5.494 (10.119 mg/cc MeOH); $^1$H NMR (CD$_3$OD) δ 1.28 (d, 3H), 1.43 (m, 2H), 1.7 (m, 8H), 3.42 (dd, 1H), 3.7 (m, 3H), 4.25 (m, 1H), 4.42 (dd, 1H) ppm.

B. In a similar manner, other compounds of formula (HH) are prepared.

Preparation 10

Compounds of Formula (JJ)

A. A mixture of (2R,3S) α$^2$-(1-hydroxyethyl)-1,4-dioxaspiro[4,5]decane-2,3-dimethanol (81 g, 0.32 mol) and t-butyl bromoacetate (77 g, 0.39 mol, 1.2 eq) in 1 L of toluene was stirred with a mechanical stirrer as 80 mL of sodium hydroxide in water (25% by weight) was added. Phase transfer catalyst, tetrabutylammonium sulfate (7.8 g, 23 mmol, 0.07 eq), was added and the reaction mixture was stirred overnight and monitored by TLC. The reaction mixture was diluted with ethyl acetate and saturated aqueous potassium phosphate monobasic. The combined organic layers were dried and concentrated to give a clear oil. Chromatography on 1 Kg of silica gel using a step gradient of 20% ether in hexane, 50% ether in hexane, and ether gave 34 g of pure product and 38 g of an impure fraction. Chromatography on the mixed fraction using a gradient of ether in hexane gave a pure fraction which was combined with the earlier fraction to give 50.8 g (44%) of 1,1-dimethylethyl [[(2S,3R) 3-(1,3-dihydroxypropyl)-1,4-dioxaspiro[4,5]dec-2-yl]methoxy]acetate as an oil: [α]D=+8.587 (10.301 mg/cc MeOH). $^1$H NMR (CDCl$_3$) δ 1.24 (d, 3H), 1.35 (m, 2H), 1.47 (s, 9H), 1.6 (m, 8H), 3.6 (m, 2H), 3.8 (m, 2H), 3.95 (m, 2H), 4.32 (m, 1H), 4.4 (m, 1H) ppm.

B. In a similar manner, other compounds of formula (JJ) are prepared.

Preparation 11

Compounds of Formula (KK)

A. A solution of 1,1-dimethylethyl [[(2S,3R) 3-(1,3-dihydroxypropyl)-1,4-dioxaspiro[4,5]dec-2-yl]methoxy]acetate (50 g, 138 mmol) in acetone (350 mL) was treated with a solution of periodate (50 g, 235 mmol, 1.7 eq) in water (1.2 L). The reaction mixture was stirred vigorously under nitrogen and monitored by TLC. After about 4 hours, the reaction was complete by TLC analysis. Acetone was removed under reduced pressure without heating. The reaction mixture was extracted with ethyl acetate (3×500 mL). The combined organic layers were dried and concentrated under reduced pressure without heating to give 40 g of 1,1-dimethylethyl [[(2S,3S) 3-formyl-1,4-dioxaspiro[4,5]dec-2-yl]methoxy] acetate as a clear oil: [α]$_D$=−1.142 (10.147 mg/cc in MeOH); $^1$H NMR (CDCl$_3$) δ 1.38 (m, 2H), 1.42 (s, 9H), 1.61 (m, 8H), 1.73 (m, 2H), 3.52 (dd, 1 H), 3.72 (dd, 1 H), 3.88 (s, 2H), 4.38 (dd, 1 H), 4.52 (m, 1H), 9.62 (s, 1lH) ppm.

B. In a similar manner, other compounds of formula (KK) are prepared.

Preparation 12

Compounds of Formula (LL)

A. A slurry of 2E-5-trimethylsilylpent-2-en-4-ynyltriphenyl-phosphonium bromide, a compound of formula (Q), (67.1 g, 0.14 mol) in THF (875 mL) was stirred under nitrogen, cooled in a dry ice acetonitrile bath (−30° C. internal), and treated with a solution of n-butyllithium (66.5 mL, 0.133 mol, 2M in hexane) via dropwise addition. The dry ice bath was replaced with an ice bath and the reaction was stirred for about 15 minutes until a homogeneous, red-colored mixture was obtained. The dry ice bath was replaced and the reaction mixture was cooled to about −30° C. The reaction mixture was treated with a solution of 1,1-dimethylethyl [[(2S,3S) 3-formyl-1,4-dioxaspiro[4,5] dec-2-yl]methoxy]acetate (40 g, 0.127 mol) in 125 mL of THF. The reaction mixture was stirred for 1 hour with the dry ice bath. With the internal temperature around −30° C., the reaction mixture was diluted with saturated potassium phosphate (pH=5). The aqueous layer was washed with ether (3×). Combined organic layers were washed with water and brine, dried, treated with silica gel, and concentrated. The residue was diluted with about 3:1 mixture of hexane to ethyl acetate to precipitate the impurities. The resulting slurry was filtered and the solid was washed with the hexane/ethyl acetate mixture. The filtrate was concentrated. The procedure was repeated using a mixture of ether and hexane (1:1) and treatment with silica gel to give 50.29 g of 1,1-dimethylethyl [[(2S,3R)-3-[(1Z,3E)-6-(trimethylsilyl)-1,3-hexadien-5-ynyl]-1,4-dioxaspiro[4,5]dec-2-yl]methoxy]ethanoate as an oil. Proton NMR analysis of the product indicated a 2:1 mixture of E,Z- to E,E-isomers. The data for the for the Z,E isomer can be extracted from the mixture: $^1$H NMR (CDCl$_3$) δ 0.15 (s, 9H), 1.3 (m, 2H), 1.4 (s, 9H), 1.6 (m, 8H), 3.45 (m, 2H), 3.92 (m, 2H), 4.34 (m, 1H), 5.02 (m, 1H), 5.48 (dd, 1H), 5.6 (d, 1H), 6.16 (dd, 1H), 6.82 (dd, 1H) ppm.

B. In a similar manner, other compounds of formula (KK) are prepared.

EXAMPLE 1

Compounds of Formula (IIa)

A. A solution of 2-[[(4S,5R)-5-[(1E,3E,7E,9S)-9-hydroxy-10-(4-fluorophenoxy)-1,3,7-decatrien-5-ynyl]-2,2-dimethyl-1,3-dioxolan-4-yl]methoxy]ethanoic acid, methyl ester, (1.1 g, 1.8 mmol) in methanol (25 mL) was treated with 1 mL of 1 N hydrochloric acid and the reaction was stirred for 2 days. The pH of the reaction was adjusted to neutrality. Purification on preparative reverse phase semi-prep column using a gradient of acetonitrile in water yielded 1.1 g of (5S,6R,7E,9E,13E,15S)-16-(4-fluorophenoxy)-5,6, 15-trihydroxy-3-oxahexadeca-7,9,13-trien-11-ynoic acid, methyl ester, as an oil; $^1$H NMR (CDCl$_3$) δ 3.67 (m, 2H), 3.75 (s, 3H), 3.83 (m, 1H), 3.95 (m, 1H), 4.13 (m, 2H), 4.37 (m, 1H), 4.58 (m, 1H), 5.73 (dd, 1H), 5.86 (dd, 1H), 6.04 (dt, 1H), 6.17 (m, 1H), 6.40 (m, 1H), 6.58 (m, 1H), 6.9 (m, 4H) ppm.

B. In a similar manner, the following compound of formula (IIa) was prepared:
(5S,6S,7E,9E,13E,15S)-16-(4-fluorophenoxy)-5,6,15-trihydroxy-3-oxahexadeca-7,9,13-trien-11-ynoic acid, methyl ester.

C. A solution of (5S,6R,7E,9E,13E,15S)-16-(4-fluorophenoxy)-5,6,15-trihydroxy-3-oxahexadeca-7,9,13-trien-11-ynoic acid, methyl ester, (0.4 g, 0.95 mmol) in methanol (20 mL) was treated with 1 N NaOH (aq) (4 mL, 4 mmol) solution and shaken and allowed to stand for three hours. The reaction mixture was then treated with saturated potassium monophosphate and poured onto an HP20 column. Elution with a gradient of methanol in water gave 0.35 g of (5S,6R,7E,9E,13E,15S)-16-(4-fluorophenoxy)-5,6,15-trihydroxy-3-oxahexadeca-7,9,13-trien-11-ynoic acid, which solidified upon standing; $^1$H NMR (CD$_3$OD) δ 3.63 (m, 2H), 3.667 (m, 1H), 3.91 (m, 2H), 4.113 (s, 2H), 4.150, (t, 1H), 4.498, (m, 1H), 5.762 (dd, 1H), 5.953 (dd, 1H), 6.003 (dt, 1H), 6.202(dd, 1H), 6.380 (dd, 1H), 6.596 (dd, 1H), 6.928 (m, 2H), 6.988 (m, 2H) ppm.

D. In a similar manner, the following compound of formula (IIa) was prepared:
(5S,6S,7E,9E,13E,15S)-16-(4-fluorophenoxy)-5,6,15-trihydroxy-3-oxahexadeca-7,9,13-trien-11-ynoic acid.

E. In a similar manner as described above, the following compounds of formula (II) are prepared:
(2E,5S,6R,7E,9E,13E,15S)-16-(4-fluorophenoxy)-5,6,15-trihydroxyhexadeca-2,7,9,13-tetraen-11-ynoic acid;
(2E,5S,6R,7E,9E,13E,15S)-16-(4-fluorophenoxy)-5,6,15-trihydroxyhexadeca-2,7,9,13-tetraen-11-ynoic acid, methyl ester;
(5R,6R,7E,9E,13E,15S)-16-(4-fluorophenoxy)-5,6,15-trihydroxy-3-oxahexadeca-7,9,13-trien-11-ynoic acid;
(5R,6R,7E,9E,13E,15S)-16-(4-fluorophenoxy)-5,6,15-trihydroxy-3-oxahexadeca-7,9,13-trien-11-ynoic acid, methyl ester;
(5S,6R,7E,9E,13E,15S)-16-(4-fluorophenoxy)-5,6,15-trihydroxy-3-oxahexadeca-7,9,13-trien-11-ynamide;
(5S,6R,7E,9E,13E,15S)-16-(4-fluorophenoxy)-5,6,15-trihydroxy-N,N-dimethyl-3-oxahexadeca-7,9,13-trien-11-ynamide;
(7S,8R,9E,11E,15E,17)-18-(4-fluorophenoxy)-7,8,17-trihydroxy-5-oxaoctadeca-9,11,15-trien-13-ynoic acid;
(7S,8R,9E,11E,15E,17S)-18-(4-fluorophenoxy)-7,8,17-trihydroxy-5-oxaoctadeca-9,11,15-trien-13-ynoic acid, methyl ester;
(5S,6R,7E,9E,13E,15S)-16-(4-fluorophenoxy)-5,6,15-trihydroxy-3-thiahexadeca-7,9,13-trien-11-ynoic acid;
(5S,6R,7E,9E,13E,15S)-16-(4-fluorophenoxy)-5,6,15-trihydroxy-3-azahexadeca-7,9,13-trien-11-ynoic acid;
(5S,6R,7E,9E,13E,15S)-16-(4-fluorophenoxy)-5,15-dihydroxy-6-(methylamino)-3-oxahexadeca-7,9,13-trien-11-ynoic acid; and
(5S,6R,7E,9E,13E,15S)-16-(4-fluorophenoxy)-5,15-dihydroxy-6-amino-3-oxahexadeca-7,9,13-trien-11-ynoic acid.

F. The compounds of formula (IIa) as prepared above are treated with the appropriate acylating agent, such as phosgene, under acidic conditions to yield the following compounds:
[[5-[(1E,3E,7E,9R)-10-(4-fluorophenoxy)-9-hydroxy-1,3,7-decatrien-5-ynyl]-2-oxo-1,3-dioxolan-4-yl]methoxy]acetic acid;
[[5-[(1E,3E,7E,9R)-10-(4-fluorophenoxy)-9-hydroxy-1,3,7-decatrien-5-ynyl]-2-oxo-1,3-oxathiolan-5-yl]methoxy] acetic acid; and
[[5-[(1E,3E,7E,9R)-10-(4-fluorophenoxy)-9-hydroxy-1,3,7-decatrien-5-ynyl]-2-oxo-5-oxazolidinyl]methoxy]acetic acid.

EXAMPLE 2

Compounds of Formula (IIb)

A. A solution of (1E,3S)-1-bromo-4-(4-fluorophenoxy)-3-hydroxy-1-butene (16.6 g, 63 mmol), solid tetrakistriphenylphosphinePd(0) (3.67 g, 3 mmol), and Cu(I) iodide (1.2 g, 6.3 mmol) in diethylamine (50 mL) and THF (800 mL) was stirred and deoxygenated by bubbling argon through the mixture for 90 minutes. Argon addition continued as a similarly deoxygenated solution (argon bubbling) of 1,1-dimethylethyl [[(2S,3R)-3-[(1E,3E)-6-(trimethylsilyl)-1,3-hexadien-5-ynyl]-1,4-dioxaspiro[4,5]dec-2-yl]methoxy] ethanoate (23 g, 63 mmol) in 200 mL of THF was added dropwise over about 3 hours. The reaction was monitored by TLC analysis. After about an additional 2 hours, the reaction was complete by TLC analysis. The reaction mixture was diluted with hexane (about 400 mL), treated with silica gel (about 40 g) and filtered. The solid was washed with a 1:1 solution of ether and hexane. The filtrate was concentrated to give 36.8 g of an oil. The residue was dissolved in ether, treated with hexane, and allowed to stand over the weekend. Highly colored material was removed by filtration through a pad of silica gel and product eluted with ether. The desired fractions were concentrated to give an oil. Purification by chromatography on 1 Kg of silica gel using a 15–50% gradient of ether in hexane gave 16.9 g of 1,1-dimethylethyl [[(2S,3R)-3-[(1E,3E,7E,9S)-10-(4-fluorophenoxy)-9-hydroxyl-1,3,7-decatrien-5-ynyl]-1,4-dioxaspiro[4,5]dec-2-yl]methoxy]ethanoate as an oil: [α]D=−21.174 (10.165 mg/cc in MeOH); $^1$H NMR (CDCl$_3$) δ 1.3 (m, 2H), 1.4 (s, 9H), 1.6 (m, 8H), 2.42 (s, 1H), 3.5 (d, 2H), 3.96 (m, 4H), 4.38 (q, 1H), 4.58 (m, 1H), 4.66 (t, 1H), 5.72 (m, 1H), 5.78 (dd, 1H), 6.03 (m, 1H), 6.16 (dd, 1H), 6.33 (dd, 1H), 6.58 (dd, 1H), 6.88 (m, 4H) ppm.

B. In a similar manner, other compounds of formula (IIb) are prepared.

EXAMPLE 3

Compounds of Formula (IIc) and Formula (IId)

A. A solution of 1,1-dimethylethyl [[(2S,3R)-3-[(1E,3E,7E,9S)-10-(4-fluorophenoxy)-9-hydroxyl-1,3,7-decatrien-5-ynyl]-1,4-dioxaspiro[4,5]dec-2-yl]methoxy] ethanoate (1 g, 2.8 mmol) in acetic acid (50 mL) was diluted with ethyl acetate (50 mL) and placed in a 55° C. oil bath for 20 hours. The reaction was complete by TLC analysis. Acetic acid and ethyl acetate were removed by distillation under high vacuum. The residue was diluted with water and extracted with ethyl acetate (3×). The combined organic layers were washed with water, saturated aqueous sodium carbonate, water, and brine solution, dried and concentrated to give 0.9 g of an oil. Chromatography on an HP-20 column eluting with a gradient of methanol in water gave (5S,6R,7E,9E,13E,15S)-16-(4-fluorophenoxy)-5,6,15-trihydroxy-3-oxahexadeca-7,9,13-trien-11-ynoic acid, t-butyl ester (a compound of formula (IIc)). The combined fractions were treated with 1 N sodium hydroxide solution (2 mL) and concentrated. The reaction was complete by TLC after about 1 h and placed on an HP20 column. Chromatography using a gradient of methanol in water gave 0.3 g of (5S,6R,7E,9E,13E,15S)-16-(4-fluorophenoxy)-5,6,15-trihydroxy-3-oxahexadeca-7,9,13-trien-11-ynoic acid; which solidified upon standing; $^1$H NMR (CD$_3$OD) δ 3.63 (m, 2H), 3.667 (m, 1H), 3.91 (m, 2H), 4.113 (s, 2H), 4.150, (t, 1H), 4.498, (m, 1H), 5.762 (dd, 1H), 5.953 (dd, 1H), 6.003 (dt, 1H), 6.202 (dd, 1H), 6.380 (dd, 1H), 6.596 (dd, 1H), 6.928 (m, 2H), 6.988 (m, 2H) ppm.

B. In a similar manner, other compounds of formula (IIc) and formula (IId) are prepared.

EXAMPLE 4

Compounds of Formula (I)

A. Activated zinc was prepared from 10 g of zinc and the reduction carried out using the procedure described in *Helv. Chim. Acta* (1987), Vol. 70, p. 1025). A solution of (5S,6R,7E,9E,13E,15S)-16-(4-fluorophenoxy)-5,6,15-trihydroxy- 3-oxahexadeca-7,9,13-trien-11-ynoic acid, methyl ester, (0.8 g, 1.2 mmol) in methanol (4 mL) was added to a slurry of activated zinc in 1:1 methanol:water (45 mL). The flask was stirred vigorously under nitrogen for 24–60 hours. The mixture was filtered through a pad of Celite 545 and rinsed with methanol (3×25 mL). Purification by chromatography on a reverse phase semi-prep column using a gradient of acetonitrile and water afforded 55 mg of (5S,6R,7E,9E,11Z,13E,15S)-16-(4-fluorophenoxy)-5,6,15-trihydroxy-3-oxa-7,9,11,13-hexadecatetraenoic acid, methyl ester, as an oil; $^1$H-NMR (400 mHz, methanol-$d_4$) δ 3.62 (m, 2H), 3.75 (s, 3H), 3.93 (m, 2H), 4.13 (m, 3H), 4.58 (m, 1H), 5.85 (m, 2H), 6.14 (m, 2H), 6.36 (m, 2H), 6.77 (m, 1H), 6.96 (m, 5H) ppm.

B. In a similar manner, other compounds of formula (I) may be prepared:

C. A solution of (5S,6R,7E,9E,11Z,13E,15S)-16-(4-fluorophenoxy)-5,6,15-trihydroxy-3-oxa-7,9,11,13-hexadecatetraenoic acid, methyl ester, (25 mg, 59 nMol) in methanol (6 mL) was treated with 1 N NaOH (aq) (25 μL, 25 μmol) solution and shaken and allowed to stand. Upon completion, the reaction was treated with saturated potassium monophosphate. Purification by chromatography on an HP20 column eluted with an aqueous methanol gradient gave 10 mg of (5S,6R,7E,9E,11Z,13E,15S)-16-(4-fluorophenoxy)-5,6,15-trihydroxy-3-oxa-7,9,11,13-hexadecatetraenoic acid; $^1$H NMR (CD$_3$OD) δ 3.6 (m, 3H), 3.88 (m, 4H), 4.18 (m, 1H), 4.52 (m, 1H), 5.84 (m, 2H), 6.03 (m, 2H), 6.34 (m, 2H), 6.74 (m, 1H), 6.95 (m, 5H) ppm.

D. In a similar manner as described above, the following compounds of formula (I) are prepared:
(2E,5S,6R,7E,9E,11Z,13E,15)-16-(4-fluorophenoxy)-5,6,15-trihydroxyhexa-2,7,9,11,13-decapentaenoic acid;
(2E,5S,6R,7E,9E,11Z,13E,5S)-16-(4-fluorophenoxy)-5,6,15-trihydroxyhexa-2,7,9,11,13-decapentaenoic acid, methyl ester;
(5R,6R,7E,9E,11Z,13E,15S)-16-(4-fluorophenoxy)-5,6,15-trihydroxy-3-oxa-7,9,11,13-hexadecatetraenoic acid;
(5R,6R,7E,9E,11Z,13E,15S)-16-(4-fluorophenoxy)-5,6,15-trihydroxy-3-oxa-7,9,11,13-hexadecatetraenoic acid, methyl ester;
(5S,6R,7E,9E,11Z,13E,15S)-16-(4-fluorophenoxy)-5,6,15-trihydroxy-3-oxa-7,9,11,13-hexadecatetraenamide;
(5S,6R,7E,9E,11Z,13E,15S)-16-(4-fluorophenoxy)-5,6,15-trihydroxy-N,N-dimethyl-3-oxa-7,9,11,13-hexadecatetraenamide;
(7S,8R,9E,11E,13Z,15E,17S)-18-(4-fluorophenoxy)-7,8,17-trihydroxy-5-oxa-9,11,13,15-octadecatetraenoic acid;
(7S,8R,9E,11E,13Z,15E,17S)-18-(4-fluorophenoxy)-7,8,17-trihydroxy-5-oxa-9,11,13,15-octadecatetraenoic acid, methyl ester;
(5S,6R,7E,9E,11Z,13E,15S)-16-(4-fluorophenoxy)-5,6,15-trihydroxy-3-thia-7,9,11,13-hexadecatetraenoic acid;
(5S,6R,7E,9E,11Z,13E,15S)-16-(4-fluorophenoxy)-5,6,15-trihydroxy-3-aza-7,9, 11,13-hexadecatetraenoic acid;
(5S,6R,7E,9E,11Z,13E,15S)-16-(4-fluorophenoxy)-5,15-dihydroxy-6-(methylamino)-3-oxa-7,9,11,13-hexadecatetraenoic acid; and
(5S,6R,7E,9E,11Z,13E,15S)-16-(4-fluorophenoxy)-5,15-dihydroxy-6-amino-3-oxa-7,9,11,13-hexadecatetraenoic acid.

EXAMPLE 5

This example illustrates the preparation of representative pharmaceutical compositions for oral administration containing a compound of the invention, as a single stereoisomer, a mixture of stereoisomers, or as a racemic mixture of stereoisomers; or as a cyclodextrin clathrate thereof, or as a pharmaceutically acceptable salt thereof:

| A. Ingredients | % wt./wt. |
| --- | --- |
| Compound of the invention | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. Ingredients | % wt./wt. |
| --- | --- |
| Compound of the invention | 20.0% |
| Magnesium stearate | 0.9% |
| Starch | 8.6% |
| Lactose | 69.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. Ingredients | |
| --- | --- |
| Compound of the invention | 0.1 g |
| Propylene glycol | 20.0 g |
| Polyethylene glycol 400 | 20.0 g |
| Polysorbate 80 | 1.0 g |
| Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. Ingredients | % wt./wt. |
| --- | --- |
| Compound of the invention | 20.0% |
| Peanut Oil | 78.0% |
| Span 60 | 2.0% |

The above ingredients are melted, mixed and filled into soft elastic capsules.

| E. Ingredients | % wt./wt. |
| --- | --- |
| Compound of the invention | 1.0% |
| Methyl or carboxymethyl cellulose | 2.0% |
| 0.9% saline | q.s. 100 mL |

The compound of the invention is dissolved in the cellulose/saline solution, filtered and bottled for use.

EXAMPLE 6

This example illustrates the preparation of a representative pharmaceutical formulation for parenteral administration containing a compound of the invention, as a single stereoisomer, a mixture of stereoisomers, or as a racemic mixture of stereoisomers; or as a cyclodextrin clathrate thereof, or as a pharmaceutically acceptable salt thereof:

| Ingredients | |
| --- | --- |
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 7

This example illustrates the preparation of a representative pharmaceutical composition in suppository form containing a compound of the invention, as a single stereoisomer, a mixture of stereoisomers, or as a racemic mixture of stereoisomers; or as a cyclodextrin clathrate thereof, or as a pharmaceutically acceptable salt thereof:

| Ingredients | % wt./wt. |
| --- | --- |
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 8

This example illustrates the preparation of a representative pharmaceutical formulation for insufflation containing a compound of the invention, as a single stereoisomer, a mixture of stereoisomers, or as a racemic mixture of stereoisomers; or as a cyclodextrin clathrate thereof, or as a pharmaceutically acceptable salt thereof:

| Ingredients | % wt./wt. |
| --- | --- |
| Micronized compound of the invention | 1.0% |
| Micronized lactose | 99.0% |

The ingredients are milled, mixed, and packaged in an insufflator equipped with a dosing pump.

EXAMPLE 9

This example illustrates the preparation of a representative pharmaceutical formulation in nebulized form containing a compound of the invention, as a single stereoisomer, a mixture of stereoisomers, or as a racemic mixture of stereoisomers; or as a cyclodextrin clathrate thereof, or as a pharmaceutically acceptable salt thereof:

| Ingredients | % wt./wt. |
| --- | --- |
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 10

This example illustrates the preparation of a representative pharmaceutical formulation in aerosol form containing a compound of the invention, as a single stereoisomer, a mixture of stereoisomers, or as a racemic mixture of stereoisomers; or as a cyclodextrin clathrate thereof, or as a pharmaceutically acceptable salt thereof:

| Ingredients | % wt./wt. |
| --- | --- |
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 11

In Vitro Assay

Trans-Epithelial and Trans-Endothelial Migration Assays

Culture of Human Umbilical Vein Endothelial Cells (HUVEC):

Human umbilical vein endothelial cells (HUVEC) were cultured according to the methods disclosed in Serhan, C. N., et al., *Biochemistry* (1995), Vol. 34, No. 44, pp. 14509–14615. In particular, HUVEC were used at passages 1 and 2 and were isolated by collegenase digestion (0.1% collagenase, CLS3; Worthington Biochem. Corp., Freehold, N.J.) and propagated on gelatin-coated (1%) tissue culture plates (Costar Corp., Cambridge, Mass.) in RPMI 1640 cell culture medium (BioWhittaker Inc., Walkersville, Md.) supplemented with 15% bovine calf serum (BCS) (Hyclone Laboratories, Logan, Utah), 15% NU-serum (Collaborative Research Inc., Lexington, Mass.), 50 µg/mL endothelial mitogen (Biomedical Technologies Inc., Stoughton, Mass.), 8 units/mL heparin, 50 units/mL penicillin, and 50 µg/mL streptomycin. For transmigration assays HUVEC were seeded and grown to confluence on gelatin-coated (1%) polycarbonate permeable supports (inserts) with a surface area of 0.33 cm$^2$ (Costar Inc., Cambridge, Mass.).

Epithelial Cell Culture:

$T_{84}$ cells were grown in a 1:1 mixture of Dulbecco's modified Eagle medium and Hams F-12 medium supplemented with 15 mM HEPES buffer (pH 7.5), 14 mM NaHCO$_3$, 40 µg/mL penicillin, 8 µg/mL ampicillin, 90 µg/mL streptomycin, and 5% newborn calf serum (Dharmasathaphorn et al., 1990). For apical-to-basolateral transmigration experiments, $T_{84}$ monolayers were grown on collagen-coated, polycarbonate permeable supports (inserts) with a surface area of 0.33 cm$^2$ (Costar Inc., Cambridge, Mass.) as described in Parkos, C. A., et al., *J. Clin. Invest.* (1991), Vol. 88, pp. 1605–1612. For physiologically directed, basolateral-to-apical neutrophil transmigration experiments, $T_{84}$ cells were plated on the underside of 0.33 cm$^2$ polycarbonate filters that had been lightly coated with rat-tail collagen as described in Parkos, C. A., et al. This permitted growth of inverted monolayers, which thus allowed neutrophils to settle by gravity into the immediate subepithelial compartment.

Assay:

Human polymorphonuclear leukocytes (PMN) were isolated from normal human volunteers and suspended at a concentration of 5×10$^7$ cells/mL in modified Hanks balanced salt solution (HBSS), without Ca$^{2+}$ and Mg$^{2+}$, with 10 mM Hepes, pH 7.4, (Sigma). Prior to the addition of PMN, $T_{84}$ epithelial or HUVEC endothelial cell monolayers were extensively rinsed in HBSS to remove residual serum components. PMN were pre-exposed to compounds of the invention at concentrations ranging from 10$^{-11}$ to 10$^{-7}$ M for 15 minutes at 25° C. The transmigration assay was performed by the addition of PMN (40 µl) to HBSS (containing Ca$^{2+}$ and Mg$^{2+}$, 160 µl) in the upper chambers after chemoattractant (10 nM fMLP) was added to the opposing (lower) chambers. PMN were not washed free of the compounds of the invention prior to addition to monolayers. PMN (1×106) were added at time 0. Transmigration was allowed to proceed for 60 minutes. All experiments were performed in a 37° C. environment to ensure that endothelial/epithelial monolayers, solutions, plasticware, etc., were maintained at uniform 37° C. temperature. Transmigration was quantitated by assaying for the PMN azurophilic granule marker myeloperoxidase (MPO). Following each transmigration assay, non-adherent PMN were extensively washed from the surface of the monolayer and PMN cell equivalents (PMN CE), estimated from a standard curve, were assessed as the number of PMN which had completely traversed the monolayer (i.e., across the monolayer into the reservoir bath).

The compounds of the invention, when tested in this assay, demonstrated the ability to inhibit the transmigration of PMN across polarized monolayers of epithelial cells and vascular endothelial cells, which are sites of two important immune events in host defense and inflammation.

EXAMPLE 12

In Vivo Assay

Chemotaxis Assay

Chemotaxis experiments were performed on freshly prepared human neutrophils (PMN) obtained from whole blood donated by healthy volunteers. Blood was anticoagulated (heparin), centrifuged at low speed and platelet-rich plasma removed by aspiration. The remaining blood was mixed with an equal volume of phosphate buffered saline minus Ca$^{+2}$/Mg$^{+2}$, pH 7.4 (PBS$^{-/-}$) and an equal volume of 3% dextran in PBS$^{-/-}$ was added, sample mixed and allowed to settle. The upper layer enriched for white blood cells (~25 mL) was applied to a 15 mL cushion of Ficoll-Hypaque and centrifuged at 400 g for 30 minutes at 18–22° C. The upper layers were aspirated and the PMN cell pellet subjected to hypotonic red blood cell lysis. PMN were washed twice and resuspended in Hank's Balanced Salt Solution minus Ca$^{+2}$/Mg$^{+2}$ pH 7.4 (HBSS$^{-/-}$) at 1×10$^7$ cells/mL in a centrifuge tube. 2.5 µM Calcein-AM (Molecular Probes cat #C3100) was added and the cells incubated for 25 minutes at ambient temperature, then placed in a 37° C. incubator for 5 minutes. The cells were then centrifuged and washed twice in HBSS$^{-/-}$ to remove residual Calcein-AM. Neutrophils were finally resuspended at 2×10$^7$/mL with HBSS$^{-/-}$+10 mM HEPES, pH 7.4.

Chemotaxis assays were performed with specialized 96-well plates. The 3 µm filter was bonded to a metallic frame and was selectively coated with a hydrophobic mask around each well. This hydrophobic mask allowed for the direct addition of cells to the topside of the filter. Neutrophils (15 µL, 1.5×10$^5$ cells/well) were added to the top of the ChemoTx® plate (Cat #101-3). For inhibition studies, PMN were pre-incubated for 15 minutes with a compound of the invention. Prior to adding PMN to the top chamber, 30 µL of chemoattractant (10 nM FMLP or 10 nM LTB$_4$ or F-12 culture medium (without phenol red) was added to the lower chamber, the filter mat was then snapped in place and PMN added to the filter with an 8-channel pipettor. The assay plates were incubated for 90 minutes at 5% CO$_2$+95% air at 37° C. After incubation, the filter mat was removed and the plate was read in the Victor II plate reader (485 nm-excitation/535 nm emission). The fluorescently tagged cells that have migrated through the filter into the lower chamber were measured.

When tested in this assay, the compounds of the invention demonstrated the ability to inhibit human neutrophil chemotaxis.

EXAMPLE 13

In Vivo Assay

Mouse Zymosan-Induced Peritonitis Model

The following assay was used to evaluate the ability of the compounds of the invention to inhibit inflammation characterized by cellular infiltration into a localized area.

A compound of the invention in 0.1% ethanol/PBS vehicle was administered via intravenous, intra-peritoneal, subcutaneous or intra-gastric delivery to six to eight week-old FVB mice (average 21 g) purchased from Charles River Laboratories. For intra-gastric studies, 200 µL of each compound concentration were delivered using animal feeding needles. Approximately forty-five minutes later, 1 mL (1 mg/mL) zymosan A was injected into the peritoneum. Two and a half hours after the intra-peritoneal injection, mice were euthanized with an overdose of isoflurane and peritoneal lavages with 5 mL of PBS containing calcium and magnesium were collected. Total leukocytes were enumerated by light microscopy and percentage inhibition relative to vehicle control is calculated. For differential inhibitory effects on neutrophils, eosinophils, monocytes and lymphocytes, ~250,000 cells were transferred to glass slides and stained with 0.4% of Wright Giemsa Stain, differentiated by counting under a microscope (×40) and percentage inhibition relative to vehicle control calculated.

When tested in this assay, the compounds of the invention demonstrated the ability to inhibit the migration of inflammatory cells (i.e., neutrophiles, monocytes and lymphocytes) into the peritoneum. Accordingly, the compounds of the invention were shown to be useful in treating an inflammatory disorder in an in vivo model.

EXAMPLE 14

In Vivo Assay

The following assay may be performed in a similar manner as the assay described in Campbell, E. M., et al., *J. Immunol.* (1998), Vol. 161, No. 12, p. 7047–7053.

The assay utilizes CBA/J mice sensitized with soluble cockroach antigents in incomplete Freund's adjuvant intraperitoneally. The assay uses 6–8 animals in each group/time point, including a group for controls. After 14 days, the mice are sensitized again sensitized with soluble cockroach antigen by an intranasal administration, followed 3–5 days later with an intratracheal injection of cockroach antigen. The mice can be given a second intratracheal challenge at 48 hrs post-primary. Prior to the final challenge, the allergic mice receive one of 3 doses of a compound of the invention. After 8 and 24 hours post-challenge, the mice are examined for airway hyperreactivity and the accumulation of leukocyte subsets are monitored in the bronchoalveolar lavage (BAL) and in histologic sections. The second challenge is given at a time when there is a considerable amount of inflammation found within and around the airway, including eosinophils. This scenario is representative of what occurs in chronic asthmatics. This chronic stage response is much more severe and has significantly higher levels of leukocyte infiltration and a synergistic increase in the numbers and activation of eosinophils. This inflammation is dependent upon Th2 type immune responses. This analysis allows for the identification of whether a compound of the invention can attenuate the responses, i.e., leukocyte migration and the clinically relevant airway physiology.

In addition to the above analysis, various samples collected from the study, including the BAL fluid and lung tissue, further analysis may be performed to determine the manner in which the compounds of the invention are attenuating the responses. Specifically, cytokine (IL-4, IL-5, IL-10, IL-13, IL-18, TNF, IFN, etc) levels in the BAL fluid and the lung tissue homogenates can be analyzed, as well as histamine and eosinophil peroxidase levels (see Wu, W., et al., *Journal of Clinical Investigation* (2000), Vol. 105, pp. 1455–1463).

Animals:

Female C57/BL6 mice were purchased from either The Jackson Laboratory, (Bar Harbor, Me.) or Charles River Breeding Laboratories (Wilmington, Mass.) and were maintained under standard pathogen-free conditions. All materials were obtained from Sigma Chemical Company (St. Louis, Mo.) unless otherwise indicated.

Sensitization and Induction of the Airway Response:

Normal C57/BL6 mice were immunized with 10 μg of cockroach allergen (Bayer) in IFA on day 0. In order to localize the response to the lung, the mice were given an intranasal administration of 10 μg of cockroach allergen in 10 μL of diluent on day 14. This initial intranasal allergen induced little cellular infiltrate into the lungs of the mice upon histological examination. Mice were then challenged 6 days later (referred to hereafter as primary challenge response) by intratracheal administration of 10 μg of cockroach allergen in 50 μL of sterile PBS or with PBS alone (vehicle). The magnitude of leukocyte recruitment in both the vehicle control and cockroach allergen-challenged mice was examined histologically. Only the cockroach allergen-challenged mice displayed a significant inflammatory response that included mononuclear cell and eosinophil infiltration. Some mice were given a second intratracheal injection of either cockroach allergen (10 μg in 50 μL) or diluent control and subsequently analyzed (secondary rechallenge response). In separate studies, the effect of the anti-murine MIP-1α and anti-murine eotaxin polyclonal antibodies on cockroach allergen-induced responses were assessed by giving sensitized mice an i.p. dose of the antibody (0.5 mL, titers of $10^6$/mL) at 1 hour prior to each allergen challenge. Normal rabbit serum (NRS) was used as a control. Polyclonal antibodies had previously been demonstrated to block the chemotaxis of murine eosinophils in vitro.

Measurement of Airway Hyperactivity:

Airway hyperactivity was measured using Buxco mouse plethysmograph, which is specifically designed for the low tidal volumes (Buxco) as previously described in Lukacs, N. W., et al., *J. Immunol.* (1992), Vol. 13, pp. 501. Briefly, the mouse to be tested was anesthetized with sodium pentobarbital and incubated via cannulation of the trachea with an 18-gauge metal tube. The mouse was subsequently ventilated with a Harvard pump ventilator (tidal volume=0.4 mL, frequency=120 breaths/min., positive end-expiatory pressure 2.5 to 3.0 cm $H_2O$ and the tail vein was cannulated with a 27-gauge needle for injection of the methacholine challenge. The plethysmograph was sealed and readings were monitored by computer. Since the box was a closed system, a change in lung volume was represented by a change in box pressure ($P_{box}$), which was measured by a differential transducer. The system was calibrated with a syringe that delivered a known volume of 2 mL. A second transducer was used to measure the pressure swings at the opening of the trachea tube ($P_{aw}$), referenced to the body box (i.e., pleural pressure, and to provide a measure of transpulmonary pressure ($P_{tp}=P_{aw}-P_{box}$). The trachea transducer was calibrated at a constant pressure of 20 cm $H_2O$. Resistance was calculated by the Buxco software by dividing the change in pressure ($P_{tp}$) by the change in flow (F) ($\delta P_{tp}/\delta F$; units=cm $H_2O$/mL/s) at two time points from the volume curve, based upon a percentage of the inspiratory volume. Once the mouse was hooked up to the box it was ventilated for 5 minutes prior to acquiring readings. Once baseline levels were stabilized and initial readings were taken, a methacholine challenge was given via the cannulated tail vein. After determining a dose-response curve (0.001 to 0.5 mg), an optimal dose was chosen (0.1 mg of methacholine) which was used throughout the rest of the experiments in this study. After the methacholine challenge, the response was monitored and the peak airway resistance was recorded as a measure of airway hyperactivity.

Compounds of the invention, when tested in the above assay, demonstrated the ability to decrease airway resistance in an animal model for asthma.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula (II):

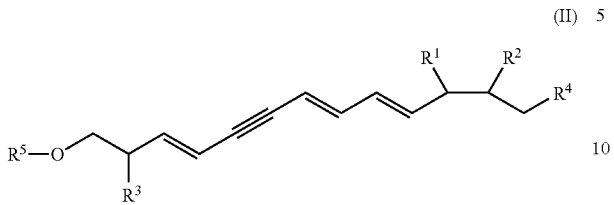

wherein:
each $R^1$, $R^2$ and $R^3$ are independently halo, $-OR^6$, $-SR^6$, $-S(O)_tR^7$ (where t is 1 or 2) or $-N(R^7)R^8$;
or $R^1$ and $R^2$ together with the carbons to which they are attached form a monocyclic heterocyclic structure selected from the following:

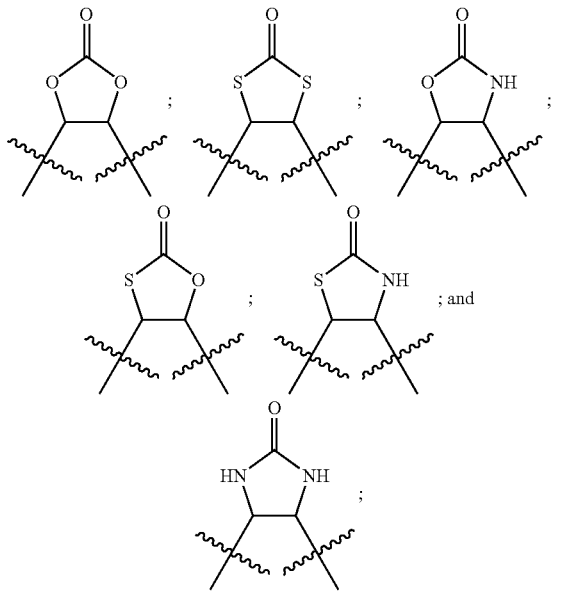

or $R^1$ and $R^2$ together with the carbons to which they are attached form the following bicyclical heterocyclic structure:

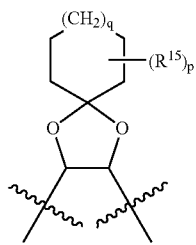

(where q is 0 to 3, p is 1 to 4 and each $R^{15}$ is hydrogen, alkyl, aralkyl or aryl);
each $R^4$ is $-R^9-R^{12}$, $-R^9-R^{13}-R^{11}$, $-R^9-O-R^{10}-R^{11}$, $-R^9-O-R^{12}$, $-R^9-C(O)-R^{10}-R^{11}$, $-R^9-N(R^7)-R^{10}-R^{11}$, $-R^9-S(O)_t-R^{10}-R^{11}$ (where t is 0 to 2), or $-R^9-C(F)_2-R^9-R^{11}$;

each $R^5$ is aryl (optionally substituted by one or more substituents selected from the group consisting of alkyl, alkoxy, halo, haloalkyl and haloalkoxy) or aralkyl (optionally substituted by one or more substituents selected from the group consisting of alkyl, alkoxy, halo, haloalkyl and haloalkoxy);
each $R^6$ is independently hydrogen, alkyl, aryl, aralkyl, $-C(O)R^7$, $-C(S)R^7$, $-C(O)OR^{14}$, $-C(S)OR^{14}$, $-C(O)N(R^7)R^8$, or $-C(S)N(R^7)R^8$;
each $R^7$ is independently hydrogen, alkyl, cycloalkyl, aryl, or aralkyl;
$R^8$ is independently hydrogen, alkyl, aryl, aralkyl, $-C(O)R^7$, $-C(O)OR^{14}$, or cycloalkyl (optionally substituted with one more substituents selected from the group consisting of alkyl, $-N(R^7)_2$, and $-C(O)OR^7$);
each $R^9$ is independently a direct bond or a straight or branched alkylene chain;
each $R^{10}$ is independently a straight or branched alkylene chain, a straight or branched alkenylene chain, a straight or branched alkynylene chain or a cycloalkylene;
each $R^{11}$ is independently $-C(O)OR^7$, $-C(O)N(R^7)_2$, $-P(O)(OR^7)_2$, $-S(O)_2OR^7$, $-S(O)_2N(H)R^7$ or tetrazole;
$R^{12}$ is aryl (substituted by $-C(O)OR^7$ or $-C(O)N(R^7)_2$ and optionally by one or more substituents selected from the group consisting of alkyl, alkoxy, halo, haloalkyl and haloalkoxy) or aralkyl (substituted by $-C(O)OR^7$ or $-C(O)N(R^7)_2$ and optionally by one or more substituents selected from the group consisting of alkyl, alkoxy, halo, haloalkyl and haloalkoxy);
$R^{13}$ is a branched alkylene chain, a straight or branched alkenylene chain or a cycloalkylene; and
$R^{14}$ is alkyl, aryl or aralkyl;
as a single stereoisomer, a mixture of stereoisomers, a racemic mixture of stereoisomers; or as a cyclodextrin clathrate thereof, or as a pharmaceutically acceptable salt thereof.

2. The compound of claim 1 wherein:
$R^1$, $R^2$ and $R^3$ are each independently halo, $-OR^6$, $-SR^6$ or $-N(R^7)R^8$;
each $R^4$ is $-R^9-R^{12}$, $-R^9-R^{13}-R^{11}$, $-R^9-O-R^{10}-R^{11}$, $-R^9-O-R^{12}$, $-R^9-C(O)-R^{10}-R^{11}$, $-R^9-N(R^7)-R^{10}-R^{11}$, $-R^9-S(O)_t-R^{10}-R^{11}$ (where t is 0 to 2), or $-R^9-C(F)_2-R^9-R^{11}$;
$R^5$ is aryl (optionally substituted by one or more substituents selected from the group consisting of alkyl, alkoxy, halo, and haloalkoxy) or aralkyl (optionally substituted by one or more substituents selected from the group consisting of alkyl, alkoxy, halo, and haloalkoxy);
each $R^6$ is independently hydrogen, alkyl, aralkyl, $-C(O)R^7$ or $-C(O)OR^7$;
each $R^7$ is independently hydrogen, alkyl, aryl, or aralkyl;
$R^8$ is independently hydrogen, alkyl, aryl, aralkyl, or cycloalkyl (optionally substituted with one more substituents selected from the group consisting of alkyl, $-N(R^7)_2$, and $-C(O)OR^7$);
each $R^9$ is independently a direct bond or a straight or branched alkylene chain;
each $R^{10}$ is independently a straight or branched alkylene chain, a straight or branched alkenylene chain, a straight or branched alkynylene chain or a cycloalkylene;
each $R^{11}$ is independently $-C(O)OR^7$ or $-C(O)N(R^7)_2$;
$R^{12}$ is aryl (substituted by $-C(O)OR^7$ or $-C(O)N(R^7)_2$ and optionally by one or more substituents selected from the group consisting of alkyl, alkoxy, halo and haloalkoxy) or aralkyl (substituted by —C(O)OR$^7$ or —C(O)N(R$^7$)$_2$ and optionally by one or more substituents selected from the group consisting of alkyl, alkoxy, halo and haloalkoxy);

R$^{13}$ is a branched alkylene chain, a straight or branched alkenylene chain or a cycloalkylene.

3. The compound of claim 2 wherein:
R$^1$, R$^2$ and R$^3$ are each independently halo, —OR$^6$, or —SR$^6$;
R$^4$ is —R$^9$—O—R$^{10}$—R$^{11}$;
R$^5$ is aryl (optionally substituted by one or more substituents selected from the group consisting of alkyl, alkoxy, halo, and haloalkoxy) or aralkyl (optionally substituted by one or more substituents selected from the group consisting of alkyl, alkoxy, halo, and haloalkoxy);
each R$^6$ is independently hydrogen, alkyl, aryl, or aralkyl;
each R$^7$ is independently hydrogen, alkyl, aryl, or aralkyl;
R$^9$ is a direct bond or a straight or branched alkylene chain;
R$^{10}$ is an straight or branched alkylene chain, a straight or branched alkenylene chain, a straight or branched alkynylene chain or a cycloalkylene; and
R$^{11}$ is —C(O)OR$^7$ or —C(O)N(R$^7$)$_2$.

4. The compound of claim 3 wherein:
R$^1$, R$^2$ and R$^3$ are each —OR$^6$;
R$^4$ is —R$^9$—O—R$^{10}$—R$^{11}$;
R$^5$ is aryl (optionally substituted by one or more substituents selected from the group consisting of alkyl, alkoxy, halo, and haloalkoxy);
R$^6$ is hydrogen, alkyl, aryl, or aralkyl;
each R$^7$ is independently hydrogen, alkyl, aryl, or aralkyl;
R$^9$ is a direct bond;
R$^{10}$ is a straight or branched alkylene chain, a straight or branched alkenylene chain, or a straight or branched alkynylene chain; and
R$^{11}$ is —C(O)OR$^7$ or —C(O)N(R$^7$)$_2$.

5. The compound of claim 4 selected from the group consisting of:
(5S,6R,7E,9E,13E,15S)-16-(4-fluorophenoxy)-5,6,15-trihydroxy-3-oxahexadeca-7,9,13-trien-11-ynoic acid, methyl ester;
(5S,6R,7E,9E,13E,15S)-16-(4-fluorophenoxy)-5,6,15-trihydroxy-3-oxahexadeca-7,9,13-trien-11-ynoic acid;
(5S,6S,7E,9E,13E,15S)-16-(4-fluorophenoxy)-5,6,15-trihydroxy-3-oxahexadeca-7,9,13-trien-11-ynoic acid, methyl ester; and
(5S,6S,7E,9E,13E,15S)-16-(4-fluorophenoxy)-5,6,15-trihydroxy-3-oxahexadeca-7,9,13-trien-11-ynoic acid.

6. A pharmaceutical composition comprising one or more pharmaceutically acceptable excipient(s) and a therapeutically effective amount of a compound of formula (II):

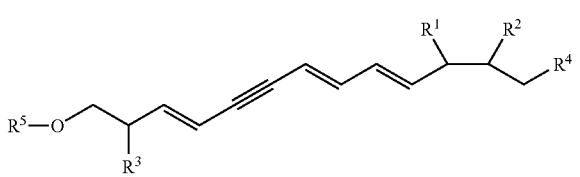

(II)

wherein:
each R$^1$, R$^2$ and R$^3$ are independently halo, —OR$^6$, —SR$^6$, —S(O)$_t$R$^7$ (where t is 1 or 2) or —N(R$^7$)R$^8$;

or R$^1$ and R$^2$ together with the carbons to which they are attached form a monocyclic heterocyclic structure selected from the following:

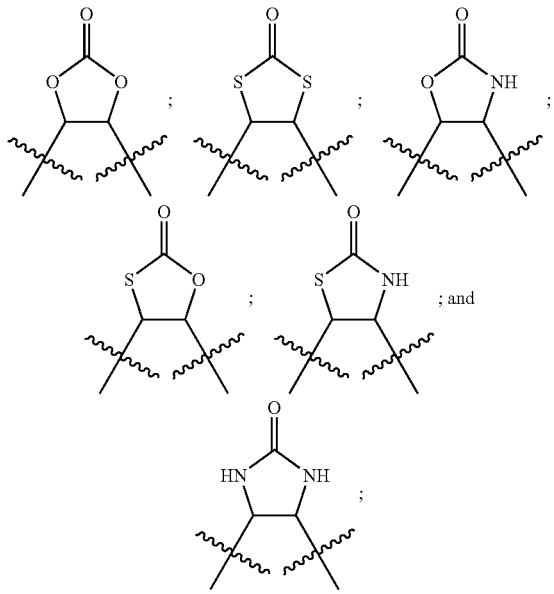

or R$^1$ and R$^2$ together with the carbons to which they are attached form the following bicyclic heterocyclic structure:

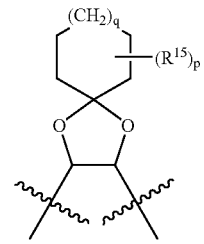

(where q is 0 to 3, p is 1 to 4 and each R$^{15}$ is hydrogen, alkyl, aralkyl or aryl);

each R$^4$ is —R$^9$—R$^{12}$, —R$^9$—R$^{13}$—R$^{11}$, —R$^9$—O—R$^{10}$—R$^{11}$, —R$^9$—O—R$^{12}$, —R$^9$—C(O)—R$^{10}$—R$^{11}$, —R$^9$—N(R$^7$)—R$^{10}$—R$^{11}$, —R$^9$—S(O)$_t$—R$^{10}$—R$^{11}$ (where t is 0 to 2), or —R$^9$—C(F)$_2$—R$^9$—R$^{11}$;

each R$^5$ is aryl (optionally substituted by one or more substituents selected from the group consisting of alkyl, alkoxy, halo, haloalkyl and haloalkoxy) or aralkyl (optionally substituted by one or more substituents selected from the group consisting of alkyl, alkoxy, halo, haloalkyl and haloalkoxy);

each R$^6$ is independently hydrogen, alkyl, aryl, aralkyl, —C(O)R$^7$, —C(S)R$^7$, —C(O)OR$^{14}$, —C(S)OR$^{14}$, —C(O)N(R$^7$)R$^8$, or —C(S)N(R$^7$)R$^8$;

each R$^7$ is independently hydrogen, alkyl, cycloalkyl, aryl, or aralkyl;

R$^8$ is independently hydrogen, alkyl, aryl, aralkyl, —C(O)R$^7$, —C(O)OR$^{14}$, or cycloalkyl (optionally substituted with one more substituents selected from the group consisting of alkyl, —N(R$^7$)$_2$, and —C(O)OR$^7$);

each $R^9$ is independently a direct bond or a straight or branched alkylene chain;

each $R^{10}$ is independently a straight or branched alkylene chain, a straight or branched alkenylene chain, a straight or branched alkynylene chain or a cycloalkylene;

each $R^{11}$ is independently —C(O)OR$^7$, —C(O)N(R$^7$)$_2$, —P(O)(OR$^7$)$_2$, —S(O)$_2$OR$^7$, —S(O)$_2$N(H)R$^7$ or tetrazole;

$R^{12}$ is aryl (substituted by —C(O)OR$^7$ or —C(O)N(R$^7$)$_2$ and optionally by one or more substituents selected from the group consisting of alkyl, alkoxy, halo, haloalkyl and haloalkoxy) or aralkyl (substituted by —C(O)OR$^7$ or —C(O)N(R$^7$)$_2$ and optionally by one or more substituents selected from the group consisting of alkyl, alkoxy, halo, haloalkyl and haloalkoxy);

$R^{13}$ is a branched alkylene chain, a straight or branched alkenylene chain or a cycloalkylene; and $R^{14}$ is alkyl, aryl or aralkyl;

as a single stereoisomer, a mixture of stereoisomers, a racemic mixture of stereoisomers; or as a cyclodextrin clathrate thereof, or as a pharmaceutically acceptable salt thereof.

7. A method of treating an inflammatory or autoimmune disorder in a mammal, wherein the method comprises administering to the mammal in need thereof a therapeutically effective amount of a compound of formula (II):

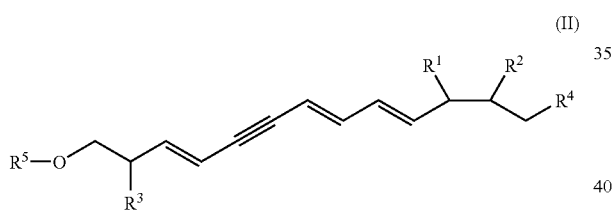

(II)

wherein:
each $R^1$, $R^2$ and $R^3$ are independently halo, —OR$^6$, —SR$^6$, —S(O)$_t$R$^7$ (where t is 1 or 2) or —N(R$^7$)R$^8$;

or $R^1$ and $R^2$ together with the carbons to which they are attached form a monocyclic heterocyclic structure selected from the following:

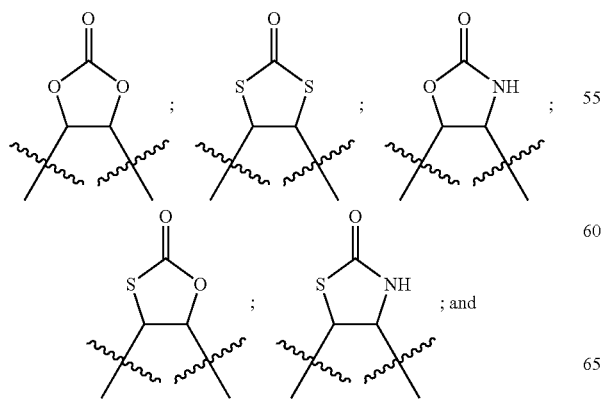

; and

-continued

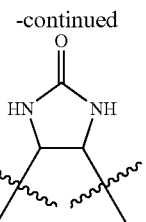

or $R^1$ and $R^2$ together with the carbons to which they are attached form the following bicyclic heterocyclic structure:

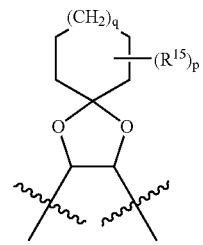

(where q is 0 to 3, p is 1 to 4 and each $R^{15}$ is hydrogen, alkyl, aralkyl or aryl);

each $R^4$ is —R$^9$—R$^{12}$, —R$^9$—R$^{10}$—R$^{11}$, —R$^9$—O—R$^{10}$—R$^{11}$, —R$^9$—O—R$^{12}$, —R$^9$—C(O)—R$^{10}$—R$^{11}$, —R$^9$—N(R$^7$)—R$^{10}$—R$^{11}$, —R$^9$—S(O)$_t$—R$^{10}$—R$^{11}$ (where t is 0 to 2), or —R$^9$—C(F)$_2$—R$^9$—R$^{11}$;

each $R^5$ is aryl (optionally substituted by one or more substituents selected from the group consisting of alkyl, alkoxy, halo, haloalkyl and haloalkoxy) or aralkyl (optionally substituted by one or more substituents selected from the group consisting of alkyl, alkoxy, halo, haloalkyl and haloalkoxy);

each $R^6$ is independently hydrogen, alkyl, aryl, aralkyl, —C(O)R$^7$, —C(S)R$^7$, —C(O)OR$^{14}$, —C(S)OR$^4$, —C(O)N(R$^7$)R$^8$, or —C(S)N(R$^7$)R$^8$;

each $R^7$ is independently hydrogen, alkyl, cycloalkyl, aryl, or aralkyl;

$R^8$ is independently hydrogen, alkyl, aryl, aralkyl, —C(O)R$^7$, —C(O)OR$^{14}$, or cycloalkyl (optionally substituted with one more substituents selected from the group consisting of alkyl, —N(R$^7$)$_2$, and —C(O)OR$^7$);

each $R^9$ is independently a direct bond or a straight or branched alkylene chain;

each $R^{10}$ is independently a straight or branched alkylene chain, a straight or branched alkenylene chain, a straight or branched alkynylene chain or a cycloalkylene;

each $R^{11}$ is independently —C(O)OR$^7$, —C(O)N(R$^7$)$_2$, —P(O)(OR$^7$)$_2$, —S(O)$_2$OR$^7$, —S(O)$_2$N(H)R$^7$ or tetrazole;

$R^{12}$ is aryl (substituted by —C(O)OR$^7$ or —C(O)N(R$^7$)$_2$ and optionally by one or more substituents selected from the group consisting of alkyl, alkoxy, halo, haloalkyl and haloalkoxy) or aralkyl (substituted by —C(O)OR or —C(O)N(R$^7$)$_2$ and optionally by one or more substituents selected from the group consisting of alkyl, alkoxy, halo, haloalkyl and haloalkoxy);

$R^{13}$ is a branched alkylene chain, a straight or branched alkenylene chain or a cycloalkylene; and $R^{14}$ is alkyl, aryl or aralkyl;

as a single stereoisomer, a mixture of stereoisomers, a racemic mixture of stereoisomers; or as a cyclodextrin clathrate thereof, or as a pharmaceutically acceptable salt thereof.

8. The method of claim 7 wherein the mammal is a human.

9. The method of claim 8 wherein the inflammatory or autoimmune disorder is selected from the group consisting of:
allergic contact dermatitis, allergic rhinitis, chemical and non-specific irritant contact dermatitis, urticaria, atopic dermatitis, psoriasis, acute myocardial ischemia and infarction, acute hemorrhagic or ischemic stroke, multiple sclerosis, rheumatoid arthritis, osteoarthritis and systemic lupus erythematosus, acute and chronic organ transplant rejection, transplant arteriosclerosis and fibrosis, hypertension, atherosclerosis, aneurysm, critical leg ischemia, peripheral arterial occlusive disease, Reynaud's syndrome, diabetic nephropathy, diabetic neuropathy, and diabetic retinopathy, delayed neurodegeneration in stroke, Alzheimer's disease, Parkinson's disease, benign prostatic hyperplasia, leukemia, lymphoma, prostate cancer, breast cancer, lung cancer, malignant melanoma, renal carcinoma, head and neck tumors and colorectal cancer.

10. A method of treating pulmonary or respiratory tract inflammation in a mammal, wherein the method comprises adminstering to the mammal in need thereof a therapeutically effective amount of a compound of formula (II):

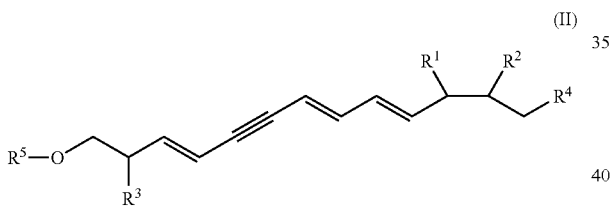

(II)

wherein:
each $R^1$, $R^2$ and $R^3$ are independently halo, —$OR^6$, —$SR^6$, —$S(O)_tR^7$ (where t is 1 or 2) or —$N(R^7)R^8$;
or $R^1$ and $R^2$ together with the carbons to which they are attached form a monocyclic heterocyclic structure selected from the following:

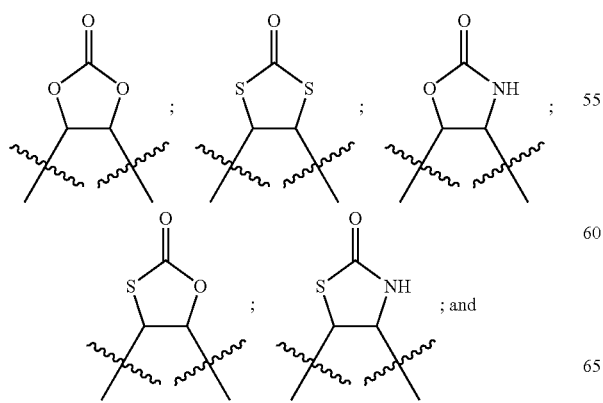

; and

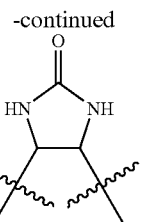

or $R^1$ and $R^2$ together with the carbons to which they are attached form the following bicyclic heterocyclic structure:

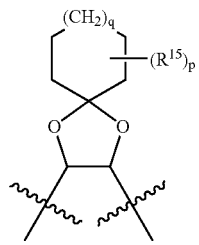

(where q is 0 to 3, p is 1 to 4 and each $R^{15}$ is hydrogen, alkyl, aralkyl or aryl);
each $R^4$ is —$R^9$—$R^{12}$, —$R^9$—$R^{13}$—$R^{11}$, —$R^9$—O—$R^{10}$—$R^{11}$, —$R^9$—O—$R^{12}$, —$R^9$—C(O)—$R^{10}$—$R^{11}$, —$R^9$—N($R^7$)—$R^{10}$—$R^{11}$, —$R^9$—S(O)$_t$—$R^{10}$—$R^{11}$ (where t is 0 to 2), or —$R^9$—C(F)$_2$—$R^9$—$R^{11}$;
each $R^5$ is aryl (optionally substituted by one or more substituents selected from the group consisting of alkyl, alkoxy, halo, haloalkyl and haloalkoxy) or aralkyl (optionally substituted by one or more substituents selected from the group consisting of alkyl, alkoxy, halo, haloalkyl and haloalkoxy);
each $R^6$ is independently hydrogen, alkyl, aryl, aralkyl, —C(O)$R^7$, —C(S)$R^7$, —C(O)O$R^{14}$, —C(S)O$R^{14}$, —C(O)N($R^7$)$R^8$, or —C(S)N($R^7$)$R^8$;
each $R^7$ is independently hydrogen, alkyl, cycloalkyl, aryl, or aralkyl;
$R^8$ is independently hydrogen, alkyl, aryl, aralkyl, —C(O)$R^7$, —C(O)O$R^{14}$, or cycloalkyl (optionally substituted with one more substituents selected from the group consisting of alkyl, —N($R^7$)$_2$, and —C(O)O$R^7$);
each $R^9$ is independently a direct bond or a straight or branched alkylene chain;
each $R^{10}$ is independently a straight or branched alkylene chain, a straight or branched alkenylene chain, a straight or branched alkynylene chain or a cycloalkylene;
each $R^{11}$ is independently —C(O)O$R^7$, —C(O)N($R^7$)$_2$, —P(O)(O$R^7$)$_2$, —S(O)$_2$O$R^7$, —S(O)$_2$N(H)$R^7$ or tetrazole;
$R^{12}$ is aryl (substituted by —C(O)O$R^7$ or —C(O)N($R^7$)$_2$ and optionally by one or more substituents selected from the group consisting of alkyl, alkoxy, halo, haloalkyl and haloalkoxy) or aralkyl (substituted by —C(O)O$R^7$ or —C(O)N($R^7$)$_2$ and optionally by one or more substituents selected from the group consisting of alkyl, alkoxy, halo, haloalkyl and haloalkoxy);
$R^{13}$ is a branched alkylene chain, a straight or branched alkenylene chain or a cycloalkylene; and
$R^{14}$ is alkyl, aryl or aralkyl;

as a single stereoisomer, a mixture of stereoisomers, a racemic mixture of stereoisomers; or as a cyclodextrin clathrate thereof, or as a pharmaceutically acceptable salt thereof.

11. The method of claim 10 wherein the mammal is a human.

12. The method of claim 7 wherein the inflammatory or autoimmune disorder is selected from the group consisting of:

septic or endotoxic shock, hemorrhagic shock, shock-like syndromes, capillary leak syndrome induced by cancer immunotherapy, acute respiratory distress syndrome, traumatic shock, immune- and pathogen-induced pneumonias, immune-complex-mediated pulmonary injury, immune-complex-mediated chronic obstructive pulmonary disease, inflammatory bowel disease, acute renal failure, ischemic bowel disease, immune-complex-mediated glomerulonephritis, insulin-dependent diabetes mellitus, ocular disorders, HIV dementia, encephalitis, inflammatory and neuropathic pain, periodontal disease, and ear infections.

13. The method of claim 12 wherein the inflammatory or autoimmune disorder is an inflammatory bowel disease selected from the group consisting of Crohn's disease, ulcerative colitis and gastrointestinal ulcers.

14. The method of claim 13 wherein the inflammatory bowel disease is Crohn's disease.

15. A method of inhibiting acute or chronic inflammation in a mammal, wherein the method comprises adminstering to the mammal in need thereof a therapeutically effective amount of a compound of formula (II):

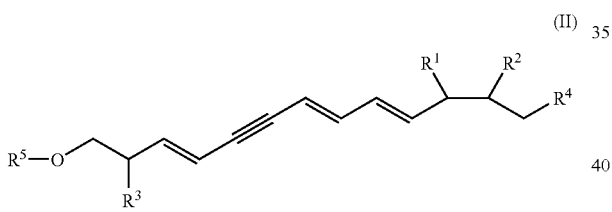

wherein:
each $R^1$, $R^2$ and $R^3$ are independently halo, —$OR^6$, —$SR^6$, —$S(O)_tR^7$ (where t is 1 or 2 ) or —$N(R^7)R^8$;
or $R^1$ and $R^2$ together with the carbons to which they are attached form a monocyclic heterocyclic structure selected from the following:

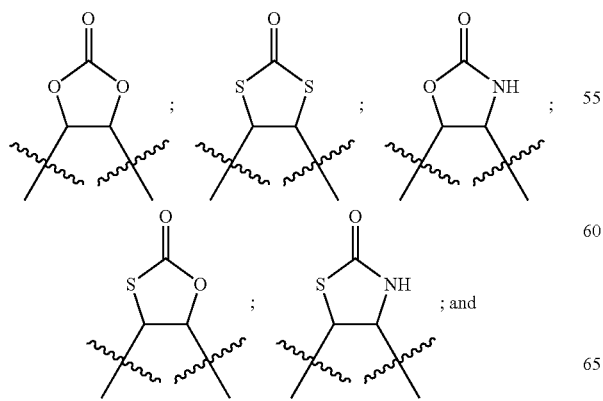

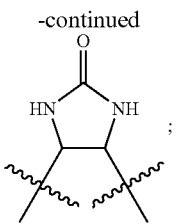

or $R^1$ and $R^2$ together with the carbons to which they are attached form the following bicyclic heterocyclic structure:

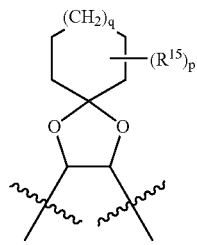

(where q is 0 to 3, p is 1 to 4 and each $R^{15}$ is hydrogen, alkyl, aralkyl or aryl);

each $R^4$ is —$R^9$—$R^{12}$, —$R^9$—$R^{13}$—$R^{11}$, —$R^9$—O— $R^{10}$—$R^{11}$, —$R^9$—O—$R^{12}$, —$R^9$—C(O)—$R^{10}$—$R^{11}$, —$R^9$—N($R^7$)—$R^{10}$—$R^{11}$, —$R^9$—S(O)$_t$—$R^{10}$—$R^{11}$ (where t is 0 to 2), or —$R^9$—C(F)$_2$—$R^9$—$R^{11}$;

each $R^5$ is aryl (optionally substituted by one or more substituents selected from the group consisting of alkyl, alkoxy, halo, haloalkyl and haloalkoxy) or aralkyl (optionally substituted by one or more substituents selected from the group consisting of alkyl, alkoxy, halo, haloalkyl and haloalkoxy);

each $R^6$ is independently hydrogen, alkyl, aryl, aralkyl, —C(O)$R^7$, —C(S)$R^7$, —C(O)$OR^{14}$, —C(S)$OR^{14}$, —C(O)N($R^7$)$R^8$, or —C(S)N($R^7$)$R^8$;

each $R^7$ is independently hydrogen, alkyl, cycloalkyl, aryl, or aralkyl;

$R^8$ is independently hydrogen, alkyl, aryl, aralkyl, —C(O) $R^7$, —C(O)$OR^{14}$, or cycloalkyl (optionally substituted with one more substituents selected from the group consisting of alkyl, —N($R^7$)$_2$, and —C(O)$OR^7$);

each $R^9$ is independently a direct bond or a straight or branched alkylene chain;

each $R^{10}$ is independently a straight or branched alkylene chain, a straight or branched alkenylene chain, a straight or branched alkynylene chain or a cycloalkylene;

each $R^{11}$ is independently —C(O)$OR^7$, —C(O)N($R^7$)$_2$, —P(O)(O$R^7$)$_2$, —S(O)$_2$O$R^7$, —S(O)$_2$N(H)$R^7$ or tetrazole;

$R^{12}$ is aryl (substituted by —C(O)$OR^7$ or —C(O)N($R^7$)$_2$ and optionally by one or more substituents selected from the group consisting of alkyl, alkoxy, halo, haloalkyl and haloalkoxy) or aralkyl (substituted by —C(O)$OR^7$ or —C(O)N($R^7$)$_2$ and optionally by one or more substituents selected from the group consisting of alkyl, alkoxy, halo, haloalkyl and haloalkoxy);

$R^{13}$ is a branched alkylene chain, a straight or branched alkenylene chain or a cycloalkylene; and $R^{14}$ is alkyl, aryl or aralkyl;

as a single stereoisomer, a mixture of stereoisomers, a racemic mixture of stereoisomers; or as a cyclodextrin clathrate thereof, or as a pharmaceutically acceptable salt thereof.

16. A method of inhibiting an inflammatory or autoimmune response in a mammal, wherein the method comprises adminstering to the mammal in need thereof a therapeutically effective amount of a compound of formula (II):

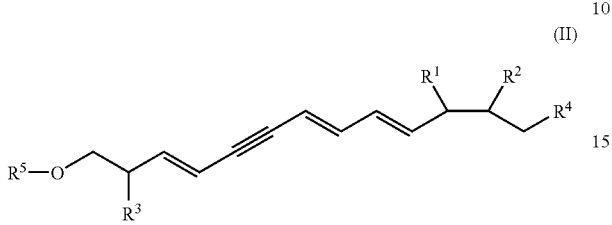

(II)

wherein:
each $R^1$, $R^2$ and $R^3$ are independently halo, —$OR^6$, —$SR^6$, —$S(O)_tR^7$ (where t is 1 or 2) or —$N(R^7)R^8$;
or $R^1$ and $R^2$ together with the carbons to which they are attached form a monocyclic heterocyclic structure selected from the following:

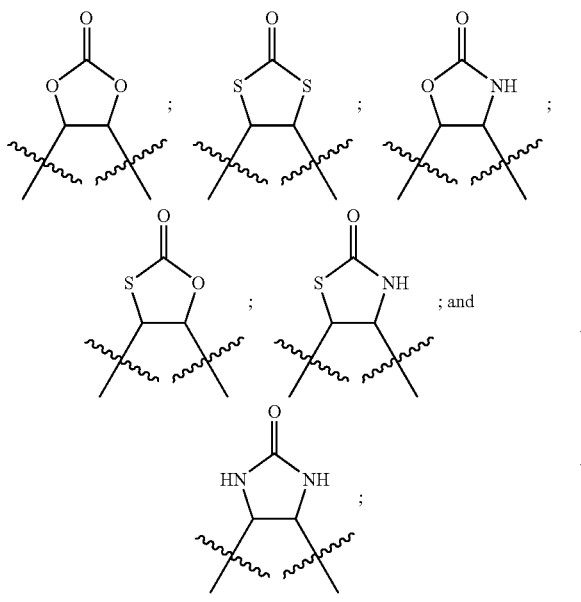

or $R^1$ and $R^2$ together with the carbons to which they are attached form the following bicyclic heterocyclic structure:

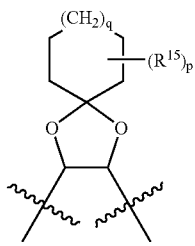

(where q is 0 to 3, p is 1 to 4 and each $R^{15}$ is hydrogen, alkyl, aralkyl or aryl);
each $R^4$ is —$R^9$—$R^{12}$, —$R^9$—$R^{13}$—$R^{11}$, —$R^9$—O—$R^{10}$—$R^{11}$, —$R^9$—O—$R^{12}$, —$R^9$—C(O)—$R^{10}$—$R^{11}$, —$R^9$—N($R^7$)—$R^{10}$—$R^{11}$, —$R^9$—S(O)$_t$—$R^{10}$—$R^{11}$ (where t is 0 to 2), or —$R^9$—C(F)$_2$—$R^9$—$R^{11}$;
each $R^5$ is aryl (optionally substituted by one or more substituents selected from the group consisting of alkyl, alkoxy, halo, haloalkyl and haloalkoxy) or aralkyl (optionally substituted by one or more substituents selected from the group consisting of alkyl, alkoxy, halo, haloalkyl and haloalkoxy);
each $R^6$ is independently hydrogen, alkyl, aryl, aralkyl, —C(O)$R^7$, —C(S)$R^7$, —C(O)$OR^{14}$, —C(S)$OR^{14}$, —C(O)N($R^7$)$R^8$, or —C(S)N($R^7$)$R^8$;
each $R^7$ is independently hydrogen, alkyl, cycloalkyl, aryl, or aralkyl;
$R^8$ is independently hydrogen, alkyl, aryl, aralkyl, —C(O)$R^7$, —C(O)$OR^{14}$, or cycloalkyl (optionally substituted with one more substituents selected from the group consisting of alkyl, —N($R^7$)$_2$, and —C(O)$OR^7$);
each $R^9$ is independently a direct bond or a straight or branched alkylene chain;
each $R^{10}$ is independently a straight or branched alkylene chain, a straight or branched alkenylene chain, a straight or branched alkynylene chain or a cycloalkylene;
each $R^{11}$ is independently —C(O)$OR^7$, —C(O)N($R^7$)$_2$, —P(O)(O$R^7$)$_2$, —S(O)$_2$O$R^7$, —S(O)$_2$N(H)$R^7$ or tetrazole;
$R^{12}$ is aryl (substituted by —C(O)$OR^7$ or —C(O)N($R^7$)$_2$ and optionally by one or more substituents selected from the group consisting of alkyl, alkoxy, halo, haloalkyl and haloalkoxy) or aralkyl (substituted by —C(O)$OR^7$ or —C(O)N($R^7$)$_2$ and optionally by one or more substituents selected from the group consisting of alkyl, alkoxy, halo, haloalkyl and haloalkoxy);
$R^{13}$ is a branched alkylene chain, a straight or branched alkenylene chain or a cycloalkylene; and
$R^{14}$ is alkyl, aryl or aralkyl;
as a single stereoisomer, a mixture of stereoisomers, a racemic mixture of stereoisomers; or as a cyclodextrin clathrate thereof, or as a pharmaceutically acceptable salt thereof.

17. The pharmaceutical composition of claim 6 wherein the compound of formula (II) is a compound of formula (II) wherein:
$R^1$, $R^2$ and $R^3$ are each independently halo, -$OR^6$, -$SR^6$ or -N($R^7$)$R^8$;
each $R^4$ is -$R^9$-$R^{12}$, -$R^9$-$R^{13}$-$R^{11}$, -$R^9$-O-$R^{12}$, -$R^9$-C(O)-$R^{10}$-$R^{11}$, -$R^9$-N($R^7$)-$R^{10}$-$R^{11}$, -$R^9$-S(O)$_t$-$R^{10}$-$R^{11}$ (where t is 0 to 2), or -$R^9$-C(F)$_2$-$R^9$-$R^{11}$;
$R^5$ is aryl (optionally substituted by one or more substituents selected from the group consisting of alkyl, alkoxy, halo, and haloalkoxy) or aralkyl (optionally substituted by one or more substituents selected from the group consisting of alkyl, alkoxy, halo, and haloalkoxy);
each $R^6$ is independently hydrogen, alkyl, aralkyl, -C(O)$R^7$ or -C(O)$OR^7$;
each $R^7$ is independently hydrogen, alkyl, aryl, or aralkyl;
$R^8$ is independently hydrogen, alkyl, aryl, aralkyl, or cycloalkyl (optionally substituted with one more substituents selected from the group consisting of alkyl, -N($R^7$)$_2$, and -C(O)0$R^7$);

each $R^9$ is independently a direct bond or a straight or branched alkylene chain;

each $R^{10}$ is independently a straight or branched alkylene chain, a straight or branched alkenylene chain, a straight or branched alkynylene chain or a cycloalkylene;

each $R^{11}$ is independently -C(O)OR$^7$ or -C(O)N(R$^7$)$_2$;

$R^{12}$ is aryl (substituted by -C(O)OR$^7$ or -C(O)N(R$^7$)$_2$ and optionally by one or more substituents selected from the group consisting of alkyl, alkoxy, halo and haloalkoxy) or aralkyl (substituted by -C(O)OR$^7$ or -C(O)N(R$^7$)$_2$ and optionally by one or more substituents selected from the group consisting of alkyl, alkoxy, halo and haloalkoxy);

$R^{13}$ is a branched alkylene chain, a straight or branched alkenylene chain or a cycloalkylene.

18. The pharmaceutical composition of claim 17 wherein the compound of formula (II) is a compound of formula (II) wherein:

$R^1$, $R^2$ and $R^3$ are each independently halo, -OR$^6$, or -SR$^6$;

$R^4$ is -R$^9$-O-R$^{10}$-R$^{11}$;

$R^5$ is aryl (optionally substituted by one or more substituents selected from the group consisting of alkyl, alkoxy, halo, and haloalkoxy) or aralkyl (optionally substituted by one or more substituents selected from the group consisting of alkyl, alkoxy, halo, and haloalkoxy);

each $R^6$ is independently hydrogen, alkyl, aryl, or aralkyl;

each $R^7$ is independently hydrogen, alkyl, aryl, or aralkyl;

$R^9$ is a direct bond or a straight or branched alkylene chain;

$R^{10}$ is an straight or branched alkylene chain, a straight or branched alkenylene chain, a straight or branched alkynylene chain or a cycloalkylene; and $R^{11}$ is -C(O)OR$^7$ or -C(O)N(R$^7$)$_2$.

19. The pharmaceutical composition of claim 18 wherein the compound of formula (II) is a compound of formula (II) wherein:

$R^1$, $R^2$ and $R^3$ are each -OR$^6$;

$R^4$ is -R$^9$-O-R$^{10}$-R$^{11}$;

$R^5$ is aryl (optionally substituted by one or more substituents selected from the group consisting of alkyl, alkoxy, halo, and haloalkoxy);

$R^6$ is hydrogen, alkyl, aryl, or aralkyl;

each $R^7$ is independently hydrogen, alkyl, aryl, or aralkyl;

$R^9$ is a direct bond;

$R^{10}$ is a straight or branched alkylene chain, a straight or branched alkenylene chain, or a straight or branched alkynylene chain; and $R^{11}$ is -C(O)OR$^7$ or -C(O)N(R$^7$)$_2$.

20. The pharmaceutical composition of claim 19 wherein the compound of formula (II) is selected from the group consisting of:

(5S,6R,7E,9E,13E,15S)-16-(4-fluorophenoxy)-5,6,15-trihydroxy-3-oxahexadeca-7,9,13-trien-11-ynoic acid, methyl ester;

(5S,6R,7E,9E,13E,15S)-16-(4-fluorophenoxy)-5,6,15-trihydroxy-3-oxahexadeca-7,9,13-trien-11-ynoic acid;

(5S,6S,7E,9E,13E,15S)-16-(4-fluorophenoxy)-5,6,15-trihydroxy-3-oxahexadeca-7,9,13-trien-11-ynoic acid, methyl ester; and (5S,6S,7E,9E,13E,15S)-16-(4-fluorophenoxy)-5,6,15-trihydroxy-3-oxahexadeca-7,9,13-trien-11-ynoic acid.

\* \* \* \* \*

UNITED STATES PATENT AND TRADEMARK OFFICE
CERTIFICATE OF CORRECTION

PATENT NO. : 7,223,798 B2
APPLICATION NO. : 10/782024
DATED : May 29, 2007
INVENTOR(S) : John G. Bauman et al.

It is certified that error appears in the above-identified patent and that said Letters Patent is hereby corrected as shown below:

Column 64
Line 29, ", $-R^9-R^{10}-R^{11}$," should read as -- , $-R^9-R^{13}-R^{11}$, --
Line 62, "-C(O)OR" should read as -- $-C(O)OR^7$ --

Column 70
Line 67, "$-C(O)0R^7$" should read as -- $-C(O)OR^7$ --

Signed and Sealed this

Fifth Day of August, 2008

JON W. DUDAS
*Director of the United States Patent and Trademark Office*